(12) United States Patent
Zhu et al.

(10) Patent No.: US 7,416,840 B2
(45) Date of Patent: Aug. 26, 2008

(54) REPLICATION OF HEPATITIS C VIRUS IN NON-HEPATIC EPITHELIAL AND MOUSE HEPATIC CELLS

(75) Inventors: Qing Zhu, Emeryville, CA (US); Ju-Tao Guo, Lansdale, PA (US); Christoph Seeger, Elkins Park, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 10/536,955

(22) PCT Filed: Dec. 12, 2003

(86) PCT No.: PCT/US03/39722

§ 371 (c)(1), (2), (4) Date: Oct. 18, 2005

(87) PCT Pub. No.: WO2004/055216

PCT Pub. Date: Jul. 1, 2004

(65) Prior Publication Data

US 2006/0128011 A1   Jun. 15, 2006

Related U.S. Application Data

(60) Provisional application No. 60/433,303, filed on Dec. 13, 2002.

(51) Int. Cl.
*C12Q 1/70* (2006.01)
*C12N 5/10* (2006.01)
*C12N 15/87* (2006.01)

(52) U.S. Cl. .............. 435/5; 435/32; 435/354; 435/366; 435/367; 435/455; 424/228.1; 424/9.2

(58) Field of Classification Search ............. None
See application file for complete search history.

(56) References Cited

U.S. PATENT DOCUMENTS 5,679,342 A * 10/1997 Houghton et al. ........ 424/93.21
5,968,775 A * 10/1999 Houghton et al. ........... 435/69.3
6,096,541 A *  8/2000 Houghton et al. ........... 435/370

OTHER PUBLICATIONS

Germi, et al. Mosquito Cells Bind and Replicate Hepatitis C Virus. J Med Virol. (2001) 64:6-12.*
Seipp, et al. Establishment of persistent hepatitis C virus infection and replication in vitro. J Gen Virol. (1997) 78: 2467-2476.*
Kato, et al. Replication of Hepatitis C Virus in Cultured Non-neoplastic Human Hepatocytes. Jpn J Cancer Res. 1996; 87:787-792.*
Sasagawa et al. Synergistic Induction of Apoptosis in Murine Hepatoma Hepa1-6 Cells by IFN-γ and TNF-α. Biochem Biophys Res Comm 2000 272(3):674-680.*
Wu, et al. Establishment and characterization of differentiated, nontransformed hepatocyte cell lines derived from mice transgenic for transforming growth factor alpha. Proc Natl Acad Sci U S A. Jan. 18, 1994;91(2):674-8.*
Choo, et al. Isolation of a cDNA Clone Derived from a Blood-borne Non-A, Non-B Viral Hepatitis Genome. Science. 1989; 244(4902): 359-362.*
Kato, et al. Susceptibility of Human T-lymphotropic Virus Type I Infected Cell Line MT-2 to Hepatitis C Virus Infection. Biochem. Biophys. Res. Comm. 1995; 206(3): 863-869.*
Mizuno, et al., Virion-like Structures in HeLa G Cells Transfected with the Full-length Sequence of the Hepatitis C Virus Genome. Gastroenterol. 1995; 109(6): 1933-1940.*
Lohmann, V., et al., "Replication of Subgenomic Hepatitis C Virus RNAs in a Hepatoma Cell Line," Science, vol. 285:110-113, (1999).
Blight, K.J., et al., "Efficient Initiation of HCV RNA Replication in Cell Culture," Science, vol. 290:1972-1974, (2000).
Blight, K.J., et al., "High Permissive Cell Lines for Subgenomic and Genomic Hepatitis C Virus RNA Replication," Journal of Virology, vol. 76:13001-13014, (2002).
Zhu, Q., et al., "Unexpected Host Range of Hepatitis C Virus Relicons," Hepatology, vol. 39:835-838 (2004).
Deres, K., et al., "Interfering with Capsid Formation: A Practicable Antiviral Strategy Against Hepatitis B Virus?" Hepatology, vol. 39:838-840, (2004).

\* cited by examiner

*Primary Examiner*—Mary E. Mosher
*Assistant Examiner*—Stuart W Snyder
(74) *Attorney, Agent, or Firm*—Dann, Dorfman, Herrell & Skillman; Kathleen D. Rigaut; Robert C. Netter

(57) ABSTRACT

Cells and cell lines which replicate HCV of non-hepatic human and non human origin are disclosed. Also provided are methods of using such cells and cell lines to identify anti-HCV agents for the treatment of HCV infection.

23 Claims, 15 Drawing Sheets

6A

6B

7A

7B

8A

8B

9A

9B

Figures 1A, 1B:
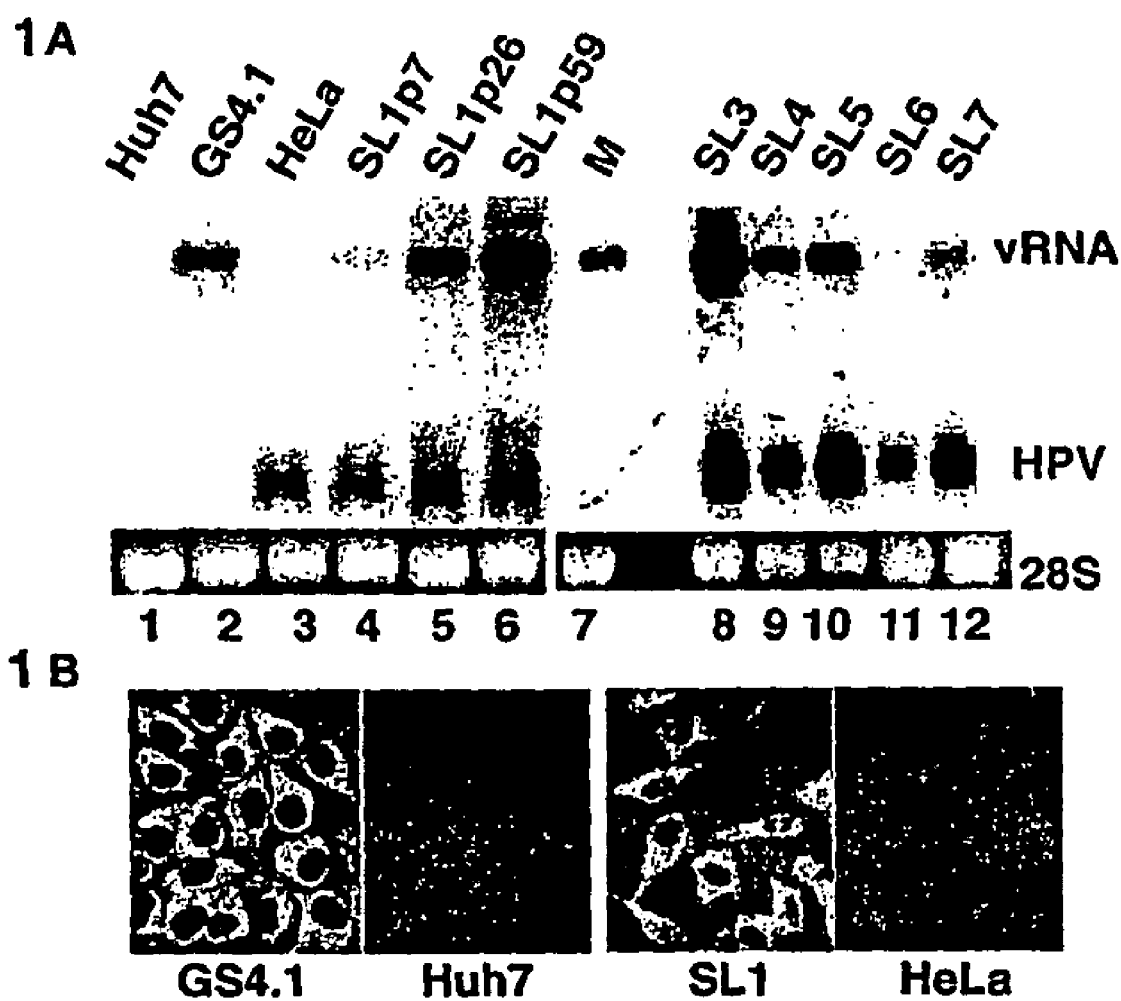

Figures 11A-11D
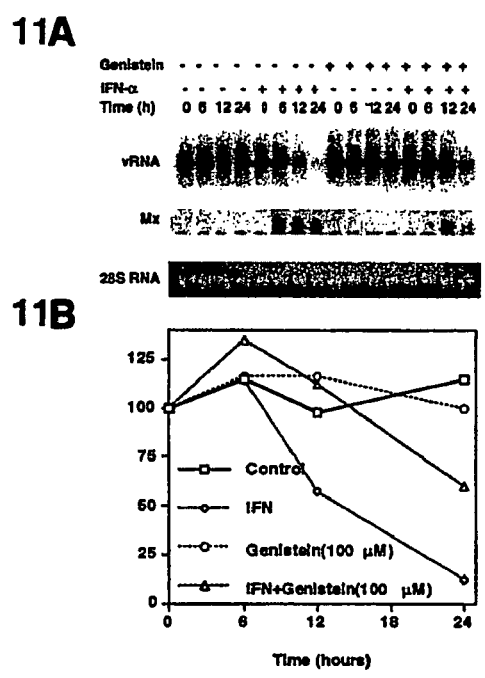
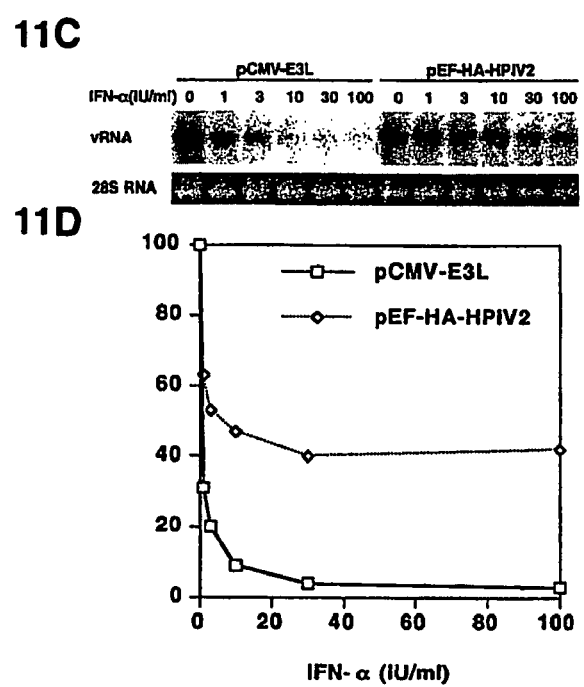

12A

12B

13A

13B

13C

14 A

14B

15A

US 7,416,840 B2

REPLICATION OF HEPATITIS C VIRUS IN NON-HEPATIC EPITHELIAL AND MOUSE HEPATIC CELLS

This application is a § 371 application of PCT/US03/39722 filed 12 Dec. 2003, which in turn claims priority to Provisional Application 60/433,303 filed 13 Dec. 2002. Each of the above identified applications is incorporated by reference herein.

GOVERNMENT RIGHT

Pursuant to 35 U.S.C. Section 202(c), it is acknowledged that the United States government has certain rights in the invention described herein, which was made in part with funds from the National Institutes of Health Grant No. AI48046.

FIELD OF THE INVENTION

This invention relates to the fields of molecular biology and pathology. Novel animal cell lines and non-hepatic human epithelial cell lines for the replication of hepatitis C virus (HCV), as well as methods for screening for anti-HCV drugs or HCV receptors using these cell lines are disclosed. Furthermore, adaptive sequence mutations in the HCV genome, which permit replication in non-human, and non-hepatic cell lines are also provided.

BACKGROUND OF THE INVENTION

Several publications and patent documents are cited in this application in order to more fully describe the state of the art to which this invention pertains. The disclosure of each of these citations is incorporated by reference herein.

Hepatitis C virus (HCV) is an enveloped, positive stranded RNA virus that belongs to the Flaviviridae, a family of viruses including human pathogens such as yellow fever virus, dengue virus and West Nile virus (Q. L. Choo et al., *Science* 244, 359-62 (1989)). Although broad tissue and species tropisms are hallmarks of these viruses, HCV replication has so far only been detected in human and chimpanzee livers. Moreover, for reasons that are not yet understood, HCV RNA levels in infected liver tissue are extremely low, generally below one copy of RNA per cell and hence, can only be detected with PCR, making it difficult to determine whether secondary sites for viral replication exist (J. Boisvert et al., *J Infect Dis* 184, 827-35 (Oct. 1, 2001); R. E. Lanford, et al., *J Virol* 69, 8079-83 (1995)).

HCV encodes a polyprotein that is processed proteolytically into ten polypeptides (K. E. Reed, C. M. Rice, *Curr Top Microbiol immunol* 242, 55-84 (2000)). Three of them are structural proteins required for capsid formation (core) and assembly into enveloped viral particles (E1 and E2). Four of them are enzymes including cysteine and serine proteases (NS2 and NS3), an ATP dependent helicase (NS3) and a RNA-directed RNA polymerase (NS5B). The functions of the remaining three polypeptides, p7, NS4B, and NS5A, for viral replication are not yet known. For study of replication of HCV in tissue culture cells, the structural proteins can be replaced with a selectable marker, such as the neomycin phosphotransferase. See for example FIG. 2, left panel of Lohman et al. (V. Lohmann et al., *Science* 285, 110-3 (1999)). Replication of such subgenomic HCV replicons in tissue culture cells has so far only been demonstrated in the human hepatoma cell line Huh7, consistent with the narrow host and tissue tropism of HCV infections.

HCV infection poses a significant public health problem. Approximately 3% of the world's population has persistent HCV infection. In 1989, the virus was identified as the major aetiological agent responsible for post-transfusion non-A and non-B hepatitis. Following primary HCV infection, persistent viraemia and chronic hepatitis develop in the majority of cases. Efforts to elucidate the mechanisms behind viral persistence and hepatocellular damage have been frustrated by the lack of a reliable cell culture system for viral propagation in vitro. In addition, as the chimpazee is the only experimental animal susceptible to HCV infection, progress in research is hampered by the lack of a small animal model to facilitate pathophysiological studies as well as the evaluation of antiviral treatment and vaccine strategies.

Furthermore, although the initial HCV infection is asymptomatic, subsequent clinical manifestations of HCV induced liver disease include fibrosis, cirrhosis, and hepatocellular carcinoma (Alter, H. J., and L. B. Seeff. 2000. Semin. Liver Dis. 20:17-35). Combination antiviral therapy with alpha interferon (IFN-$\alpha$) and ribavirin, a purine nucleoside analogue, arrests disease progression and can lead to sustained recovery in only 45 to 80% of treated patients (Di Bisceglie, A. M., and J. H. Hoofnagle. 2002. Hepatology 36:S121-S127). Additionally, response to IFN-$\alpha$ therapy can vary significantly depending on the viral genotype, ranging from 30 to 40% for genotype 1 to as high as 80% for genotypes 2 and 3. This suggests that viral determinants also play an important role in regulating the cellular IFN response against HCV (Kinzie, J. L., et al., 2001. J. Viral Hepatitis 8:264-269; McHutchison, J. G., et al., 1998. N. Engl. J. Med. 339:1485-1492). The parameters determining the success or failure of antiviral therapy are not understood, and their identification represents a major challenge in HCV biology.

Therefore, there is a desperate need for non-hepatic cell culture systems, and small animal models for the identification and characterization of anti-viral agents for the prevention and treatment of HCV infection. Additionally, there is a need in the art to elucidate the mechanism of HCV inhibition by IFN-$\alpha$, so that other treatments may be found.

SUMMARY OF THE INVENTION

The present invention provides HCV replicating cells and cell lines derived from human non-hepatic cells or non-human cells. According to one embodiment of the invention, the cells are human epithelial cells of non-liver origin, such as, HeLa cells. According to another embodiment of the invention, the cells capable of replicating HCV are hepatoma and hepatocyte cells of mouse origin, such as, Hepa1-6 cells, or AML12 cells respectively.

The present invention also provides a non-human host animal comprising cells infected with HCV. In one embodiment of the invention, the host animal is a mouse. In another embodiment of the invention, the cells infected with HCV are mouse hepatoma cells.

Also provided by the present invention are methods for producing human non-hepatic cells or non-human cells that are capable of replicating HCV, and cell lines comprising the same. Such methods include transfection with total HCV RNA or an HCV replicon which comprises one or more adaptive mutations which facilitate replication in a cell of interest.

The present invention further provides methods for screening an agent that modulates HCV replication by incubating the agent with the aforementioned cells or administering the agent to the aforementioned host animal comprising cells replicating HCV and assessing said agent for modulation of HCV replication. Such agents may inhibit or enhance production of HCV. These agents may be cytopathic or non-cytopathic to HCV infected cells. Agents which activate aspects of the JAK/STAT pathway may also be screened using the cells and cell lines of the invention.

Figure 10:
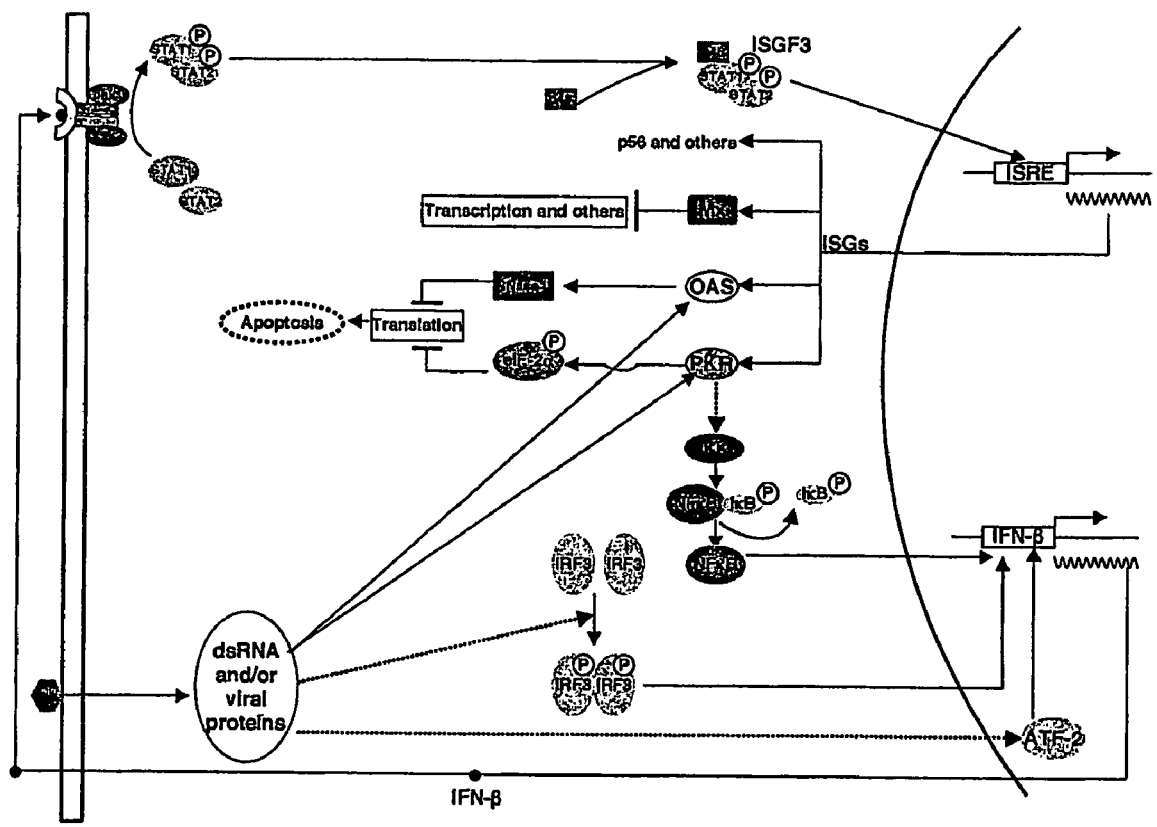

Also provided by the present invention are HCV derived polynucleotides comprising adaptive mutations. The present inventor has discovered that these mutations are associated with expanded tropism of HCV.

Additionally, the present invention provides polypeptides encoded by the mutated HCV polynucleotides described above.

BRIEF DESCRIPTION OF THE DRAWINGS

FIGS. 1A and 1B are a Northern blot (FIG. 1A) and micrographs showing replication of HCV subgenomic replicons in HeLa cells. (FIG. 1A) Detection of HCV viral RNA. Total RNA (5 μg) was isolated from HeLa cell lines (SL1, SL3-7) that were established from G418 resistant cell colonies and analyzed by Northern blot analysis. Blots were hybridized with radiolabeled RNA probes corresponding to the HCV NS5 region to detect viral RNA (vRNA) and the ΔE1 region of human papilloma virus (HPV) present in HeLa cells. In vitro transcribed HCV RNA (1 ng, +5 μg total RNA from Huh7 cells, lane 7) served as a marker (M) and control for the hybridization reaction and 28S ribosomal RNA as a control for the amount of RNA present in each sample analyzed. GS4.1 is a Huh7 derived cell line expressing HCV subgenomic replicons. RNA in SL1 cells was analyzed from cells harvested at the indicated passage (p). SL3-7 were analyzed at p3 (FIG. 1B). Immunohistochemical analysis of HCV replication in HeLa cells. Expression of NS5A in GS4.1 and SL1 cells (p26) was detected with a monoclonal antibody bound to fluorescent isothiocyanate (FITC)-conjugated antibody. Parental Huh7 and HeLa cells served as controls.

FIG. 2 diagrams sequence analysis of HCV subgenomes in HeLa and mouse hepatoma Hepa1-6 cells. (Left section) The physical map of HCV subgenomic RNA include the positions of the first amino acid NS3 and the last residue of the polyprotein. The internal ribosomal entry site for the translation of the NS genes is indicated (EMCV-IRES). (Right section) Mutations causing amino acid changes identified in cDNAs isolated from subgenomic replicons present in GS4.1 and the indicated HeLa (SL1 (p26); SL2, p5) and Hepa1-6 cell lines (MH1 (p12), MH2 (p4), MH4 (p4)) are depicted with horizontal bars. Four independent clones were sequenced from each PCR fragment that was amplified from cDNAs obtained from total RNA purified from the indicated cell lines. Mutations present in more than one cell line are indicated by amino acid position. Mutations that occurred in 50% of the clones analyzed are marked with an asterisk. Mutations that occurred in only one of four clones analyzed were not included in the figure. A deletion identified in cDNA clones obtained from SL1 cells spanning amino acids 2371 to 2413 is indicated (Δ).

FIGS. 3A and 3B are a Northern blot and micrographs showing replication of HCV subgenomes in mouse hepatoma cells. (A) Detection of HCV RNA. RNA in Hepa1-6 cell lines (MH1-5) that were established from G418 resistant cell colonies and analyzed as described in the legend to FIG. 1 except that a radiolabeled probe specific to mouse albumin cDNA was used in lieu of the probe against HPV. MH4-5 were analyzed at p4 (B). Immunohistochemical analysis of HCV replication in MH1 cells (p3). Expression of NS5A was detected as described in FIG. 1. Hepa1-6 cells served as a negative control.

FIG. 4 is a Northern blot showing detection of HCV RNA in mouse hepatocyte cells. AML12 cells were transfected with total RNA from GS4.1 cells, which express subgenomic HCV replicons, and HFL cells, which express full length HCV genomes. 5 micrograms of total RNA was isolated from AML12 cell lines (MA6-5 to MA6-8, and MAC1) that were established from G418 resistant cell colonies and analyzed by Northern blot analysis. sgRNA indicates subgenomic RNA and flRNA full length genomic RNA.

FIGS. 5A and 5B are two Northern blots showing the antiviral activity of the HCV RNA polymerase inhibitor 2'-C-methyladenosine (2CMA). GS4.1 (Huh7) cells (5A) and SL1 (HeLa) cells (5B) were treated with 10 μM 2CMA. The cells were harvested at the indicated time points. Total cellular RNA was extracted and viral RNA (vRNA) analyzed by Northern blot analysis.

FIGS. 6A and 6B are two graphs depicting antiviral activity of the HCV RNA polymerase inhibitor 5-OH-cytidine. GS4.1 (Huh7) cells and SL1 (HeLa) cells were treated with the indicated amounts of 5-OH-cytidine. The DNA polymerase inhibitor 5-OH-deoxy-cytidine was used as a negative control. The cells were harvested 72 hours after incubation with the drugs. Total cellular RNA was extracted and viral RNA analyzed by Northern blot analysis. The intensity of the bands corresponding to HCV RNA was determined with a Fuji phosphoimager.

FIGS. 7A and 7B are a Northern blot and a graph showing antiviral activity of IFN-α in Huh 7 (GS4.1) and HeLa (SL1) cell lines containing HCV replicons. (7A) Viral RNA (vRNA) levels present in GS4.1 and SL1 cells incubated with 0, 0.1, 0.3, 1, 3, 10, 30, and 100 IU of IFN-α/ml (lanes 1 to 9 and 12 to 18) and with 0.01 and 0.03 IU/ml (lanes 10 and 11) for 72 h were determined by Northern blot analysis. rRNA (28S rRNA) served as a control for the amount of RNA loaded per lane. (7B) Amounts of HCV RNA were determined with a Fuji phosphorimager, and the values were plotted as the percentages of the values obtained with untreated cells in lanes 1 and 9.

FIGS. 8A and 8B are micrographs and histograms showing that IFN-α induces apoptosis of SL1 cells. (8A) Annexin V-FITC staining. SL1 cells grown on glass coverslips were left untreated (upper left) or treated with 100 IU of IFN-α/ml for 6 h (upper right) or 20 h (lower left) or with 100 IU of IFN-α/ml and 20 μM caspase inhibitor ZVAD-FMK for 20 h (lower right). Cells were then processed for annexin V FITC staining and viewed with a fluorescence microscope. (8B) Flow cytometry analysis. SL1 cells were left untreated (upper left) or treated with 100 IU of IFN-α/ml (upper right) or with IFN-α and 20 μM ZVAD-FMK (lower left) for 24 h. To inhibit viral replication, SL1 cells were incubated at 39° C. for 60 h and then treated with 100 IU of IFN-α/ml for 24 h (lower left). Cells were harvested and processed for annexin V-FITC staining and analyzed by flow cytometry. The percentages of FITC-positive cells are indicated.

FIGS. 9A and 9B are Northern blots and a graph showing a comparison of IFN— a responses against HCV and flavivirus Kunjin virus replicons in HeLa cells. (9A) SL1 and KUNCD20 cells were incubated with 0, 0.01, 0.04, 0.16, 0.625, 2.5, 10, 40, and 160 IU of IFN-α/ml (lanes 1 to 9 and 10 to 18, respectively) for 72 h, and viral RNA levels were determined by Northern blot analysis with a plus-strand-specific RNA probe for the neomycin phosphotransferase II gene. Mx-1 mRNA served as a control for IFN-α-induced gene expression. β-Actin mRNA served as a control for the amount of RNA loaded per lane. (9B) The amounts of HCV and Kunjin virus replicon RNA (arbitrary units) were determined with a Fuji phosphorimager.

FIG. 10 shows an overview of the interactions between a virus and the IFN system. Replication of viruses in cells produces dsRNA and viral proteins, which activate PKR and OAS/RNase L antiviral pathways and also signal to the promoter of the IFN-β gene by activating transcription factors IRF3, NF-κB, and ATF2. Secreted IFN binds to its receptor and activates receptor-associated Jak kinases, leading to the formation of the trimeric transcription factor ISGF3, which binds to the IFN-stimulated response element (ISRE) on promoters of IFN-stimulated genes. Among the products of the several hundred genes induced by IFN, PKR, OAS/RNase L, and Mx are the best-characterized antiviral proteins, which inhibit different stages of viral replication and induce apoptosis of virally infected cells.

FIGS. 11A-11D are Northern blots and two graphs showing inhibition of the IFN-α response by genistein and the V protein of HPIV2. (11A) GS4.1 cells were incubated with 100 μg of genistein/ml for 2 h and then with 100 IU/ml IFN-α for an additional 24 h. Viral RNA levels were determined by Northern blot analysis. The cells were harvested at the indicated time points, and Mx-A mRNA and viral RNA levels were determined by Northern blot analysis. Ribosomal 28S RNA was used as a control for the amount of RNA loaded on each lane. (11B) The amounts of viral RNA were measured with a phosphorimager and plotted as percentages of the values obtained with untreated cells. (11C) GS4.1 cells were transfected with pCMV-E3L and pEF-HA-HPIV2 and treated with IFN-α at the indicated concentrations for 3 days. HCV RNA was subjected to Northern blot analysis. (11D) Viral RNA levels were determined with a Fuji phosphorimager and plotted as the percentages of the values obtained with untreated cells.

Figure 12A:
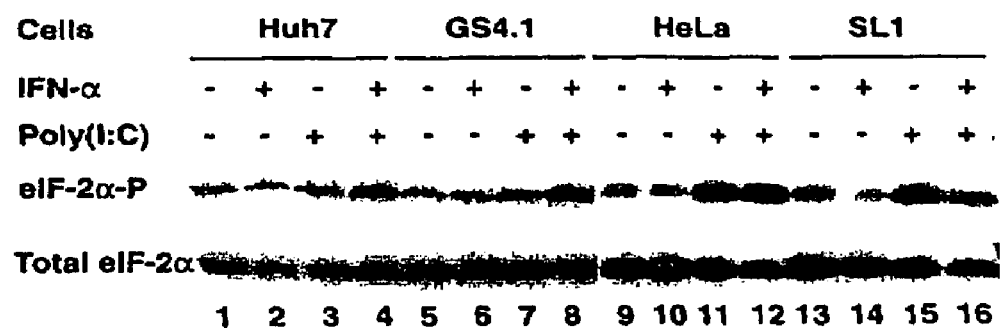
Figure 12B:
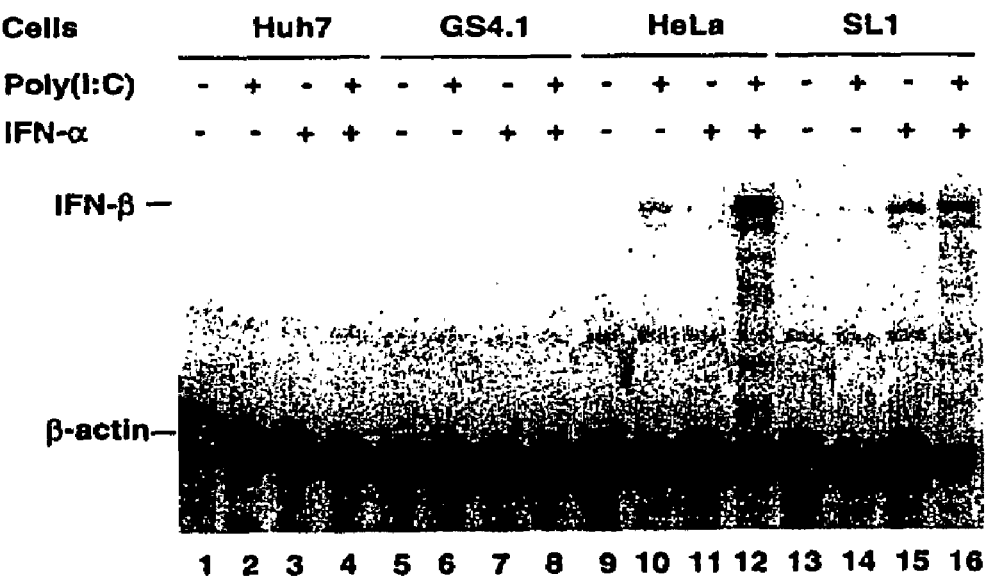

FIGS. 12A and 12B show the dsRNA response in parental Huh7 and HeLa cells and HCV replicon-containing GS4.1 and SL1 cells. (12A) Phosphorylation of eIF-2α. Huh7, GS4.1, HeLa, and SL1 cells were left untreated (lanes 1, 5, 9, and 13) or treated with 100 IU of IFN-α/ml for 12 h (lanes 2, 4, 6, 8, 10, 12, 14, and 16) and then transfected with poly(I:C) and incubated for 3 h (lanes 3, 4, 7, 8, 11, 12, 15, and 16). eIF-2α-P and total eIF-2α were determined by Western blots analysis with a monoclonal antibody specific for eIF-2α-P and an antibody specific for total eIF-2α protein. (12B) Induction of IFN-β mRNA by dsRNA and IFN-α. Parental Huh7 and HeLa cells and HCV replicon-containing GS4.1 and SL1 cells were left untreated (lanes 1, 5, 9, and 13) or treated with 100 IU of IFN-α/ml (lanes 3, 4, 7, 8, 11, 12, 15, and 16) for 12 h and then transfected with poly(I:C) (lanes 2, 4, 6, 8, 10, 12, 14, and 16) for 3 h. An RNase protection assay was performed with probes specific for IFN-β and β-actin mRNAs.

Figure 13A:
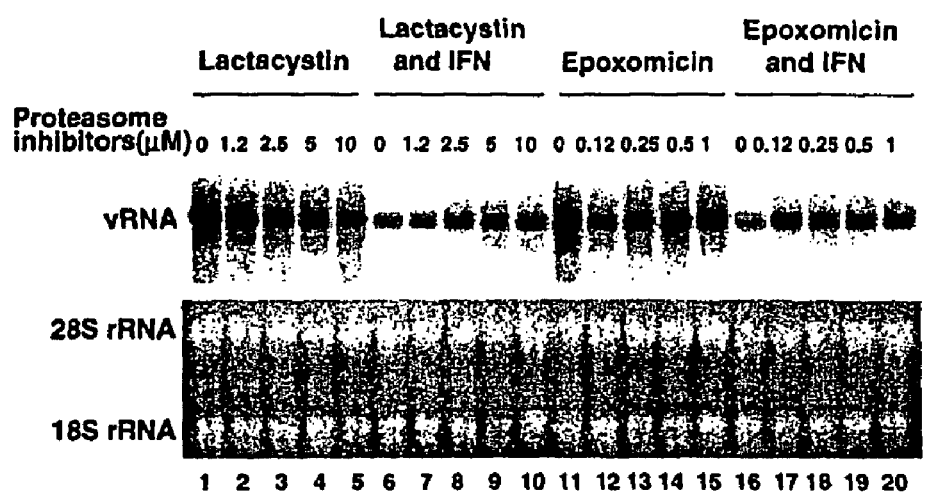
Figure 13B:
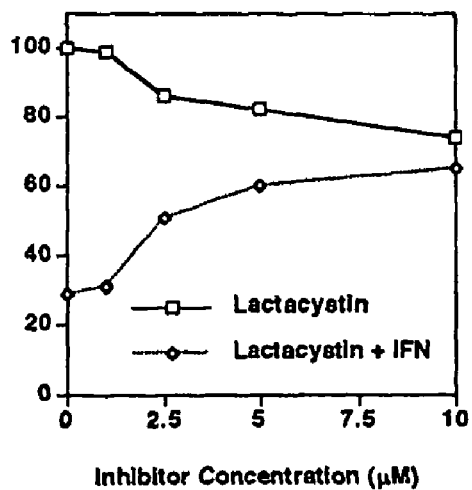
Figure 13C:
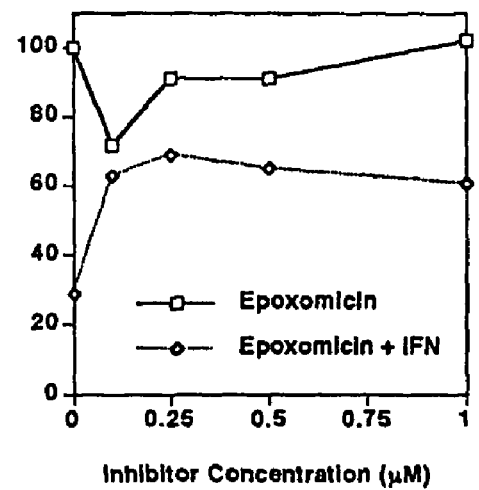

FIGS. 13A-13C show dose-dependent inhibition of the IFN-α response against subgenomes by lactacystin and epoxomicin. (13A) Cells were incubated with lactacystin and epoxomicin at the indicated concentrations for 7 h and then for an additional 12 h without the drugs. One hour after incubation with the proteasome inhibitors, IFN-α (100 IU/ml) was added for 6 h to a fraction of the cell culture plates (lanes 6 to 10 and 16 to 20). Viral RNA levels were determined by Northern blot analysis. rRNA was used as a control for the amount of RNA present in the samples. (13B and 13C) The amount of viral RNA was measured with a phosphorimager, and values were plotted as percentages of the values obtained with untreated cells.

Figure 14A:
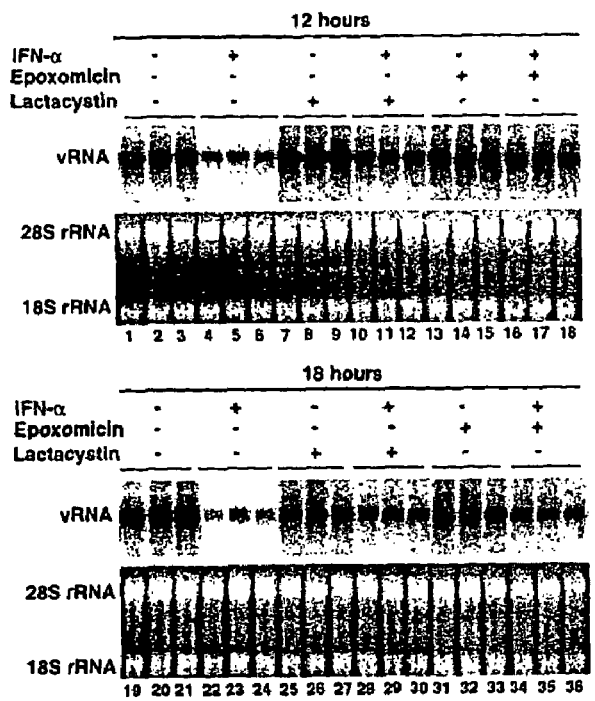
Figure 14B:
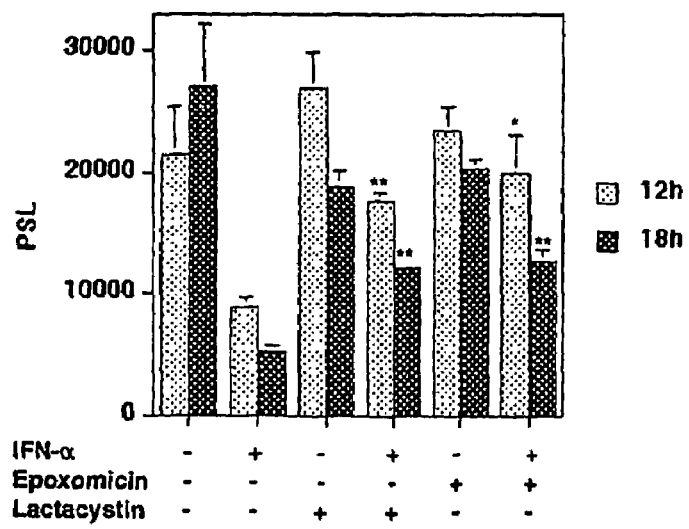

FIGS. 14A and 14B are Northern blots and a graph showing that proteasome inhibitors block the IFN-α response against HCV replicons. (14A) GS4.1 cells were left untreated (lanes 1 to 3 and 19 to 21) or treated with 100 IU of IFN-α/ml for 6 h (lanes 4 to 6 and 22 to 24), with 5 μM lactacystin (lanes 7 to 9 and 25 to 27) or 1 μM epoxomicin (lanes 13 to 15 and 31 to 33) alone for 7 h, or with 5 μM lactacystin (lanes 10 to 12 and 28 to 30) or 1 μM epoxomicin (lanes 16 to 18 and 34 to 36) alone for 1 h and then in the presence of 100 IU of IFN-α/ml for an additional 6 h. Cells were harvested at 12 h (lanes 1 to 18) and 18 h (lanes 19 to 36) after addition of the cytokine. Viral RNA levels were determined by Northern blot analysis. rRNA was used as a control for the amount of RNA present in the samples. (14B) The amount of viral RNA was measured with a phosphorimager and the mean values and standard deviations from three samples were plotted. *, $P<0.05$; **, $P<0.01$. PSL, arbitrary units.

Figures 15A, 15B:
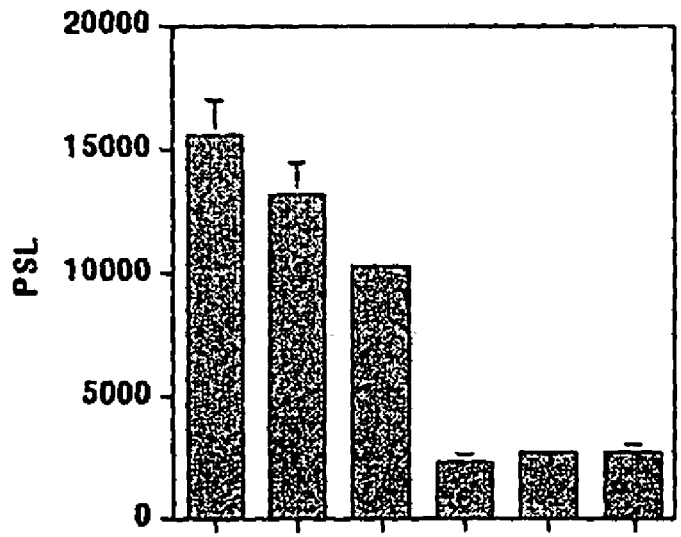

FIGS. 15A and 15B show a Northern blot graph demonstrating that proteasome inhibitors prevent establishment of an IFN-α response against HCV replicons. (15A) GS4.1 cells were treated with IFN-α for 10 h, followed by treatment with the indicated proteasome inhibitors for 12 h. Cells were left untreated (lanes 1 to 3 and 4 to 6) or treated with 100 IU of IFN-α/ml for 10 h (lanes 7 to 18), followed by treatment with 10 μM lactacystin (lanes 13 to 15) or 1 μM epoxomicin (lanes 16 to 18) for 12 h. Cells were harvested at 0, 10, and 18 h after the cytokine treatment, as indicated. Viral RNA levels were determined by Northern blot analysis. rRNA was used as a control for the amount of RNA present in the samples. (15B) The amount of viral RNA was measured with a phosphorimager and the mean values and standard deviations from three samples were plotted. PSL, arbitrary units.

DETAILED DESCRIPTION OF THE INVENTION

The hepatitis C virus (HCV) pandemic affects the health of more than 170 million people and is the major indication for orthotopic liver transplantations (OLT). Although the human liver is the primary site for HCV replication, it is not known whether extrahepatic tissues are also infected by the virus and whether non-primate cells are permissive for RNA replication. However, because viral replication leads to the accumulation of mutations, it is conceivable that variants can emerge with novel properties such as the potential to replicate in different cell types of various species. Furthermore, accumulation of a large number of quasispecies may also contribute to resistance to IFN-α treatment. Therefore, it is important to determine the properties of HCV variants, and the effect such variation has on the efficacy of IFN-α therapy.

Provided herein is evidence that subgenomic HCV RNAs can replicate in mouse hepatoma and non-hepatic human epithelial cells. Moreover, efficient replication requires adaptation of the virus to cell-type specific environmental conditions. These results show that HCV RNA replication can lead to the accumulation of mutants with altered tissue and host tropism thereby facilitating the development of small animal models for HCV infection.

In accordance with the present invention, there are provided nucleic acids and stably-transfected human non-hepatic, and murine hepatic cell lines that replicate HCV. Also provided are methods of use for such cells for identifying therapeutic anti-viral agents for the treatment of HCV infection. Additionally, the availability of a murine line which replicates HCV enables the production of a greatly needed mouse model of HCV infection. Furthermore, the invention provides polynucleotides and their corresponding polypeptides which have adaptive mutations which results in expanded tropism of HCV.

The detailed description set forth below describes preferred methods for making and using the nucleic acids and cell lines of the present invention, and for practicing the methods of the invention. Any molecular cloning or recombinant DNA techniques not specifically described are carried out by standard methods, as generally set forth, for example, in Sambrook et al., "DNA Cloning, A Laboratory Manual," Cold Spring Harbor Laboratory, 1989 and Ausubel et al. Current Protocols in Molecular Biology, J. Wiley & Sons, 1995.

I. Definitions

The following definitions are provided to aid in understanding the subject matter regarded as the invention.

As used herein, "hepatitis C virus" or "HCV" shall mean any representative of a diverse group of related viruses classified within the *hepacivirus* genus of the Flaviviridae family.

"Anti-HCV compounds" may include any inhibitor of HCV-derived enzymes, such as protease, helicase, and polymerase inhibitors. Anti-HCV compounds also include IRES inhibitors, glycosylation inhibitors, and molecules which block the HCV receptor (thus preventing entry into cells.) Other anti-HCV compounds include compounds which enhance the specific or non-specific immune response, thereby ameliorating HCV infection or symptoms.

"HCV replication levels" may be measured by methods known in the art, including but not limited to detection of replicated HCV replicons, HCV NS protein production, or incorporation of detectably labeled nucleotides into an HCV nucleic acid.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism or virus in which it originated. When applied to RNA, the term "isolated nucleic acid" refers primarily to an RNA molecule that has been sufficiently separated from other nucleic acids with which it would be associated in its natural state (i.e., in cells or tissues), and explicitly includes viral RNA. An isolated nucleic acid (either DNA or RNA) may further represent a molecule produced directly by biological or synthetic means and separated from other components present during its production.

"RNA subgenome" refers to any molecule which lacks some portion of a genome. For example, an RNA subgenome can be an HCV RNA molecule in which a structural gene has been replaced with a selection agent.

All amino acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

"Variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to expand the tropism of viral RNA, or to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence. The terms "percent similarity", "percent identity" and "percent homology" when referring to a particular sequence are used as set forth in the University of Wisconsin GCG software program.

An "adaptive mutation" is a mutation in a nucleic acid sequence which produces a change in viral properties or activity. For example, and adaptive mutation includes, but is not limited to, a mutation which provides enhanced tropism for HCV, or which alters the efficacy of IFN-α treatment.

An HCV peptide, polypeptide, or protein of the invention includes any analogue, fragment, derivative or mutant which is derived from a HCV peptide or polypeptide and which retains at least one property or other characteristic of the HCV polypeptide. Different "variants" of the HCV polypeptide exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the HCV peptide or polypeptide, (c) variants in which one or more amino acids include a substituent group, and (d) variants in which one or more amino acids are deleted from the HCV peptide or polypeptide. Other HCV peptides or polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such variations, analogues, fragments, derivatives, mutants, and modifications, including alternative nucleic acid processing forms and alternative post-translational modification forms result in derivatives of the HCV peptide or polypeptide that retain any of the biological properties of the HCV peptide or polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given sequence. For example, when used in reference to an amino acid sequence, the phrase includes the sequence per se and molecular modifications that would not affect the fundamental and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector", is a replicon, such as a plasmid, cosmid, bacmid, phage or virus, to which another genetic sequence or element (either DNA or RNA) may be attached so as to bring about the replication of the attached sequence or element.

The phrase "operably linked" when referring to nucleic acid constructs is used herein to indicate that the respective promoter, operator and coding sequences, as well as any other 5' and 3' regulatory sequences, are arranged in the appropriate location, order and reading frame such that the desired control (e.g., expression) is effected under appropriate conditions.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, hybridizations may be performed, according to the method of Sambrook et al., *Molecular Cloning*, Cold Spring Harbor Laboratory (1989), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_m = 81.5° C. + 16.6 \text{Log}[Na+] + 0.41(\% G+C) - 0.63(\% \text{formamide}) - 600/\#bp \text{ in duplex}$$

As an illustration of the above formula, using $[Na^+]=[0.368]$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1× SSC and 0.5% SDS at 65° C. for 15 minutes.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

A "selectable marker" or a "selection agent" refers to a nucleic acid sequence that when expressed confers a selectable phenotype, such as antibiotic resistance, to a transformed cell.

A "viral antigen" shall be any peptide, polypeptide or protein sequence, segment or epitope that is derived from a virus that has the potential to cause a functioning immune system of a host to react to said viral antigen.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

The term "detectably label" is used herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

As used herein, the term "living host" shall mean any non-human autonomous being.

II. Methods for Obtaining HCV RNA and Producing Non-Hepatic Human Cell Lines and Non-Human Hepatic Cell Lines that Replicate HCV The HCV replicating non-hepatic human cell-based and non-human hepatic cell-based systems are prepared according to the general methods set forth below for isolation of nucleic acids, transformation of cultured cells, and maintenance of cell lines.

A. Nucleic Acids

The HCV replicons of the present invention comprise adaptive mutations which alter the ability of HCV to replicate in different cell types. Surprisingly, the present inventors have identified mutations which are associated with expanded viral tropism.

The HCV nucleic acid molecules of the invention may be prepared by two general methods: (1) They may be synthesized from appropriate chemical starting materials, or (2) they may be isolated from biological sources. Both methods utilize protocols well known in the art.

The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages due to the size limitations inherent in current oligonucleotide synthetic methods. Thus, for example, a 3 kilobase double-stranded molecule may be synthesized as several smaller segments of appropriate complementarity. Complementary segments thus produced may be ligated such that each segment possesses appropriate cohesive termini for attachment of an adjacent segment. Adjacent segments may be ligated by annealing cohesive termini in the presence of DNA ligase to construct an entire 3 kilobase double-stranded molecule. A synthetic DNA molecule so constructed may then be cloned and amplified in an appropriate vector.

HCV nucleic acid sequences may be isolated from appropriate biological sources using methods known in the art. For example, total RNA can be extracted with TRIzol reagent from Gibco BRL, although other reagents are also available for this purpose.

In some cases, it may be desirable to synthesize HCV subgenomic RNA wherein a selectable marker gene is substituted for a HCV structural gene.

The availability of HCV replicon encoding nucleic acids enables the production of strains of laboratory mice carrying part or all of the HCV sequence or mutated sequences thereof. Such mice provide an in vivo model for studying HCV infection, and analyzing possible treatment modalities for the same.

Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo.

A transgenic mouse carrying an HCV replicon comprising the adaptive mutations is generated by genomic integration of exogenous genomic sequence encoding HCV. These transgenic animals are useful for drug screening studies as animal models for human diseases.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

A type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

B. Cell Lines

The cell lines of the invention include any cell which supports production of HCV components. These cells include human, non hepatic cells and/or non-human hepatic cells, such as murine hepatic cells. Cell lines useful for practice of the invention include, but are not limited to HELA, a non-hepatic epithelial cell line (ATCC CRL number CCL-2.2), Hepa1-6, a murine hepatoma cell line (ATCC CRL number-1830), and AML-12, a murine hepatocyte cell line (ATCC CRL number-2254).

To achieve stable gene transfer, HCV subgenomic RNA is introduced into host cells. This may be accomplished according to numerous methods known in the art, including, but not limited to: (1) calcium phosphate transfection; (2) transfection with DEAE-dextran; (3) electroporation; and (4) liposome-mediated transfection. For general protocols, see, e.g., chapter 9 in Current Protocols in Molecular Biology, Ausubel et al. (editors), John Wiley & Sons, Inc. 1987-1995. For stable transfer of nucleic acids into mammalian cells, the liposome-mediated transfection method may be used in the present invention because of the large amount of nucleic acid that can be introduced into the cells, thereby increasing the possibility of integration of the nucleic acid into the host genome.

Cells are grown according to standard methods known in the art, such as those set forth in *Culture of Animal Cells: A Manual of Basic Technique* by R. Ian Freshney, 4th ed. Edition, available from the ATCC.

Stable transfectants are selected by the ability of an individual cell colony to grow in the presence of a selection agent, e.g., an antibiotic, by virtue of a resistance-encoding gene on HCV RNA or by isolating cells using FACS and antibodies directed any HCV protein.

Detection and quantitation of expression of HCV gene products in stably-transfected cell lines of the invention can be accomplished using a variety of known assays. For instance, cells transformed with the RNA subgenomes of HCV can be selected with an antibiotic such as G418 (neomycin). Alternatively, cells may be selected based on the presence and accumulation of HCV RNA or HCV gene products. As another example, the starting HCV encoding nucleic acids may be modified to also comprise a hygromycin or puromycin or any other resistance or reporter gene, such that cells transfected with the nucleic acids can be selected by their ability to grow on hygromycin- or puromycin-containing medium. Alternatively, selectable markers including luciferase, beta lactamase etc., may be utilized which allow for the selection of cells by FACS and related procedures. In an alternative embodiment, a separate plasmid may be constructed that comprises an antibiotic resistance gene, and can be used to co-transfect cells along with the subgenomic RNA molecules. Further, as described in detail in the following Examples, cells stably transfected with the subgenomic HCV RNA are grown in the appropriate medium for a selected period of time, the medium is then collected and analyzed for the presence of HCV RNA by dot blot hybridization or by conventional Northern hybridization, using a radioactively labeled probe having HCV DNA or RNA complementary sequences. Alternatively, viral gene products may be detected in the cells of the invention using conventional methods, including, without limitation, immunoassay and Western blotting.

Using the assays described above, stably-transfected cell lines can be selected which possess optimum characteristics for use in cell-based assays for screening potential anti-viral compounds.

Another aspect of the invention includes a non-human host animal which comprises the HCV expressing cells of the invention. These animals may be produced by administration of a HCV replicating cell, an HCV encoding nucleic acid having one or more adaptive mutations which permit replication in mice. The cells or viral nucleic acid could be directly injected intravenously (e.g. via tail vein injection), intramuscularly, subcutaneously, or via-intrahepatic injection. Alternatively, transgenic mice could be produced using the HCV replicons of the inventions, as described above.

III. Uses of Cell Lines for Cell-Based Assays of Potential Anti-HCV Agents

The human non-hepatic and murine hepatic cell lines of the invention which replicate HCV may be used in research, diagnostic, and therapeutic applications, including cell-based assays to evaluate the effectiveness of potential anti-HCV compounds, utilizing methodologies known in the art. Typical assays are summarized herein below. These cell-based assays may be performed in standard cell culture media utilizing commonly-available equipment, reagents and culture containers.

Persons skilled in the art will appreciate that these assays represent exemplary embodiments, and may be varied to provide similar/equivalent equipment or reaction conditions. For example, a variety of genes encoding antibiotic resistance are available, and can be utilized in accordance with the present invention in the generation of the cell lines of the invention. In a preferred embodiment, RNA isolated from parental human hepatic or untransformed cells is also utilized as a control in the assays described herein below to determine the effects of potential anti-viral compounds on HCV expressed in the cells. The control RNA is obtained in a manner similar to the HCV RNA. This cell line is treated in the assays described herein below as a negative control, to assure that any effects observed are due to the action of the compound being tested on HCV, and not non-specific effects due to the introduction of RNA into the cells.

A. General Cell-Based Assay for Inhibitors of HCV Replication 96-well microtiter plates are seeded with an appropriate amount of cells which replicate HCV in a standard cell culture medium containing G418 (e.g., 400 μg/ml), as well as standard concentrations of penicillin, streptomycin and kanamycin or gentamicin to prevent bacterial and mycoplasma contamination. The cells are incubated at 37° C. in a humidified 5% $CO_2$ incubator. On day 0 wells are washed three times with warm phosphate-buffered saline (PBS). The culture medium is then replaced with fresh medium containing 0.3% dimethylsulfoxide (DMSO), 10% fetal calf serum (FCS), penicillin, streptomycin, kanamycin/gentamicin, containing one of the following ingredients: (1) various concentrations of a known HCV inhibitor, such as interferon alpha, as a positive control; and (2) various concentrations of one or more of the compounds to be tested. The plates are incubated at 37° C. in humidified, 5% $CO_2$ incubator for 24, 48, and 72 hours. The plates are washed twice with PBS and then with a solution of methanol and acetone (1:1) to fix the cells. The cells are then incubated with an antibody specific for a viral protein (i.e. NS5A) according to the standard methods, such as enzyme linked immunosorbent assay (ELISA). Briefly, following incubation with the primary antibody, the plates are washed to remove unbound antibody and then incubated with a second, enzyme-conjugated antibody that can bind to the primary antibody. The plates are washed again, followed by an incubation with a colorless substrate that upon hydrolysis (cleavage) by the enzyme yields a colored product, the concentration of which can be determined with a spectrophotometer (microtiter plate reader). The concentration of the product corresponds to the levels of viral replication in cells and can be used to determine the activity of a given drug to inhibit HCV replication.

B. Cytotoxicity Assays

A cytotoxicity assay may be conducted to evaluate potential anti-HCV agents, utilizing a protocol similar to that described above. Instead of measuring HCV replication levels, however, cytotoxicity of the various test agents is assessed by standard procedures to determine cell viability, proliferation and levels of cellular metabolism including but not restricted to cell membrane permeability, lysosomal mass-pH, cell density or mitochondrial activity. For example, the CytoTox-ONE™ Assay from Promega is a rapid, fluorescent measure of the release of lactate dehydrogenase (LDH) from cells with a damaged membrane. LDH released into the culture medium is measured with a 10-minute coupled enzymatic assay that results in the conversion of resazurin into resorufin. Since the CytoTox-ONE™ Reagent mix does not damage healthy cells, released LDH can be measured directly in assay wells containing a mixed population of viable and damaged cells.

IV. Identification of Cell Lines Permissive for HCV Infection

As shown herein, it is possible to produce HCV carrying adaptive mutations that confer broad tissue and species tropism. Using such virus stocks it will be possible to screen cell lines of human and non-human origin for virus infection. Briefly, probes which correspond to unique portions of the sequence, may be used in detection methods. This method will lead to the identification of novel cell lines that are permissive for a complete cycle of HCV replication.

V. Screening for the HCV Receptor(s)

The ability to replicate HCV in different cell lines facilitates the isolation of the HCV receptor. Virus stocks similar to the ones described in section IV can be used to isolate the HCV receptor(s). For this purpose virus stocks carrying replicons with a selectable marker, such as neomycin or hygromycin will be used. Cells that are non-permissive for infection, will be transfected with DNA isolated from cells that are known to express the receptor (i.e. human hepatocytes, cells identified with the procedure described in section III) and subsequently infected with recombinant HCV carrying the selectable marker. Cells that express the receptor can then be selected through the addition of an antibiotic (i.e. G418 or hygromycin) to the culture medium. Once cells are identified, the transfected DNA can be isolated, cloned, and sequenced. The sequence information can then be used to identify the gene(s) encoded by transfected DNA.

The following examples are provided to describe the invention in further detail. These examples are intended to illustrate and not to limit the invention.

EXAMPLE I

Human Non-Hepatic and Mouse Hepatic Cell Lines that Replicate HCV

Materials and Methods

Cell culture. Cells were purchased from the American Type Culture Collection (BHK Kidney *Mesocricetus auratus* (Syrian golden hamster) ATCC CRL-1632; Vero Kidney epithelial *Cercopithecus aethiops* (African green monkey) ATCC CCL-81; CV-1 Kidney fibroblast *Cercopithecus aethiops* (African green monkey) ATCC CCL-70; HT1080 Fibrosarcoma *Homo sapiens* (human) ATCC CRL12012; HeLa Cervix carcinoma *Homo sapiens* (human) ATCC CCL2; McA-RH7777 Hepatoma *Rattus norvegicus* (rat) ATCC CRL-1601; FTO2B Hepatoma *Rattus norvegicus* (rat); Hepa1-6 Hepatoma *Mus musculus* (mouse) ATCC CRL-1830; AML12 Hepatocyte *Mus musculus* (mouse) ATCC CRL-2254; FL83B Hepatocyte *Mus musculus* (mouse) ATCC CRL-2390). The Huh7-derived cell lines GS4.1 and GS4.5 are subclones derived from cell lines FCA1 and FCA4, respectively (Guo, J. T., et al., 2001., J. Virol. 75:8516-8523). Cell line Bsp8 is a Huh7-derived cell line expressing HCV-N subgenomic replicon 1bneoΔS (Guo, J. T., et al., 2001., J. Virol. 75:8516-8523). All cultures were grown in Dulbecco's modified Eagle's medium (Gibco-Invitrogen) supplemented with 10% fetal bovine serum, L-glutamine, nonessential amino acids, penicillin, and streptomycin.

RNA transfection. All the plasmids were linearized with ScaI, and RNA was synthesized with the MEGAscript kit (Ambion). In vitro-transcribed RNA was purified as previously described (Guo, J. T., et al., 2001., J. Virol. 75:8516-8523). Total cellular RNA was extracted with Trizol reagent (Invitrogen). The conditions used for the transfection of cells with total RNA were identical to those used for the transfection with in vitro-transcribed RNA (Guo, J. T., et al., 2001., J. Virol. 75:8516-8523). Colonies were selected with G418 at a concentration of 1 mg/ml.

RNA analysis. Total cellular RNA was extracted from transfected cell lines with Trizol reagent. Five micrograms of total RNA was fractionated on 1% agarose gels containing 2.2 M formaldehyde and transferred onto a nylon membrane. Membranes were hybridized with riboprobes specific for plus-stranded HCV replicon RNA, human papillomavirus (HPV) E6, and mouse albumin mRNA as described previously (Guo, J. T., et al., 2001., J. Virol. 75:8516-8523). The HPV and mouse albumin probes spanned nucleotides 811 to 1491 (GenBank accession number M20325) and nucleotides 1501 to 1988 (GenBank accession number XM_132149), respectively.

Reverse transcription-PCR and DNA sequencing. Nucleotide and amino acid numbers correspond to the HCV type 1b genome Con-1 (AJ238799). HCV replicons were isolated and cloned from established cell lines by PCR amplification of three fragments spanning the entire NS region from position 3420 to 9410. The untranslated regions at the 5' and 3' ends of HCV RNA were cloned separately for nucleotide sequence analysis. DNA synthesis was carried out with Superscript II reverse transcriptase provided in a cDNA synthesis kit (Gibco-Invitrogen). The DNA oligomers used as primers for the reverse transcription reaction mapped to positions 485 to 465, 5492 to 5473, 7256 to 7234, 9410 to 9388, and 9616 to 9597. The reaction mixtures were incubated for 1 h at 45° C. PCR was performed with an Advantage PCR kit (Clontech). One microliter of the cDNA reaction mixture was used for PCRs with 19- to 23-nucleotide-long primers that yielded fragments spanning positions 1 to 464, 1387E to 5082, 5016 to 7226, 7154 to 9387, and 9239 to 9616. Position 1387E refers to an oligomer specific for the encephalomyocarditis virus (EMCV) internal ribosome entry site (IRES) element located upstream of NS3. The PCR products were cloned into plasmid pGEM-T Easy (Promega). Four clones of each fragment were sequenced with an ABI automatic DNA sequencer, and a consensus sequence was established with the help of a sequence assembly program (Genetics Computer Group).

Long reverse transcription-PCR was performed with an Advantage-GC kit (Clontech) with a pair of primers beginning at positions 1415E, upstream of NS3, and 7989 within NS5B. The PCR conditions were modified as follows: step 1, 95° C. for 3 min; step 2, 5 cycles, 30 s at 95° C. and 6 min at 72° C.; step 3, 27 cycles, 30 s at 95° C. and 6 min at 68° C.; step 4, 68° C. for 6 min. PCR products were gel purified and digested with HindIII and MfeI and replaced with the corresponding fragment in plasmid I377/NS3-3'.

Plasmid construction. All plasmids (Table 3) were derived from the parental HCV Con-1 replicon I377/NS3-3' (AJ242652). Subgenomes containing consensus mutations were constructed by replacing DNA restriction fragments with the corresponding fragments from the pGEM-T Easy cDNA libraries (see above). The resulting plasmids with the amino acid changes in the NS region are listed in Table 3.

Immunofluorescence. Cells were plated on coverslips in six-well plates at least 16 h before treatment, washed with phosphate-buffered saline, and fixed with cold methanol-acetone (1:1) for 15 to 20 min. Next, the cells were blocked in phosphate-buffered saline containing 10% fetal bovine serum for 30 min at room temperature and then incubated with anti-NS5A antibodies (a gift from Chen Liu) and fluorescein isothiocyanate-conjugated goat anti-mouse immunoglobulin antibodies (Jackson Laboratories). In addition, cells were stained with the DNA binding fluorochrome DAPI (4',6'-diamidino-2-phenylindole). Coverslips were mounted with antifade agent (Molecular Probes), examined with a Nikon immunofluorescence microscope, and photographed with a charge-coupled device camera.

Results

HCV Replication in Cells of Nonhepatic Origin.

HCV exhibits a very narrow host range and infects only humans and chimpanzees. We question whether this limitation was due to determinants of RNA replication. Because efficient replication of subgenomes depends on genetic adaptations of the replicon (Blight, K. J., et al. 2000. Science 290:1972-1975; Guo, J. T., et al., 2001., J. Virol. 75:8516-8523; Lohmann, V., et al., 2001. J. Virol. 75:1437-1449), presumably to compensate for subtle variations in the cellular environments among cells from different tissues, it was hypothesized that replication in cells of nonhepatic origin would require additional, cell-type-specific adaptive mutations. Transfection of several primate- and rodent-derived cell lines with subgenomic RNA transcribed from plasmid DNA carrying previously identified adaptive mutations in Huh7 cells did not yield cell lines expressing replicons. To increase the chance for the selection of RNA subgenomes capable of replicating in cells of nonhepatic origin, subgenomic RNA isolated from Huh7 cell lines that replicate HCV RNA was used. Because of the high rate of nucleotide incorporation errors that occur during RNA-directed RNA synthesis, this population of viral subgenomes exhibited much greater genetic heterogeneity than did RNA transcribed from a DNA template in vitro.

Upon transfection of HeLa cells with total RNA obtained from Huh7 cell lines GS4.1, GS4.5, and Bsp8, G418-resistant cell clones were obtained. The number of clones ranged from approximately 2 (Bsp8) to 50 (GS4.1) per 10 μg of total RNA depending on the origin of the RNA used for the transfections. Replicons in these three Huh7-derived cell lines contained different adaptive mutations and replicated two different HCV 1b genomes (Guo, J. T., et al., 2001., J. Virol. 75:8516-8523). Several HeLa-derived colonies obtained with total RNA from GS4.1 cells were subsequently expanded into seven stable cell lines (SL1 to SL7; FIG. 1A, lanes 4 and 8 to 12). The amounts of viral RNA present in early passages of these cell lines examined ranged from 0.05 to 7.5 ng/10 μg of total RNA, which corresponded to 20 to 3,000 copies of RNA per cell. In general, the amounts of RNA increased upon passage of cells and reached levels that were comparable to those obtained with the most productive Huh7-derived cell lines such as GS4.1 (lanes 2 and 4 to 6). As expected, expression of viral gene products could be confirmed by immunofluorescence with antibodies directed against NS5A (FIG. 1B). As with GS4.1 cells, more than 90% of SL1 cells expressed viral proteins. However, in contrast to Huh7 cell lines where the accumulation of HCV RNA declines approximately 100-fold when cells become confluent, viral replication in HeLa cells was not affected by the growth conditions of the cells, i.e., SL1 cells continued to produce high amounts of viral RNA even when they became confluent (results not shown) (Guo, J. T., et al., 2001., J. Virol. 75:8516-8523; Pietschmann, T., et al. 2001. J. Virol. 75:1252-1264).

Adaptation of HCV Replicons.

Figure 2:
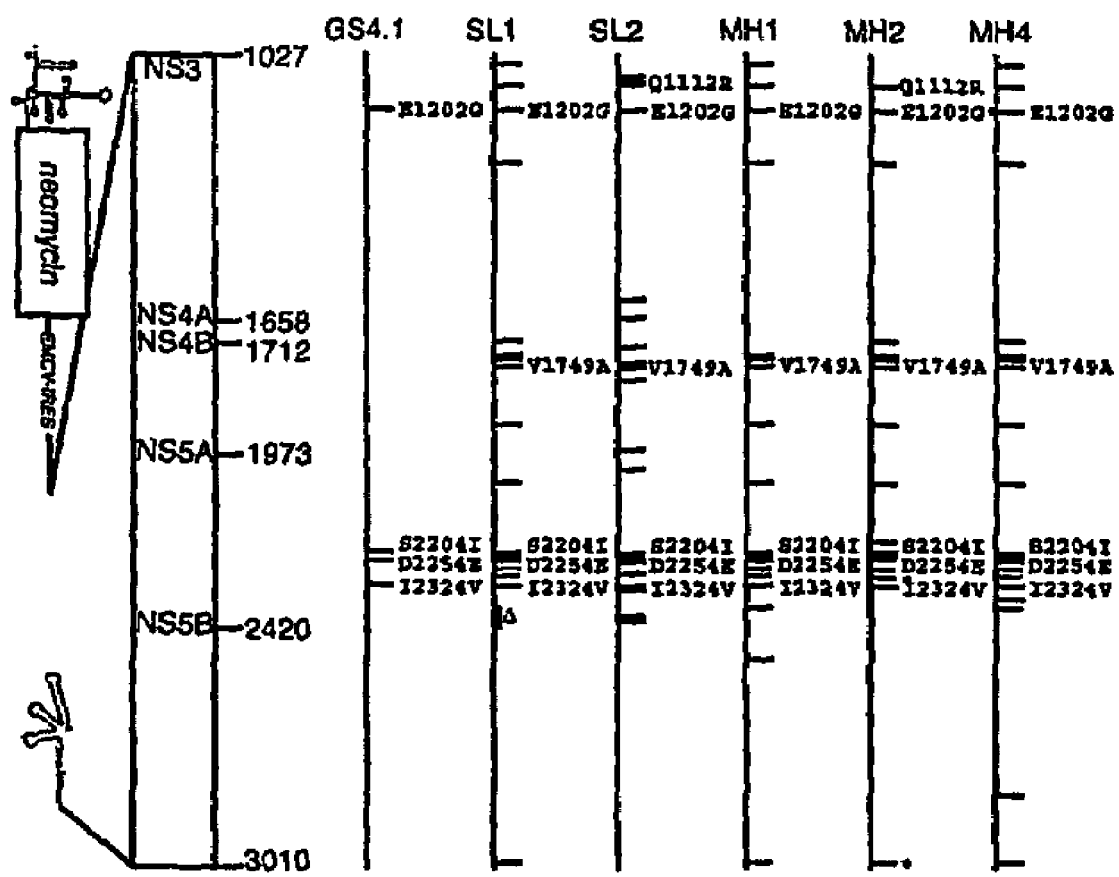

To determine whether HCV replication in HeLa cells led to the selection of subgenomes with cell-type-specific adaptive mutations, the efficiency by which G418-resistant colonies formed in Huh7 and HeLa cells transfected with total RNA isolated from GS4.1 and SL1 cells was compared. Total RNA from GS4.1 cells led to the selection of approximately 166 G418-resistant colonies per ng of viral RNA in Huh7 cells compared with only 4 colonies in HeLa cells (Table 1). In contrast, total RNA from SL1 cells yielded 160 colonies in HeLa cells compared with about 20 in Huh7 cells. These results indicated that replication in HeLa cells led to the selection of variants with cell-type-specific adaptive mutations that were responsible for the 40-fold increase in colony formation efficiency between amplified RNA in GS4.1 and SL1 cells. Nucleotide sequence analysis of HCV cDNA clones obtained from the SL1 and SL2 cell lines confirmed this view. These data showed that replicons in the two HeLa cell lines maintained the previously identified adaptive mutations in GS4.1 cells and acquired several additional mutations that resulted in amino acid changes in the NS region (FIG. 2 and Table 2). Notably, some of the new mutations formed clusters in the NS4B and NS5A regions. In the case of SL1 cells, a deletion of 43 amino acids near the C terminus of NS5A was observed. Of particular interest were mutations in the amino-terminal region of NS4B, because they have so far not been found in cDNAs from replicons in Huh7 cells and hence could have been responsible for the observed adaptation of replicating RNA (Blight, K. J., et al. 2000. Science 290:1972-1975; Guo, J. T., et al., 2001., J. Virol. 75:8516-8523; Krieger, N., et al., 2001. J. Virol. 75:4614-4624; Lohmann, V., et al., 2001. J. Virol. 75:1437-1449). Moreover, one mutation at position 1749 was present in both SL1 and SL2 cells. In contrast to the results obtained with the NS regions, no mutations were detected in the 5' and 3' untranslated regions of replicons expressed in SL1 and SL2 cells.

TABLE 2

Consensus mutations in replicons isolated from HeLa and mouse hepatoma cell clones

| Cell clone | Conserved mutation(s) | NS protein |
|---|---|---|
| GS4.1 | E1202G | NS3 |
|  | S2204I, D2254E, I2324V | NS5A |
| SL1 | Q1067R, S1128A, E1202G, S1323P, S1560G[a] | NS3 |
|  | L1701F | NS4A |
|  | Q1720R, Q1727H, V1749A, V1893L | NS4B |
|  | T2035A, S2204I, I2252V, D2254E, I2274V, R2290L, I2324V, del.2371-2413[b] | NS5A |
|  | W2990R | NS5B |
| SL2 | I1097V, Q1112R, P1115L, V1593M, M1647I | NS3 |
|  | L1715P, Q1737R, V1749A, I1797V, N1965Y | NS4B |
|  | Q2012L, S2204I, E2247G, D2254E, K2302R, I2324V, S2336P, L2400S, E2411G, A2412V | NS5A |
| MH1 | Q1067R, S1128A, E1202G, S1323P, S1560G | NS3 |
|  | Q1720R, Q1727H, V1749A, V1893L | NS4B |
|  | T2035A, S2204I, I2252V, D2254E, I2274V, R2290L, I2324V, M2388T, T2496A | NS5A |
|  | W2990R | NS5B |
| MH2 | Q1112R, E1202G,[a] S1323P, S1560G | NS3 |
|  | L1701F | NS4A |
|  | Q1720R, Q1727H, V1749A, V1893L | NS4B |
|  | T2035A, T2185A, S2204I, I2252V, D2254E, I2274V, R2290[a], I2324V[a] | NS5A |
|  | W2990R[a] | NS5B |
| MH4 | Q1067R, S1128A, E1202G, S1323P, S1560G | NS3 |
|  | L1701F | NS4A |
|  | Q1720R, Q1727H, V1749A, V1893L, A1841T | NS4B |
|  | T2035A, S2204I, I2252V, D2254E, I2274V, R2290L, I2324V, T2364M, L2391R | NS5A |
|  | I2843V, W2990R | NS5B |

[a]Mutation that occurred in 50% of the clones analyzed.
[b]del., deletion.

Mouse Hepatoma Cells can Support HCV RNA Replication.

Figure 3A:
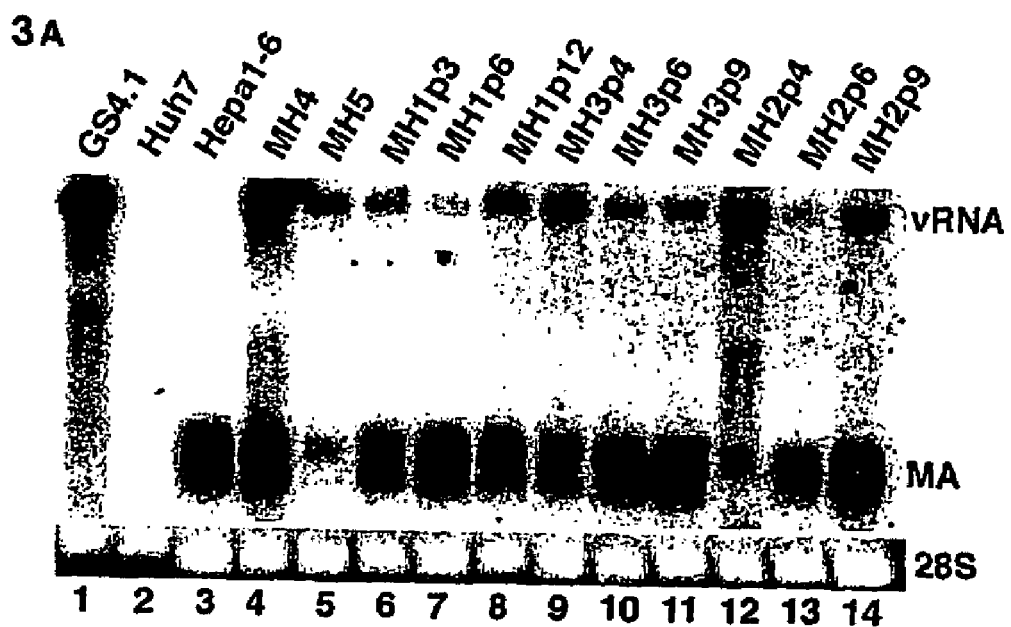

The discovery of several additional mutations in cDNA clones obtained from SL1 and SL2 cells suggested total RNA from these cell lines might yield colonies in cells that did not appear to be permissive for HCV replication after transfection with subgenomic RNA or total RNA from Huh7-derived cell lines. Hepatoma and hepatocyte-derived cell lines were examined. G418-resistant colonies were obtained with the mouse hepatoma cell line Hepa1-6 after transfection with total RNA from SL1 cells (FIG. 3A, lanes 4 to 6, 9, and 12).

TABLE 1

Colony formation efficiency of total cellular RNA[a].

| | | No. of colonies in transfected cells | | | | | | |
|---|---|---|---|---|---|---|---|---|
| | | Huh7 | | | HeLa | | | Hepa1-6 | | |
| Cell | Viral RNA (ng/10 µg) | Mean | (SD) | Colonies/ng of viral RNA | Mean | (SD) | Colonies/ng of viral RNA | Mean | (SD) | Colonies/ng of viral RNA |
| GS4.1 | 5 | 834 | (64) | 166 | 22 | (4) | 4 | 0 | | <1 |
| SL1 | 5 | 100 | (53) | 20 | 803 | (81) | 160 | 1.3 | (1.5) | <1 |
| MH1 | 0.5 | 20 | (2) | 40 | 66 | (9) | 132 | 1.7 | (0.6) | 3 |

[a]Results from three independent transfection experiments. Total RNA was extracted from GS4.1, SL1, and MH1 cells at passages 21, 26, and 4, respectively.

Figure 3B:
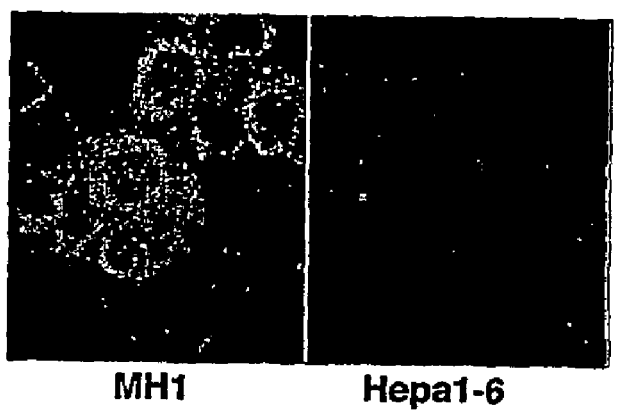

As with HeLa cells, the amounts of RNA ranged from 300 to 1,000 copies of RNA per cell and a large fraction of the cells expressed viral proteins (FIG. 3B). In contrast to Huh7 and HeLa cells, the amount of HCV RNA in the mouse cell lines appeared to vary between cell passages (FIG. 3A, lanes 6 to 14). Interestingly, total RNA isolated from one of the mouse cell lines, MH1, did not produce significantly more colonies in Hepa1-6 cells than did total RNA from SL1 cells, suggesting that the subgenomes present in SL1 cells were already adapted for replication in the mouse cells (Table 1). In support of this interpretation, nucleotide sequence analysis of viral cDNAs cloned from three mouse cell lines showed that the majority of the mutations identified in SL1 cells were maintained (FIG. 2). Surprisingly, the deletion in NS5A identified in four of four clones sequenced from SL1 cells was not present in replicons isolated from mouse cells, indicating that a subpopulation of replicons without the deletion was still present in these (SL1) cells.

Figure 4:
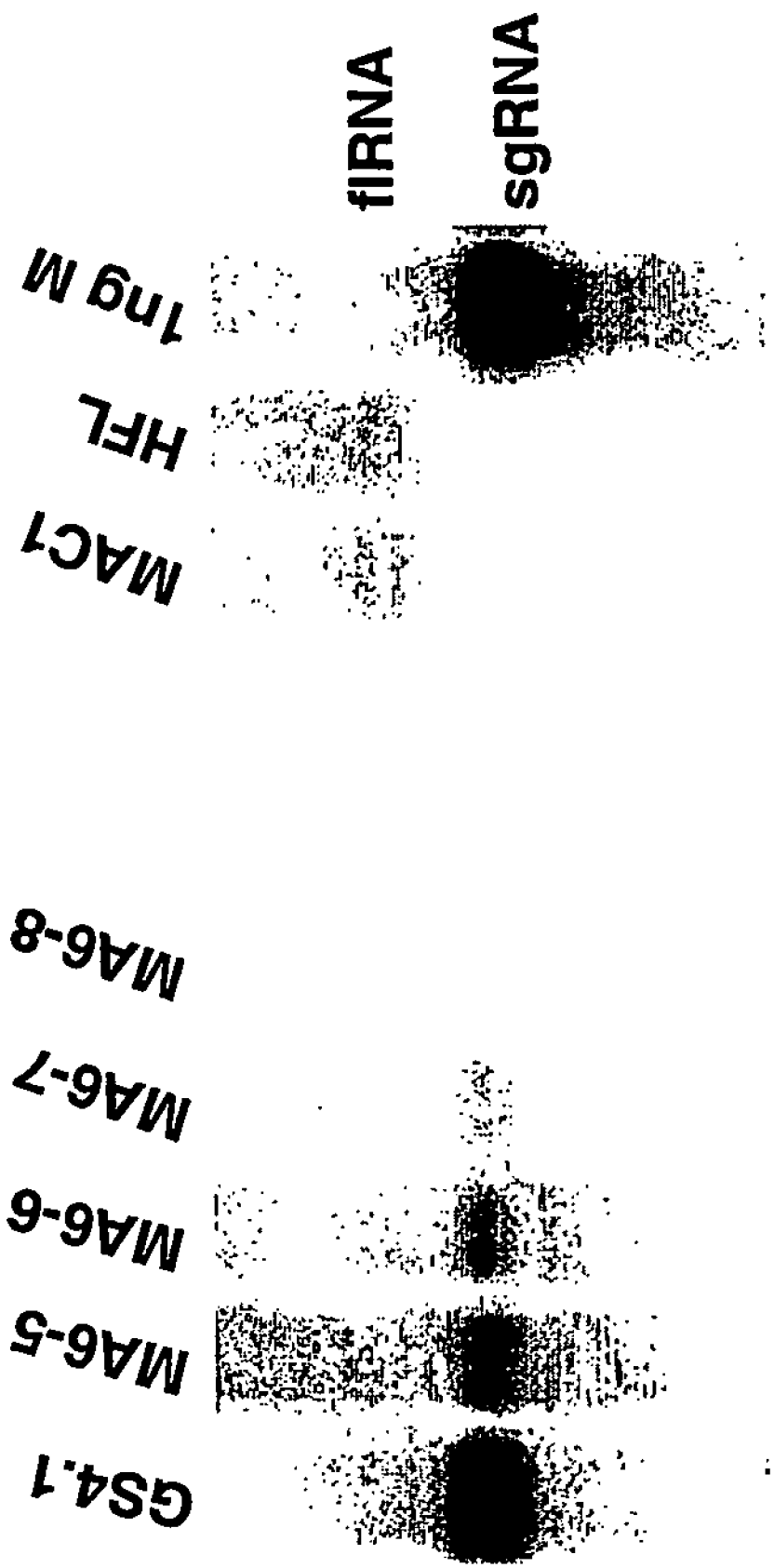

In further experiments, mouse hepatocyte cells AML12 (ATCC CRL-2254) were transfected with total RNA isolated from the cell line GS4.1, expressing subgenomic replicons and from cell line HFL expressing full-length HCV genomes, respectively. G418 resistant colonies were isolated to establish stable cell lines expressing HCV suggenomic and full-length replicons. 5 micrograms of total RNA was isolated from AML12 cell lines (MA6-5 to MA6-8, and MAC1) that were established from G418 resistant cell colonies and analyzed by Northern blot analysis, which confirmed replication of HCV (FIG. 4).

Cell-derived HCV RNA is more Efficient than in Vitro-transcribed RNA in Initiating Replication in HeLa and Mouse Hepatoma Cells.

Results showed that replication of HCV subgenomes in HeLa and mouse cells led to the selection of replicons with several novel mutations. The majority of these mutations were located in the NS3, NS4B, and NS5A regions. Moreover, the results showed that cell-derived RNA carrying some or all of these mutations was much more efficient in establishing G418-resistant colonies in HeLa cells than was RNA derived from Huh7 cells (Table 1).

Based on these observations, it was surmised that introduction of these mutations into available subgenomic replicons should alter or expand their tissue and host tropism. To test this hypothesis, 13 subgenomic replicons were designed that carried mutations in NS3, NS4B, and NS5A alone or in combination with each other as described in Table 3. Of the 13 constructs examined, only two, pZS2 and pZS25, yielded a small number of G418-resistant colonies in HeLa cells (Table 4). Viral RNA replication was confirmed by Northern blot analysis of total RNA isolated from six cell lines derived from those colonies. None of the variants yielded colonies in Hepa1-6 cells. Moreover, negative-control experiments with in vitro-transcribed RNA derived from a variant containing a frameshift mutation in NS5B did not yield any colonies that could be expanded into cell lines. Notably, save for one, all replicons were permissive for replication in Huh7 cells, albeit with significantly different efficiencies (Table 3). Interestingly, both pZS2 and pZS25 carried mutations in NS4B that were conserved in replicons from two independent HeLa cell lines, SL1 and SL2. In addition, these replicons had the S2204I mutation in NS5A that was previously found to be one of the most potent adaptive mutations for HCV replication in Huh7 cells. Because both replicons replicated very efficiently in Huh7 cells, the results suggested that the NS4B mutations could have contributed to the observed expansion of the tissue tropism of HCV replicons. In support of this hypothesis, the subgenome with the highest efficiency in Huh7 cells, pZS11 lacking mutations in NS4B (Table 3), did not yield any colonies in HeLa cells.

TABLE 3

Colony formation efficiency of mutant replicons in Huh7 cells

| Vector[i] | Conserved mutation(s) | Mean (SD) CFE/ μg of RNA[g] | NS protein(s) affected |
|---|---|---|---|
| $I_{377}$/NS3-3' | NA[h] | 2.3 (1.5) | NA |
| pZS10 | A1[a] | 3.3 (3.5) | NS3 |
| pZS1 | C1[b] | $1.4 \times 10^3$ ($3.9 \times 10^2$) | NS5A |
| pZS20 | B[c] | 1.7 (0.6) | NS4AB |
| pZS11 | A1 + C1 | $2.4 \times 10^5$ ($7 \times 10^4$) | NS3, NS5A |
| pZS2 | B + C1 | $7.8 \times 10^4$ ($1.7 \times 10^4$) | NS4AB, NS5A |
| pZS12 | A1 + B | 0.3 (0.6) | NS3, NS4AB |
| pZS5 | A1 + B + C1 | 15 | NS3, NS4AB, NS5A |
| pZS4 | B + C1 + A2[d] | 165 (21) | NS3, NS4AB, NS5A |
| pZS8 | A2 + B | 0 | NS3, NS4AB |
| pZS6 | A2 + B + C2[e] | 8 (4) | NS3, NS4AB, NS5A |
| pZS15 | C3[f] | 491 (183) | NS5A |
| pZS25 | B + C3 | $1.7 \times 10^4$ ($2.6 \times 10^3$) | NS4AB, NS5A |
| pZS45 | A2 + B + C3 | 19 (2) | NS3, NS4AB, NS5A |

[a]A1, mutation E1202G.
[b]C1, mutations S2204I and D2254E.
[c]B, mutations L1701F, Q1720R, Q1727H, and V1749A.
[d]A2, mutations E1202G, S1128A, and S1323P.
[e]C2, mutations S2204I, D2254E, R2290I, and I2324R.
[f]C3, all the mutations of C2 plus the deletion 2371-2413.
[g]CFE, colony formation efficiency. Values are derived from three independent transfections of each replicon RNA.
[h]NA, not applicable.
[i]Sequence ID Numbers for subgenomic replicons are listed in Table 6

TABLE 4

Colony formation efficiency of in vitro-transcribed RNA[a]

| Source of cDNA library (cell line or plasmid) | No. of colonies in transfected cells | | |
|---|---|---|---|
| | Huh7 | HeLa | Hepa1-6 |
| GS4.1 | >10,000 | 0, 0, 0 | 0, 1, 0 |
| SL1 | >10,000 | 0, 3, 2 | 0, 1, 0 |
| MH4 | >10,000 | 3, 4, 0 | 17, 0, 0 |
| pZS2 | >10,000 | 2, 3, 0 | 0, 0, 0 |
| pZS25 | >10,000 | 0, 2, 1 | 0, 0, 0 |

[a]Results from transfection experiments with in vitro-transcribed RNA from pooled clones isolated from the indicated cell line and from in vitro-transcribed RNA from pZS2 and pZS25 (Table 3).

To further explore the basis for the observed low colony formation efficiency of in vitro-transcribed RNA in HeLa cells, it was determined if replication in HeLa cells led to the selection of adaptive mutations that were not discovered previously when cDNA clones from SL1 and SL2 cells were sequenced. For this purpose, cDNA clones were isolated from total RNA obtained with pZS2- and pZS25-derived cell lines, respectively. Nucleotide sequence analysis of both cDNA clones did not reveal any additional consensus mutations, suggesting that the two subgenomes were sufficiently adapted for replication in HeLa cells (results not shown). However, as mentioned above, it was possible that a minor population of subgenomic replicons with additional mutations were present in these cell lines. To overcome this problem, a method for the isolation and cloning of cDNAs spanning the NS3 to NS5B region was developed (see Materials and Methods). Replicon cDNA libraries were produced from GS4.1, SL1, and MH4 cells. Approximately 2,000 cDNA clones were pooled and subsequently used for in vitro transcription of subgenomic RNA. With Huh7 cells, the colony formation efficiency of the pooled clones was comparable to that of the most efficient subgenomes, such as pZS2 or pZS25, and did not vary significantly with the origin of the total RNA used for cDNA cloning (Table 4). Consistent with previous results, colony formation in HeLa and mouse cells was origin dependent, i.e., save for one case, colonies were observed only with clones derived from SL1 and MH4 cell lines. Notably, with this strategy G418-resistant colonies were obtained for the first time with Hepa1-6 cells by using in vitro-transcribed RNA. To confirm the presence of viral RNA, 11 colonies were expanded and Northern blot analysis was performed with total RNA. All 11 RNA samples analyzed contained viral RNA ranging from approximately 0.1 to 1 ng/5 µg of total RNA (results not shown).

Taken together, the results supported the hypothesis that mutations identified in subgenomic replicons expressed in HeLa and mouse cells play a role in adaptation of the replicons to certain cell-type-specific conditions.

Discussion

HCV is known as a species- and tissue-specific virus. The results described herein show that replication of HCV can occur in cells derived from tissues other than liver, indicating that cellular factors required for RNA replication are expressed in cell types other than hepatocytes. One interpretation of this result is that the apparent tropism of HCV for hepatocytes is determined primarily at the level of virus entry or assembly or, alternatively, that HCV can infect many other tissues but has escaped detection due to very low amounts of RNA replication or accumulation. Extrahepatic tissues could serve as reservoirs for HCV that, as with human immunodeficiency virus, could provide a source of viruses that are refractory to antiviral therapy and, importantly, can be responsible for infection of liver grafts following orthotopic liver transplantation (Chun, T. W., et al., 2002. J. Infect. Dis. 185:1672-1676; Laskus, T., et al., 2002. J. Infect. Dis. 185: 417-421). Such a scenario would have profound implications for antiviral therapy. For example, the targeting of drugs to secondary sites of viral replication and the analysis of drug metabolism in cells other than hepatocytes would become important factors for the development of successful antiviral therapies.

It is conceivable that HCV quasispecies in hepatocytes and other tissues exhibit differences in their composition due to the selection of variants with cell-type-specific adaptations. As shown in this Example, replication of subgenomes in HeLa cells led to the accumulation of clusters of mutations in the NS3, NS4B, and NS5A regions including a deletion in NS5A (FIG. 2). Mutations and deletions in NS5A have been found previously in genomes that replicated in Huh7 cells, which could suggest that expression of the natural form of this protein in cell culture somehow interferes with RNA replication (Blight, K. J., et al. 2000. Science 290:1972-1975; Guo, J. T., et al., 2001., J. Virol. 75:8516-8523; Ikeda, M., et al., 2002. J. Virol. 76:2997-3006; Lohmann, V., et al., 2003. J. Virol. 77:3007-3019; Lohmann, V., et al., 2001. J. Virol. 75:1437-1449). However, mutations in the amino terminus of NS4B have previously not been observed. Notably, in both SL1 and SL2 cells, the mutations changed two or one glutamine residues, respectively, to one of the two basic amino acids arginine and histidine. Moreover, the mutation V1749A was present in all five cell lines examined (Table 2 and FIG. 2). Thus far, these results show that these mutations appear to be required for replication in HeLa cells, because only replicons pZS2 and pZS25 carrying these mutations yielded colonies after transfection with in vitro-transcribed RNA (Tables 3 and 4). The amino terminus of NS4B is predicted to reside on the cytoplasmic side of endoplasmic reticulum membranes and may interact with other host or viral proteins required for RNA replication (Hugle, T., et al., 2001. Virology 284:70-81). As an integral endoplasmic reticulum membrane protein, NS4B might provide a scaffold for the assembly of replication complexes and act as a regulator for RNA replication. More importantly, a recent study revealed that NS4B can induce particular membrane structures, called membranous webs, proposed to be the site for HCV replication (Egger, D., et al., 2002. J. Virol. 76:5974-5984). Interestingly, genetic analyses with an HCV-related pestivirus identified the amino-terminal region of NS4B as a determinant for cytotoxicity caused by high levels of virus replication (Qu, L., et al., 2001. J. Virol. 75:10651-10662).

In summary, this example demonstrates that HCV RNA replication is not restricted to the human hepatoma cell line Huh7 but instead occurs in HeLa cells and hepatoma cells derived from mice. These findings further facilitate development of a mouse model for HCV infection.

EXAMPLE II

RNA Polymerase Inhibitors Inhibit HCV Replication in Transformed HeLa Cells

Figures 5A, 5B:
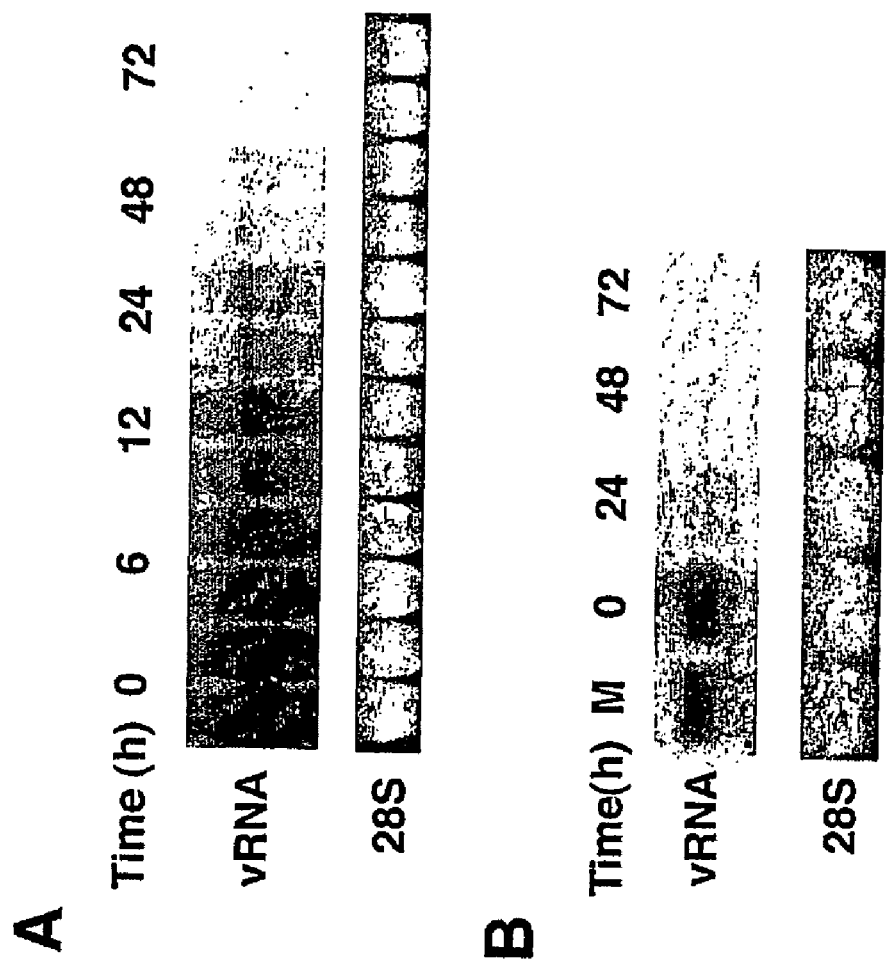

In this example, the anti-HCV activity of 2'-C-methyladenosine (2CMA, an HCV RNA polymerase inhibitor) was tested on GS4.1 (Huh7) cells, and SL1 (HeLa). The cells were treated with 10 µM 2CMA. The cells were harvested at 6, 12, 24, 48, and 72 hours. Total cellular RNA was extracted and viral RNA (vRNA) analyzed by Northern blot analysis. These results indicate that 2CMA effectively inhibits HCV in GS4.1 and SL1 cells (FIG. 5).

Figure 6A:
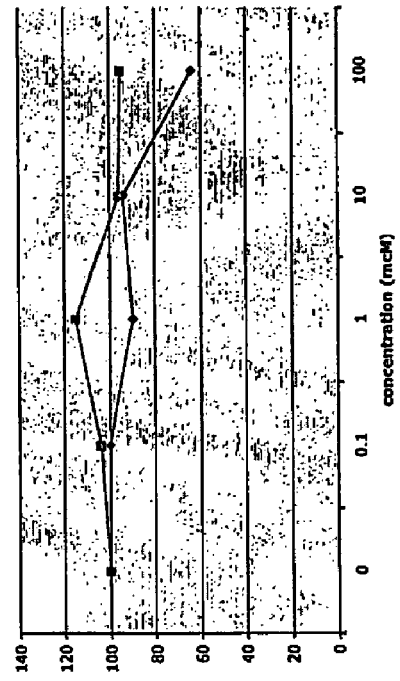
Figure 6B:
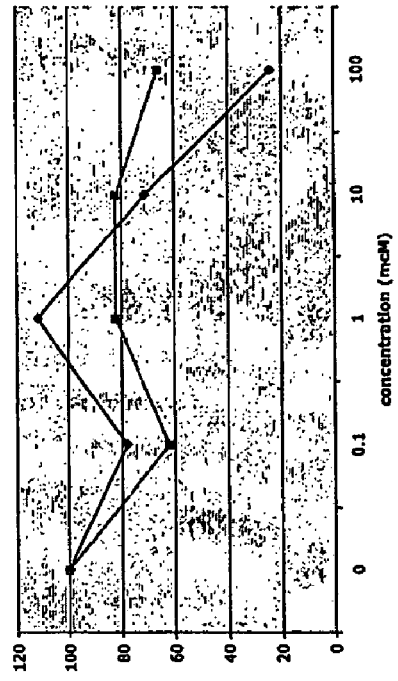

Next, the antiviral activity of the HCV RNA polymerase inhibitor 5-OH-cytidine was tested. GS4.1 (Huh7) cells and SL1 (HeLa cells were treated with the indicated amounts of 5-OH-cytidine. The DNA polymerase inhibitor 5-OH-deoxycytidine was used as a negative control. The cells were harvested 72 hours after incubation with the drugs. Total cellular RNA was extracted and viral RNA analyzed by Northern blot analysis. The intensity of the bands corresponding to HCV RNA was determined with a Fuji phosphoimager. These results indicate that 5-OH-cytidine effectively inhibits HCV replication in GS4.1 and SL1 cells (FIG. 6).

EXAMPLE III

Cytopathic and NonCytoPathic Responses in Cells Expressing Hepatitis C Virus Currently, combination treatment with alpha-interferon and ribavirin is the therapy of choice for HCV infection. But this treatment is not always effective, and other treatment choices are limited, or have unproven efficacy. Study of the mechanism of action of IFN-α may help elucidate a new, effective treatment for HCV, or help determine what makes HCV treatment effective.

DNA microarray studies revealed that the antiviral response induced by IFNs alters the expression of hundreds of genes and, hence, is far more complex than previously anticipated (Der, S. D., et al., 1998. Proc. Natl. Acad. Sci. USA 95:15623-15628). Little is known about the nature of the cellular proteins that specifically target viral components and, hence, are responsible for the inhibition of viral replication in the absence of cell death. In contrast, the major signal transduction pathways required for the innate immune response against many viruses have been elucidated. The first wave of IFN-induced genes depends on the phosphorylation of STAT1 and STAT2 and their interaction with IRF9 (p48) to form the transcription factor complex ISGF3. In addition, viral double stranded RNA (dsRNA) and other unknown viral factors are believed to play an important role in the establishment of an antiviral state. They can activate dsRNA-dependent enzymes such as protein kinase R (PKR) and 2',5'-oligoadenylate synthase (OAS), as well as other still-elusive protein kinases (Smith, E. J., et al., 2001. J. Biol. Chem. 276:8951-8957). IFN-α can induce a noncytopathic antiviral response or, alternatively, trigger apoptotic programs leading to the elimination of infected cells (Tanaka, N., et al., 1998. Genes Cells 3:29-37).

Nucleotide sequence analyses of HCV genomes isolated from Japanese patients revealed a correlation between the presence of mutations in a short segment of NS5A, termed the IFN sensitivity-determining region (ISDR), and resistance to antiviral therapy with IFN-α (Enomoto, N., et al., 1995. J. Clin. Investig. 96:224-230; Enomoto, N., et al., 1996. N. Engl. J. Med. 334:77-81). Subsequently, it was reported that the ISDR motif can bind to PKR (Gale, M. J., Jr., et al., 1997. Virology 230:217-227). Importantly, the ISDR from IFN-resistant, but not from IFN-sensitive, HCV isolates appeared to be a substrate for PKR, suggesting that IFN treatment of chronically infected patients can lead to the selection of HCV variants with ISDRs that can bind and inactivate PKR (Gale, M. J., Jr., et al., 1998. Clin. Diagn. Virol. 10:157-162; Tan, S. L., and M. G. Katze. 2001. Virology 284:1-12).

Accordingly, study of HCV variants and the pathway by which IFN inhibits HCV is necessary to provide new HCV treatments, and to prevent selection of IFN-α resistant variants.

Materials and Methods

Chemicals and reagents. Recombinant IFN-α2b (intron A) was purchased from Schering-Plough. Cycloheximide, 2-aminopurine (2-AP), genistein, sodium salicylate, and wortmannin were obtained from Sigma. SB 203580, PD 98059, vanadate, PP2, rapamycin, and lactacystin were obtained from Calbiochem. Epoxomicin was obtained from Boston Biochem, and caspase inhibitor ZVAD-fluoromethyl ketone (ZVAD-FMK) was obtained from Enzyme Systems Products.

Cell culture. Huh7 and HeLa cells were maintained in Dulbecco's modified Eagle's medium supplemented with 10% fetal bovine serum, penicillin G, streptomycin, nonessential amino acids, and L-glutamine. For the cell lines carrying HCV and Kunjin virus replicons, 500 µg of G418/ml was added to the medium. The GS4.1 cell line was derived from a subclone of FCA1 cells as described previously (Guo, J. T., et al., 2001. J. Virol. 75:8516-8523). SL1 is a HeLa cell line expressing HCV subgenomic replicon $I_{377}$NS3-3' (Lohmann, V., et al., 1999. Science 285:110-113; Zhu, Q., et al., 2003. J. Virol. 77:9204-9210). The KUNCD20 cells represent a pool of approximately 200 colonies of G418-resistant HeLa cells obtained after transfection with the Kunjin virus replicon C20DXrepNeo RNA (Khromykh, A. A., and E. G. Westaway. 1997. J. Virol. 71:1497-1505) (kindly provided by A. Khromykh, Sir Albert Sakzewski Virus Research Center, Brisbane, Australia).

Plasmids. pCMV-E3L expressing the vaccinia virus E3L protein was obtained from Robert Schneider, New York University, New York. pln035 expressing virus-associated (VA) RNA was obtained from David Lazinski, Tufts University, Boston, Mass. pEF-HA-HPIV2 expressing the V protein of human parainfluenzavirus 2 (HPIV2) was obtained from Curt Horvath, Mount Sinai School of Medicine, New York, N.Y. To obtain cDNA clones of the gene encoding human Mx-1, Huh7 cells were treated with 100 IU of IFN-α/ml for 6 h and total cellular RNA was extracted with TRIzol reagent (Invitrogen) and first-strand cDNA was made with an oligo(dT)$_{12-18}$ primer and Superscript II DNA polymerase (Invitrogen) by following the manufacturer's direction. For the amplification of Mx-A cDNA, the primers used were 5'-AGTATCGTGG-TAGAGAGCTGC-3' (SEQ ID NO:15) and 5'-TAATAC-GACTCACTATAGGGATGTGGCTGGAGATGC-3' (SEQ ID NO:16). The purified PCR fragment was cloned into the pGEM-T Easy vector (Promega). The identity of the cloned fragment was verified by nucleotide sequence analysis.

RNA extraction and Northern blot hybridization. Total cellular RNA was extracted with TRIzol reagent (Invitrogen) by following the manufacturer's direction. Five micrograms of total RNA was fractionated on a 1% agarose gel containing 2.2 M formaldehyde and transferred onto nylon membranes. Membranes were hybridized with riboprobes specific for plus-stranded HCV replicon RNA and Mx-A and β-actin mRNA in the conditions described previously (Guo, J. T., et al., 2001. J. Virol. 75:8516-8523).

Detection of eIF-2α phosphorylation by Western blotting. For Western blot analysis of eIF-2α phosphorylation, cells were treated with 100 IU of IFN-α/ml for 12 h and then transfected with 2 µg of poly(I:C) per 60-mm-diameter plate by using Lipofectamine (Invitrogen). After 3 h of incubation, cells were lysed in high-salt radioimmunoprecipitation assay buffer (50 mM Tris-HCl [pH 8.0], 250 mM NaCl, 1% NP-40, 0.5% deoxycholate, 0.1% sodium dodecyl sulfate [SDS]). Proteins (40 µg) were separated on SDS-10% polyacrylamide gel and electrophoretically transferred to nitrocellulose membranes. Membranes were incubated with 50% methanol, washed extensively with water, and blocked with 3% casein in TNET buffer (10 mM Tris-HCl [pH 7.5], 150 mM NaCl, 1 mM EDTA, 0.05% Tween 20). Membranes were incubated with rabbit polyclonal antibodies against eIF-2α (a gift from Robert Schneider, New York University) or phosphorylated eIF-2α (eIF-2α-P; Research Genetics, Inc.) diluted in blocking solution for 1 h and then washed extensively with TNET buffer. Membranes were then incubated with horseradish peroxidase-conjugated goat anti-rabbit and immunoglobulin G (IgG) (Amersham), respectively. The bound IgG was detected with Super-Signal chemiluminescence reagents (Pierce).

RPA. For the analysis of IFN-β gene expression, cells were treated with 100 IU of IFN-α/ml for 12 h and then transfected with 2 µg of poly(I:C) per 60-mm plate by using Lipofectamine (Invitrogen). After 3 h of incubation, total cellular RNA was extracted with TRIzol reagent (Invitrogen), and IFN-β mRNA levels were determined by RNase protection assay (RPA) with the help of the RPAII kit purchased from Ambion. The probes complementary to IFN-β (GenBank accession no. M25460) and β-actin (GenBank accession no. BC013380) mRNAs spanned positions 272 to 650 and 1030 to 1250, respectively.

Annexin V-FITC staining. SL1 cells were plated on coverslips in six-well plates 16 h prior to treatment. Cells were then mock treated or treated with 100 IU of IFN-α/ml in the absence or presence of 20 µM ZVAD-FMK. Coverslips were then put on slides and incubated with 100 µl of staining solution containing annexin V-fluorescein isothiocyanate (FITC) at room temperature for 10 to 15 min. After extensive washes with phosphate-buffered saline, slides were examined with a Nikon fluorescence microscope and photographed with a charge coupled device camera.

Flow cytometry analysis. To determine the fraction of apoptotic cells, the annexin V assay system (Roche Diagnostics GmbH) was used. Cells were incubated with IFN-α (100 IU/ml) alone or together with 20 µM ZVAD-FMK for 24 h. The culture medium containing detached cells was collected, and the adherent cells were trypsinized and then combined with the detached cells. The cells were collected by centrifugation and washed once in phosphate-buffered saline. Pelleted cells were resuspended in binding buffer and were incubated with annexin V-FITC at room temperature for 10 to 15 min. The stained cells were then diluted with binding buffer and analyzed by flow cytometry (FACScan; Becton Dickinson).

Results

IFN-α can Induce Noncytopathic and Cytopathic Antiviral Responses in Cells Comprising HCV Replicons.

Figure 7A:
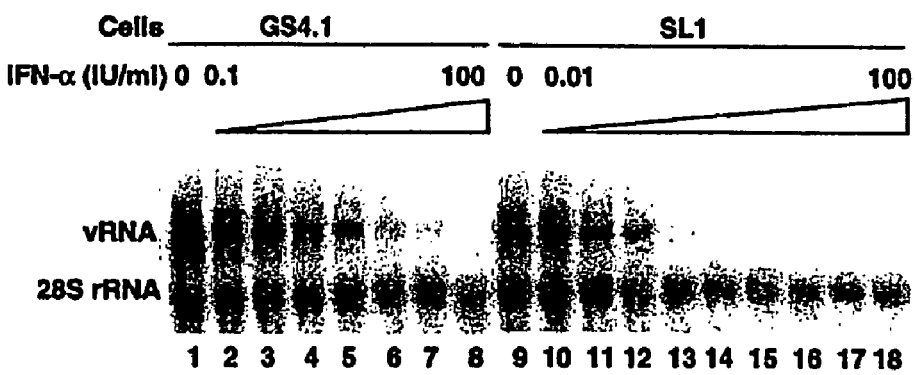
Figure 7B:
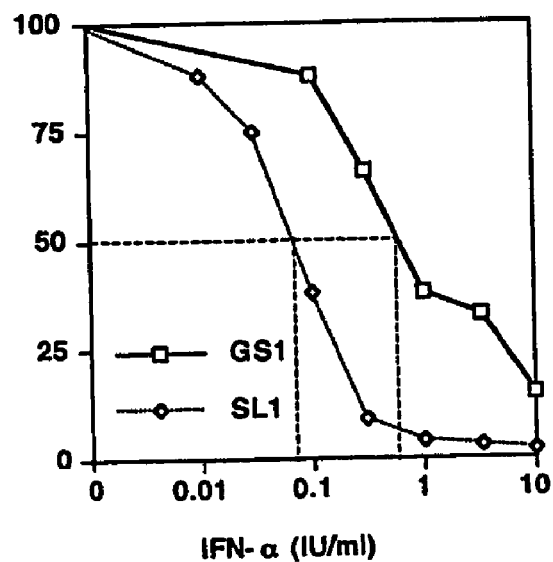
Figure 8A:
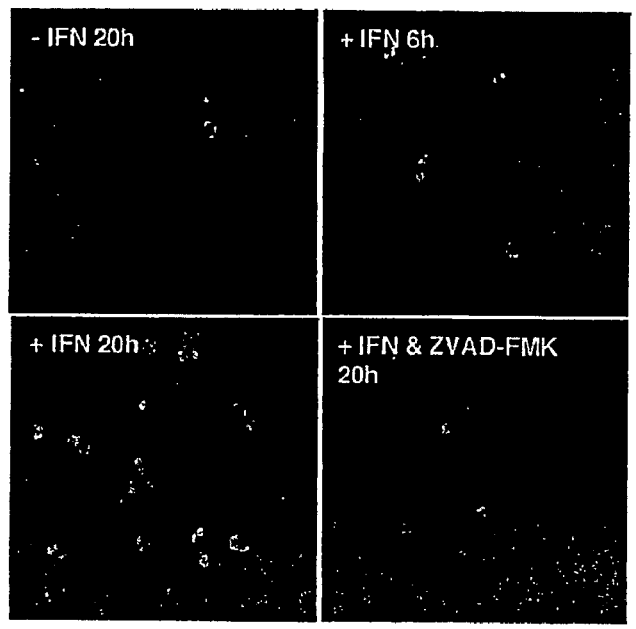
Figure 8B:
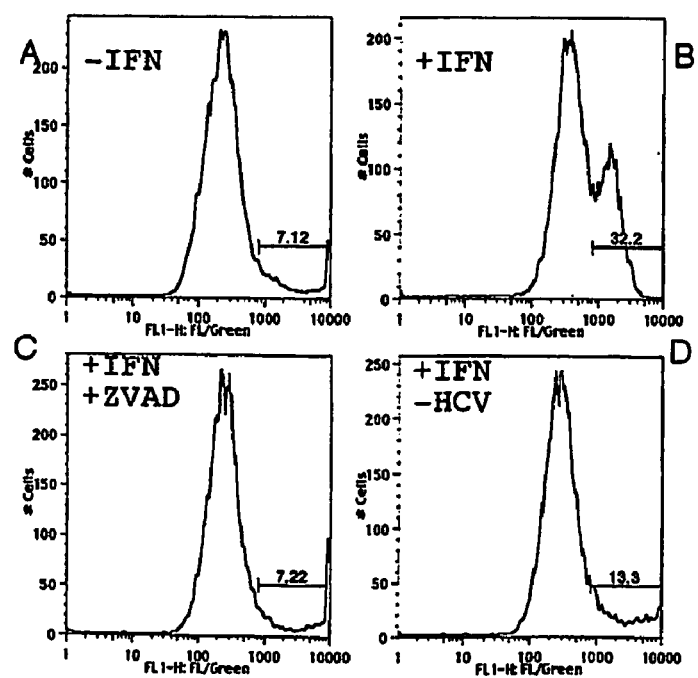

As set forth above, stable HeLa cell lines were established that express HCV subgenomes with an efficiency similar to that of Huh7 cells (Zhu, Q., et al., 2003. J. Virol. 77:9204-9210). Examination of the IFN-α response in HeLa derived cell lines such as SL1 revealed a very similar dose dependent reduction of virus replication. The $IC_{50}$ of IFN-α in HeLa cell lines was generally in the range of 0.1 IU/ml, approximately 10-fold lower than the IFN-α $IC_{50}$ in Huh7-derived cell lines (FIG. 7). However, in marked contrast to observations made with Huh7 cell lines, treatment of SL1 and other HeLa derived cell lines with more than 30 IU of IFN-α/ml induced cell death in a significant fraction of cells between 6 and 20 h post treatment (FIG. 8A). Cell death was caused by apoptosis, as determined by annexin V staining, and could be prevented by the caspase inhibitor ZVAD-FMK. The fraction of apoptotic cells was determined before and after treatment with the cytokine. The results showed that IFN-α induced apoptosis in more than 30% of SL1 cells compared with 6 to 7% in untreated SL1 and parental HeLa cells (FIG. 8B). Several other HeLa-derived cell lines were examined to assure that the results obtained with SL1 cells reflected a general property of HeLa cells expressing HCV subgenomes. Moreover, to test more directly whether IFN-induced apoptosis was caused by viral replication, two methods were used to inhibit RNA replication in SL1 cells. The first was based on the observation that replication of HCV subgenomes is temperature sensitive and is inhibited at 39° C. (J. A. Sohn and C. Seeger, unpublished observations). The second method relied on the availability of an inhibitor of the viral RNA polymerase. Consistent with a role for viral replication in the induction of apoptosis, cell death could be prevented when viral replication was inhibited by either incubation of the cells for 60 h at the elevated temperature or treatment with a viral polymerase inhibitor (FIG. 8B and result not shown).

Figure 9A:
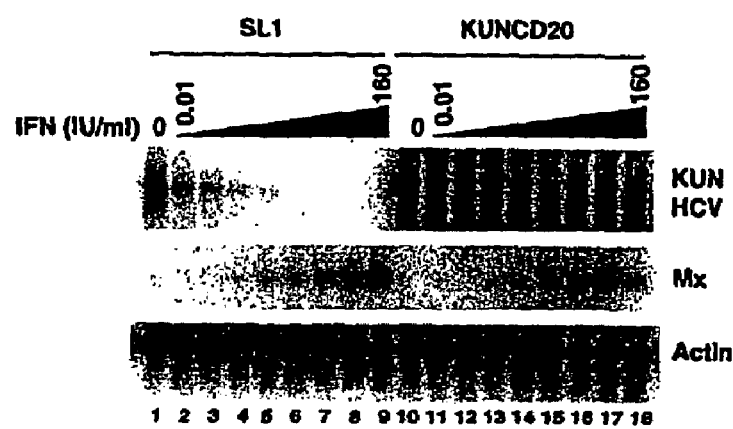
Figure 9B:
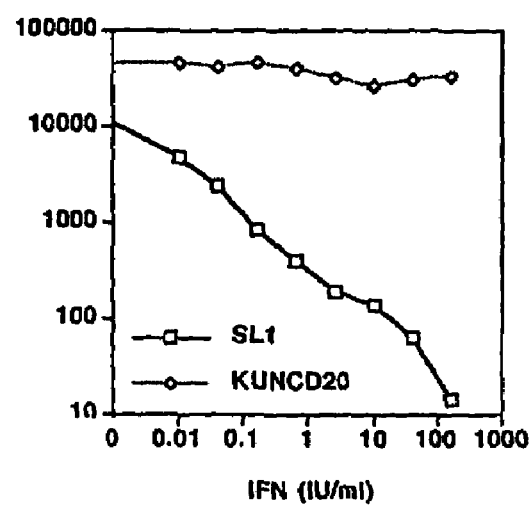

These results raised the question of whether IFN-induced apoptosis reflected a general property of HeLa cells expressing viral replicons. To address this problem, the IFN response against HCV in SL1 cells was compared with that against the flavivirus Kunjin virus in HeLa cells. For this purpose a pool of HeLa cells, KUNCD20, expressing Kunjin virus subgenomic replicons lacking the structural genes, similar to the HCV subgenomic replicons was established (Khromykh, A. A., and E. G. Westaway. 1997. J. Virol. 71:1497-1505). The Kunjin virus RNA levels in these cells were approximately fivefold higher than those observed with HCV in SL1 cells. In contrast to results with SL1 cells, treatment of KUNCD20 cells with different concentrations of IFN-α only slightly inhibited viral replication (FIG. 9). Importantly, cell death in IFN-α-treated KUNCD20 cells was not detected either by light microscopy or annexin V staining (results not shown). These results indicated that IFN-induced apoptosis is a property of HCV-expressing HeLa cells rather than a general property of HeLa cells replicating viral RNA genomes.

In summary, these results demonstrated that IFN-α could induce noncytopathic as well as cytopathic antiviral programs in cells expressing HCV replicons in a concentration- and cell type-dependent fashion. Moreover, the results showed that this antiviral program was specific for HCV replicons. Importantly, the results suggested that HCV replication could induce an innate cellular response that, in combination with IFN-α, could lead to apoptosis.

IFN-α Inhibits HCV Replication through the Jak-STAT Signal Transduction Pathway

Information about the signal transduction pathways responsible for execution of the IFN response has generally been obtained with cells treated with high concentrations (100 to 1,000 IU/ml) of the cytokine and with fibroblasts and epithelial cells, most of which cannot, to date, support HCV replication. Moreover, a recent study by Schlaak, et al. (Schlaak, J. F., et al., 2002., J. Biol. Chem. 277:49428-49437) revealed that the IFN response could vary in a cell type-dependent manner. In addition, it was found that slight changes in cell culture conditions had major effects on HCV replication. Therefore, the observation that replication of HCV in both Huh7 and HeLa cells could be inhibited with low concentrations of the cytokine warranted a more careful study of the pathways involved in the antiviral program against HCV.

To investigate the nature of the IFN-α response against the HCV replicon, drugs that were known to inhibit specific components of selected signal transduction pathways that play a role in the antiviral response induced by IFN-α were used (Table 5). The current model for the signal transduction pathway induced by IFN-α predicts that the IFN receptor associated tyrosine kinases Jak1 and Tyk2 are activated and, in turn, phosphorylate the transcription factors STAT1 and STAT2, which are required for the induction of the cellular antiviral program (FIG. 10) (Sen, G. C. 2001., Annu. Rev. Microbiol. 55:255-281; Stark, G. R., et al., 1998. Annu. Rev. Biochem. 67:227-264). Incubation of GS4.1 cells with the tyrosine kinase inhibitor genistein suppressed the induction of the IFN-induced Mx-1 gene (FIGS. 11A and 11B). Similarly, genistein antagonized the IFN-α response against the HCV replicon. An increase in the concentration of the drug from 100 to 300 µM led to a complete inhibition of the IFN response against HCV (results not shown). Consistent with this result, it was found that the V protein of HPIV2 blocked the IFN response. The V protein of HPIV2 induces the degradation of STAT2 and, hence, inhibits the IFN-induced activation of gene expression (Parisien, J. P., et al., 2002. J. Virol. 76:4190-4198) (FIGS. 11C and 11D). IFN-α treatment of cells expressing HPIV2 led to a twofold reduction of viral RNA levels. When adjusted for the observed transfection efficiency, i.e., 40 to 45% of the cells express the V protein, the reduction corresponded to a complete inhibition of the IFN-α response. Finally, the decline of viral RNA levels was reduced in GS4.1 cells with IFN-α and cycloheximide, indicating that de novo protein synthesis was required for an antiviral response against HCV replication (Table 5).

IFN-α can activate, in addition to the STAT pathway, MAPKs, including extracellular signal-regulated kinase, p38 MAPK, and phosphatidylinositol 3 (PI3)-kinase-Akt pathways (David, M., et al., 1995. Science 269:1721-1723; Goh, K. C., et al., 1999. EMBO J. 18:5601-5608; Pfeffer, L. M., et al., 1997. Science 276:1418-1420). However, in contrast to genistein, SB 203580, sodium salicylate, and wortmannin, known inhibitors of p38 MAPK, NF-κB, and PI-3 kinase, respectively, did not inhibit the IFN response at detectable levels, suggesting that the two major ancillary signaling pathways activated by IFN-α were not directly involved in inhibiting HCV replication in Huh7 cells (Table 5; results not shown).

In summary, the results showed that inhibition of HCV-replication with IFN-α depended on a functional Jak-STAT pathway (FIG. 10). Hence, the results demonstrated that the IFN response against HCV was genuine and did not reflect an unspecific effect of the cytokine.

Does HCV replication induce an antiviral state in infected cells? A critical step in activation of innate immunity is the induction of an antiviral state by dsRNA or viral proteins (FIG. 10) (Taniguchi, T., and A. Takaoka. 2002. Curr. Opin. Immunol. 14:111-116; tenOever, B. R., et al., 2002. J. Virol. 76:3659-3669). As shown above, evidence for such a virus-induced activation was also obtained from IFN-treated HeLa cells expressing HCV replicons. To investigate the nature of this HCV-induced activation, the phosphorylation levels of eIF-2α and expression of IFN-β were determined. eIF-2α is a substrate of PKR, which is activated by dsRNA that can accumulate as a consequence of viral RNA replication (Srivastava, S. P., et al., 1998. J. Biol. Chem. 273:2416-2423; Williams, B. R. 3 Jul. 2001, posting date. Signal integration via PKR. Sci STKE 2001:RE2. [Online.]). IFN-β gene transcription is activated through the coordinate actions of three families of transcription factors NF-κB, IRF3, and ATF2, all of which are activated by dsRNA and/or certain viral proteins (FIG. 10) (Peters, K. L., et al., 2002. Proc. Natl. Acad. Sci. USA 99:6322-6327; tenOever, B. R., et al., 2002. J. Virol. 76:3659-3669).

First the levels of eIF-2α-P in Huh7, GS4.1, HeLa, and SL1 cells was determined in the presence and absence of dsRNA and IFN-α. The results showed that eIF-2α-P levels were not significantly elevated in cells expressing HCV replicons (GS4.1 and SL1) compared with those in their parental cells (Huh7 and HeLa) (FIG. 12A). Similarly, incubation of cells with IFN-α did not induce eIF-2α-P levels. In contrast, transfection of cells with poly(I:C), mimicking dsRNA, augmented eIF-2α-P levels, particularly in HeLa and SL1 cells. Similar results were obtained when cells were primed with IFN-α prior to transfection with poly(I:C). These results were confirmed with several other cell lines derived from Huh7 and HeLa cells.

Second, the levels of IFN-β mRNA in the four cell lines was determined under the same conditions described above. In agreement with the above results, viral replication alone was not sufficient to activate IFN-β gene expression in both Huh7- and HeLa-derived cell lines (FIG. 12B). In Huh7 cells and GS4.1 and other Huh7-derived cells expressing HCV replicons, only a weak induction of IFN-β was observed when cells were primed with IFN-α and then transfected with poly(I:C). In contrast, IFN-β transcription was induced in HeLa and SL1 cells by poly(I:C) alone and particularly in combination with IFN-α. Remarkably, expression of IFN-β could be induced by IFN-α alone in SL1 cells but not in HeLa cells. Similar results were obtained with the HeLa-derived SL2 cell line (results not shown).

In summary, the results showed that, while both Huh7 and HeLa cells were competent to activate dsRNA-dependent signal transduction pathways, HCV replication alone was not sufficient to induce a detectable dsRNA response in these cells. This result could indicate that dsRNA either does not accumulate during HCV replication or cannot access PKR and other dsRNA binding proteins. Importantly, the results showed that, despite the apparent lack of biologically active dsRNA, viral replication could activate certain cellular signal transduction pathways that could cooperate with IFN-α to activate the transcription of the IFN-β gene.

The results presented above favored a model predicting that IFN-α inhibited HCV replication by a mechanism that was independent of dsRNA-activated antiviral pathways. To test this model more carefully, the IFN response was measured in GS4.1 cells expressing the vaccinia virus E3L protein. E3L is known to sequester dsRNA and prevent PKR and OAS/Rnase L activation (Chang, H. W., et al., 1992. Proc. Natl. Acad. Sci. USA 89:4825-4829; Rivas, C., et al., 1998. Virology 243:406-414) (FIG. 10). Indeed, expression of E3L had no measurable effect on the IFN response against HCV (FIGS. 11C and 11D). Experiments relying on simultaneous detection of E3L and the HCV protein NS5A in the same cell by immunofluorescence confirmed that IFN-α could inhibit HCV replication in cells expressing the E3L protein (results not shown). Finally, it was found that the PKR inhibitors 2-amino purine (2-AP) and adenovirus VA RNA did not block the IFN response against HCV in Huh7 cells (Table 5).

TABLE 5

Effects of inhibitors on the activity of IFN-α against the HCV replicon[a]

| Drug, protein, or RNA | Concn | Primary target(s) | Effect |
|---|---|---|---|
| 2-AP | 10 mM | PKR and other kinases | − |
| Genistein | 300 μM | Tyrosine kinases | + |
| Cycloheximide | 10 μg/ml | Translation | + |
| Sodium salicylate | 5 mM | IKK | − |
| SB 203580 | 20 μM | p38 MAPK | − |
| PD 98059 | 50 μM | MEK kinase | − |
| Vanadate | 50 μM | Protein phosphatase | − |
| Wortmannin | 100 nM | PI3 kinase | − |
| PP2 | 50 μM | src kinase | − |
| Rapamycin | 200 nM | mTOR, translation | − |
| Lactacystin | 5 μM | 26S proteasome | + |
| Epoxomicin | 1 μM | 26S proteasome | + |
| V protein of HPIV2 | | STAT2 | + |
| E3L protein | | PKR and OAS | − |
| VA RNA | | PKR | − |

[a]GS4.1 cells were incubated with the indicated compounds for 2 h and then the presence of 100 IU of IFN-α/ml for an additional 24 h. Viral RNA levels were determined by Northern blot analysis. Assays for V protein, E3L, and VA RNA are described in the legend to FIG. 5.

What are the pathways that play a role in the IFN-α response against HCV? A major question concerns the mechanism by which IFN-α induces the noncytopathic inhibition of HCV replication. DNA microarray analyses of IFN-α-treated GS4.1 cells and other Huh7-derived cell lines revealed the induction of several classes of genes belonging to known signal transduction and protein degradation pathways (J. Hayashi and C. Seeger, unpublished results; Cheney, I. W., et al. 2002. J. Virol. 76:11148-11154). In particular, several genes encoding proteasome subunits and ubiquitin-like proteins were among the genes most highly induced by IFN-α. Notably, kinetic studies of HCV replication in Huh7 cells indicated that replication complexes have a relatively short halflife, which is further reduced by IFN treatment (J.-T. Guo and C. Seeger, unpublished observations). Therefore, it was surmised that the proteasome could play a role in inhibition of HCV replication in IFN-treated cells.

To test this hypothesis, the outcome of combination treatment with IFN-α and the proteasome inhibitors lactacystin and epoxomicin for HCV RNA replication in GS4.1 cells was determined. The cells were pretreated with different concentrations of the inhibitors for 1 h before IFN-α was added for an additional 6 h of combination treatment. Then the cells were incubated for 12 h before RNA was isolated and subjected to Northern blot analysis (FIG. 13A). The relatively short incubation period was necessary because of the known toxicity of proteasome inhibitors after longer incubation times. The results showed that HCV RNA levels dropped 70% within 18 h of IFN-α treatment, whereas in the presence of epoxomicin or lactacystin the reduction was only 30% (FIG. 13B). Lower doses of epoxomicin than of lactacystin were effective, which is consistent with the high specific activity of epoxomicin against the chymotrypsin-like activity of proteasomes (Fenteany, G., and S. L. Schreiber. 1998. J. Biol. Chem. 273:8545-8548; Meng, L., et al., 1999. Proc. Natl. Acad. Sci. USA 96:10403-10408). Treatment with higher doses of lactacystin alone led to a slight reduction of HCV RNA levels. These results were confirmed with a second set of experiments. The cells were pretreated with 5 μM lactacystin and 1 μM epoxomicin, respectively, for 1 h before IFN-α was added for an additional 6 h of combination treatment. RNA was isolated from the treated cells either 6 or 12 h after incubation with IFN-α (FIG. 14). The results showed that, at both time points, viral RNA levels were significantly higher in cells that were exposed to the proteasome inhibitors than in cells that were treated with IFN-α alone.

Finally, tests were conducted to determine whether proteasome activity was required for induction of the IFN response or, more directly, for inhibition of HCV replication. To distinguish between these two possibilities, first GS4.1 cells were incubated with the cytokine for 10 h to induce the antiviral response. Then, the cells were incubated for 12 h in the presence of lactacystin or epoxomicin. Under these conditions, the IFN response against HCV remained effective and reduced RNA levels to similar extents independently of the presence of either of the two inhibitors (FIG. 15). Thus, these results indicated that the activity of proteasomes is required for the induction of the IFN response against HCV, but apparently not for direct inhibition of viral replication (see Discussion).

Discussion

In this Example, the mechanism of the IFN-α response against subgenomic replicons of HCV in Huh7 and HeLa cells is investigated. The following conclusions can be drawn from these investigations. First, it can be concluded that IFN-α can inhibit HCV replication by both noncytopathic and cytopathic mechanisms. These results demonstrating that SL1 cells treated with IFN-α (100 IU/ml) underwent programmed cell death raised the question of whether apoptosis contributes to the rapid decline of HCV RNA levels observed during the first 48 h of IFN therapy (Neumann, A. U., et al., 1998. Science 282:103-107). The answer depends on whether HeLa or Huh7 cells mimic the scenario in HCV-infected hepatocytes in vivo. It is known from this and other studies that Huh7 cells exhibit an attenuated response to dsRNA and cannot induce an apoptotic program (results not shown) (Keskinen, P., et al., 1999. Virology 263:364-375; Lanford, R. E., et al., 2003. J. Virol. 77:1092-1104; McNair, A. N., et al., 1994. J. Gen. Virol. 75:1371-1378). In contrast, HeLa cells respond to dsRNA in a fashion similar to that in which primary chimpanzee hepatocytes respond. For example, treatment of chimpanzee primary hepatocyte cultures with poly (I:C) led to the induction of IFN-β, as shown in this report with HeLa cells (FIG. 12) (Lanford, R. E., et al., 2003. J. Virol. 77:1092-1104). Therefore, it is likely that HeLa cells represent a more physiological model for hepatocytes in terms of IFN response than Huh7 cells. It was notable that only a fraction of SL1 cells died after treatment with IFN-α. One possibility is that apoptosis was induced in cells that replicated above-average levels of HCV RNA. In support of this possibility, reduction of viral levels by treatment with heat or HCV RNA polymerase inhibitors reduced the number of apoptotic cells after IFN-α treatment (FIG. 8 and results not shown). Based on these results it was concluded that HeLa cells did not undergo apoptosis by default after IFN-α treatment. In fact, it appears that apoptosis is a hallmark of HCV-replicating HeLa cells, because HeLa cells replicating Kunjin virus RNA remained viable after IFN treatment. Finally, it appears that, the observation reported here represents the first example of IFN-α-induced apoptosis of cells replicating an apparently noncytolytic RNA virus.

Second, it can be concluded that the noncytopathic response can occur independently of dsRNA-dependent pathways. Although these results showed that dsRNA response pathways were at least partially functional in normal and HCV-replicating Huh7 cells and were intact in HeLa cells, as indicated by poly(I:C)-induced phosphorylation of eIF-2α and IFN-β gene transcription, viral replication per se did not induce such responses (FIG. 12). The expression of the vaccinia virus E3L protein or treatment of cells with the kinase inhibitor 2-AP had no measurable effect on the IFN response against the HCV replicon (FIG. 11 and Table 5). These observations were consistent with the notion that dsRNA-dependent antiviral pathways, such as PKR and RNase L pathways, were not involved in IFN-induced inhibition of HCV replication in Huh7 cells. Whether they play a role in HeLa cells is not yet known. Efforts to express E3L in SL1 cells were not successful due to the apparent toxicity of the protein, and treatment of HeLa cells with 2-AP for more than 12 h induced apoptosis (results not shown). Importantly, it is not yet known whether IFN-induced apoptosis in HCV-expressing cells is dependent on PKR or other dsRNA-dependent pathways (see below).

In summary, the results showed that, while both Huh7 and HeLa cells were competent to activate dsRNA-dependent signal transduction pathways, HCV replication alone was not sufficient to induce a detectable dsRNA response in these cells. This result could indicate that dsRNA either did not accumulate during HCV replication or was not accessible to PKR and other dsRNA binding proteins.

Third, it can be concluded that HCV replication can induce innate immune pathways. In SL1 and other HCV-expressing HeLa cell lines (results not shown), but not in normal HeLa cells, IFN-α induced the expression of IFN-β. This indicates that HCV replication activated an unknown cellular factor, perhaps a viral activated kinase as proposed by Smith and colleagues (Smith, E. J., et al., 2001. J. Biol. Chem. 276:8951-8957), that, in turn, activated one or more transcription factors required for IFN-β transcriptional activation. Candidates include IRF3, NF-κB, and ATF-2 (FIG. 10). Because normal HeLa cells did not undergo apoptosis after IFN-α treatment, it can be concluded that HCV expression directs the IFN-α response into a cytopathic process.

Fourth, it can be concluded that the antiviral activity of IFN-α against HCV depends, in part, on functional proteasomes. How IFN-induced antiviral programs inhibit viral replication noncytopathically is not yet understood. The results shown here demonstrate that, for HCV replication, proteasomes were required for this process. However, the idea that proteasomes were directly involved in inhibition of HCV replication by increasing the turnover of replication complexes or viral proteins was not supported by these results. Instead evidence was obtained that induction of the IFN response was dependent on degradation of one or several proteins. Previously, it has been shown (Li, X. L., and B. A. Hassel. 2001. Cytokine 14:247-252) that proteasome inhibitors attenuated the induction of certain IFN-stimulated genes. Because epoxomicin and lactacystin did not inhibit induction of Mx-A (results not shown), which is dependent on activation of the Jak-STAT pathway for the formation of ISGF3, proteasomes might be involved in the induction of the second-wave IFN-stimulated genes. Such a model is consistent with results published previously by Li and Hassel (Li, X. L., and B. A. Hassel. 2001. Cytokine 14:247-252), who found that treatment of cells with proteasome inhibitors did not inhibit phosphorylation of STAT1 and binding of ISGF3 to DNA. As a consequence of these results, the number of IFN-induced genes that play a role in inhibition of HCV replication by IFN-α can be reduced to those that are repressed by epoxomicin.

An important implication of these results for clinical IFN-α therapy and the pathogenesis of HCV infections is that besides the noncytopathic antiviral effects, IFN-α might also induce apoptosis of HCV-infected infected hepatocytes. At first glance, this possibility might be discounted because drug-induced cell death could lead immediately to the destruction of the infected liver. However, it is possible that only a fraction of hepatocytes express levels of HCV high enough to activate an apoptotic program in the presence of the high levels of IFN-α that are used for antiviral therapy. In this scenario cell death would occur unnoticed. An important consequence of such a scenario would be that cell killing could play a major role in the recovery from chronic HCV infections, similar to the situation in natural recovery from transient infections with woodchuck hepatitis virus, a model for hepatitis B virus infections (Guo, J. T., et al., 2000. J. Virol. 74:1495-1505).

TABLE 6

Listing of Sequence ID Numbers

| Sequence | Sequence ID Number |
| --- | --- |
| $I_{377}$/NS3-3' | SEQ ID NO: 1 |
| pZS1 | SEQ ID NO: 2 |
| pZS2 | SEQ ID NO: 3 |
| pZS4 | SEQ ID NO: 4 |
| pZS5 | SEQ ID NO: 5 |
| pZS6 | SEQ ID NO: 6 |
| pZS8 | SEQ ID NO: 7 |
| pZS10 | SEQ ID NO: 8 |
| pZS11 | SEQ ID NO: 9 |
| pZS12 | SEQ ID NO: 10 |
| pZS15 | SEQ ID NO: 11 |
| pZS20 | SEQ ID NO: 12 |
| pZS25 | SEQ ID NO: 13 |
| pZS45 | SEQ ID NO: 14 |
| Mx-A cDNA primer #1 | SEQ ID NO:15 |
| Mx-A cDNA primer #2 | SEQ ID NO:16 |

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A hepatitis C virus (HCV) replicating cell line, wherein said cell line is a mouse cell line comprising an HCV genome.

2. The cell line of claim 1, wherein the mouse cell line comprises mouse cells of hepatic origin.

3. The cell line of claim 2, wherein the mouse cells are Hepa1-6 cells.

4. The cell line of claim 2, wherein the mouse cells are AML12 cells.

5. The cell line of claim 1, wherein said HCV genome is a HCV subgenome.

6. The cell line of claim 1, wherein said HCV genome is obtained from a second cell line which replicates HCV.

7. A method of producing the cell line of claim 1, comprising:
  a) obtaining total RNA from a human non-hepatic cell culture that replicates HCV, said total RNA comprising a selection marker which renders cells expressing said RNA resistant to a selection agent;
  b) introducing the total RNA into mouse cells;

c) selecting those cells which grow in the presence of said selection agent and replicate HCV; and d) generating a cell line from the cells of step c).

8. A method for screening test compounds which inhibit HCV replication, comprising:
   a) culturing the cell line of claim 1 in the presence and absence of a test compound; and
   b) assaying HCV replication levels in the presence and absence of said test compound, wherein a reduced HCV replication level in the presence of said test compound is indicative that said test compound inhibits HCV replication.

9. A method for screening test compounds which modulate the antiviral response induced by interferon alpha (IFN-α) comprising
   a) culturing the cell line of claim 1 in the presence and absence of a test compound;
   b) contacting the cells of step a) with IFN-α; and
   c) measuring the HCV replication level in the presence and absence of said compound thereby identifying agents which modulate the antiviral response mediated by IFN-α as a function of altered HCV levels.

10. The method of claim 9, wherein the antiviral response is enhanced.

11. The method of claim 9, wherein the antiviral response is inhibited.

12. A hepatitis C virus (HCV) replicating cell line, wherein said cell line is a
   human non-hepatic cell line,
   wherein said cell line comprises genomic HCV RNA, and
   wherein said genomic HCV RNA consists of HCV RNA obtainable from a second HCV replicating human cell line.

13. The cell line of claim 12, wherein the human non-hepatic cell line comprises epithelial cells.

14. The cell line of claim 13, wherein the human epithelial cells are HeLa cells.

15. The cell line of claim 12, wherein said HCV genome is a HCV subgenome.

16. The cell line of claim 15, wherein said second cell line is a Huh7 derived cell line.

17. The cell line of claim 12, wherein said second cell line is a Huh7 derived cell line.

18. The cell line of claim 12, wherein said RNA from the second cell line is the total RNA.

19. A method for producing the cell line of claim 12, comprising:
   a) obtaining total RNA from a human hepatic cell culture that replicates HCV, said total RNA comprising a selection marker which renders cells expressing said RNA resistant to a selection agent;
   b) introducing the total RNA into human non-hepatic cells;
   c) selecting those cells which grow in the presence of said selection agent and replicate HCV; and
   d) generating a cell line from the cells of step c).

20. A method for screening test compounds which inhibit HCV replication, comprising:
   a) culturing the cell line of claim 12 in the presence and absence of a test compound; and
   b) assaying HCV replication levels in the presence and absence of said test compound, wherein a reduced HCV replication level in the presence of said test compound is indicative that said test compound inhibits HCV replication.

21. A method for screening test compounds which modulate the antiviral response induced by interferon alpha (TEN-α) comprising
   a) culturing the cell line of claim 12 in the presence and absence of a test compound;
   b) contacting the cells of step a) with TEN-α; and
   c) measuring the HCV replication level in the presence and absence of said compound thereby identifying agents which modulate the antiviral response mediated by IFN-α as a function of altered HCV levels.

22. The method of claim 21, wherein the antiviral response is enhanced.

23. The method of claim 21, wherein the antiviral response is inhibited.

* * * * *

UNITED STATES PATENT AND TRADEMARK OFFICE
CERTIFICATE OF CORRECTION

| | |
|---|---|
| PATENT NO. | : 7,416,840 B2 |
| APPLICATION NO. | : 10/536955 |
| DATED | : August 26, 2008 |
| INVENTOR(S) | : Qing Zhu, Ju-Tao Guo and Christoph Seeger |

It is certified that error appears in the above-identified patent and that said Letters Patent is hereby corrected as shown below:

In the Specification

Column 1, Lines 13-17, delete the paragraph:
"Pursuant to 35 U.S.C. Section 202(c), it is acknowledged that the United States government has certain rights in the invention described herein, which was made in part with funds from the National Institutes of Health Grant No. AI48046."

And insert therefor:
--This invention was made with government support under AI048046 awarded by the National Institutes of Health. The government has certain rights in the invention.--

Signed and Sealed this
Twenty-second Day of August, 2023

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 11313
<212> TYPE: DNA
<213> ORGANISM: Artificial Sequence
<220> FEATURE:
<223> OTHER INFORMATION: Plasmid

<400> SEQUENCE: 1

```
gccagccccc gattgggggc gacactccac catagatcac tccctgtga ggaactactg    60
tcttcacgca gaaagcgtct agccatggcg ttagtatgag tgtcgtgcag cctccaggac   120
ccccctccc gggagagcca tagtggtctg cggaaccggt gagtacaccg gaattgccag   180
gacgaccggg tcctttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
ctcaaagaaa aaccaaaggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc aggggcgccc ggttcttttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga   720
aagtatccat catggctgat gcaatgcggc ggctgcatac gcttgatccg gctacctgcc   780
cattcgacca ccaagcgaaa catcgcatcg agcgagcacg tactcggatg aagccggtc    840
ttgtcgatca ggatgatctg gacgaagagc atcaggggct cgcgccagcc gaactgttcg   900
ccaggctcaa ggcgcgcatg cccgacggcg aggatctcgt cgtgacccat ggcgatgcct   960
gcttgccgaa tatcatggtg gaaaatggcc gcttttctgg attcatcgac tgtggccggc  1020
tgggtgtggc ggaccgctat caggacatag cgttggctac ccgtgatatt gctgaagagc  1080
ttggcggcga atgggctgac cgcttcctcg tgctttacgg tatcgccgct cccgattcgc  1140
agcgcatcgc cttctatcgc cttcttgacg agttcttctg agtttaaaca gaccacaacg  1200
gtttccctct agcgggatca attccgcccc tctccctccc cccccctaa cgttactggc   1260
cgaagccgct tggaataagg ccggtgtgcg tttgtctata tgttattttc caccatattg  1320
ccgtcttttg gcaatgtgag ggcccggaaa cctggccctg tcttcttgac gagcattcct  1380
aggggtcttt cccctctcgc caaggaatg caaggtctgt tgaatgtcgt gaaggaagca   1440
gttcctctgg aagcttcttg aagacaaaca acgtctgtag cgacccttg caggcagcgg   1500
aaccccccac ctggcgacag gtgcctctgc ggccaaaagc cacgtgtata agatacacct  1560
gcaaaggcgg cacaacccca gtgccacgtt gtgagttgga tagttgtgga aagagtcaaa  1620
tggctctcct caagcgtatt caacaagggg ctgaaggatg cccagaaggt accccattgt  1680
atgggatctg atctgggcc tcggtgcaca tgctttacat gtgtttagtc gaggttaaaa   1740
aacgtctagg ccccccgaac cacggggacg tggttttcct ttgaaaaaca cgataatacc  1800
atggcgccta ttacggccta ctcccaacag acgcgaggcc tacttggctg catcatcact  1860
agcctcacag gccgggacag gaaccaggtc gaggggagg tccaagtggt ctccaccgca   1920
acacaatctt tcctggcgac ctgcgtcaat ggcgtgtgtt ggactgtcta tcatggtgcc  1980
ggctcaaaga cccttgccgg cccaaagggc ccaatcaccc aaatgtacac caatgtggac  2040
caggacctcg tcggctggca agcgcccccc ggggcgcgtt ccttgacacc atgcacctgc  2100
ggcagctcgg acctttactt ggtcacgagg catgccgatg tcattccggt gcgcggcgg   2160
ggcgacagca gggggagcct actctccccc aggcccgtct cctacttgaa gggctcttcg  2220
ggcggtccac tgctctgccc ctcggggcac gctgtgggca tctttcggc tgccgtgtgc  2280
acccgagggg ttgcgaaggc ggtggacttt gtacccgtcg agtctatgga aaccactatg  2340
```

```
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580 accacggggtg cccccatcac gtactccacc tatggcaagt tcttgccga cggtggttgc    2640 tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatcccctt tatggcaaag ccatccccat cgagaccatc    2880 aagggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca cgtggtcat tgtgggcagg    3780 atcatcttgt ccggaaagcc ggccatcatt cccgacaggg aagtcctta ccgggagttc    3840 gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctcc accgaggacc tggttaacct actccctgct    4380
atcctctccc ctggcgccct agtcgtcggg gtcgtgtgcg cagcgatact gcgtcggcac    4440
gtgggcccag ggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
```

-continued

```
acgtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctaggcgct gtggcgggtg    4980
gctgctgagg agtacgtgga ggttacgcgg gtgggggatt ccactacgt gacgggcatg    5040
accactgaca acgtaaagtg cccgtgtcag gttccggccc cgaattctt cacagaagtg    5100
gatgggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccccttga ggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggcccttttac gatgtggtct ccaccctccc tcaggccgtg    6540
atgggctctt catacggatt ccaatactct cctggacagc gggtcgagtt cctggtgaat    6600
gcctggaaag cgaagaaatg ccctatggcc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccctg    6780
actaattcta aagggcagaa ctgcggctat cgccggtgcc gcgcgagcgg tgtactgacg    6840
accagctgcg gtaatacct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctggggaccc gcccaaacca gaatacgact tggagttgat aacatcatgc    7080
```

```
tcctccaatg tgtcagtcgc gcacgatgca tctggcaaaa gggtgtacta tctcacccgt      7140
gaccccacca cccccttgc gcgggctgcg tgggagacag ctagacacac tccagtcaat       7200
tcctggctag gcaacatcat catgtatgcg cccaccttgt gggcaaggat gatcctgatg      7260
actcatttct tctccatcct tctagctcag gaacaacttg aaaaagccct agattgtcag      7320
atctacgggg cctgttactc cattgagcca cttgacctac ctcagatcat tcaacgactc      7380
catggcctta gcgcattttc actccatagt tactctccag gtgagatcaa tagggtggct      7440
tcatgcctca ggaaacttgg ggtaccgccc ttgcgagtct ggagacatcg ggccagaagt      7500
gtccgcgcta ggctactgtc caggggggg agggctgcca cttgtggcaa gtacctcttc       7560
aactgggcag taaggaccaa gctcaaactc actccaatcc cggctgcgtc ccagttggat      7620
ttatccagct ggttcgttgc tggttacagc gggggagaca tatatcacag cctgtctcgt      7680
gcccgacccc gctggttcat gtggtgccta ctcctacttt ctgtagggt aggcatctat       7740
ctactcccca accgatgaac ggggacctaa acactccagg ccaataggcc atcctgtttt      7800
tttccctttt tttttttctt tttttttttt tttttttttt tttttttttt ttctcctttt      7860
ttttcctct tttttttcctt ttctttcctt tggtggctcc atcttagccc tagtcacggc      7920
tagctgtgaa aggtccgtga gccgcttgac tgcagagagt gctgatactg gcctctctgc      7980
agatcaagta ctcctgcagg cgcgccacta gtgggaatac gcggggtatg ccgcgtttta      8040
gcatattgac gacccaattc tcatgtttga cagcttatca tcgataagct taatgcggt       8100
agtttatcac agttaaattg ctaacgcagt caggcaccgt gtatgaaatc taacaatgcg      8160
ctcatcgtca tcctcggcac cgtcaccctg gatgctgtag gcataggctt ggttatgccg      8220
gtactgccgg gcctcttgcg ggatatcgtc cattccgaca gcatcgccag tcactatggc      8280
gtgctgctag cgctatatgc gttgatgcaa tttctatgcg cacccgttct cggagcactg      8340
tccgaccgct ttggccgccg cccagtcctg ctcgcttcgc tacttggagc cactatcgac      8400
tacgcgatca tggcgaccac acccgtcctg tggatcctct acgccggacg catcgtggcc      8460
ggcatcaccg cgccacagg tgcggttgct ggcgcctata tcgccgacat caccgatggg       8520
gaagatcggg ctcgccactt cgggctcatg agcgcttgtt tcggcgtggg tatggtggca      8580
ggccccgtgg ccgggggact gttgggcgcc atctccttgc atgcaccatt ccttgcggcg      8640
gcggtgctca acggcctcaa cctactactg ggctgcttcc taatgcagga gtcgcataag      8700
ggagagcgtc gaccgatgcc cttgagagcc ttcaacccag tcagctcctt ccggtgggcg      8760
cggggcatga ctatcgtcgc cgcacttatg actgtcttct ttatcatgca actcgtagga      8820
caggtgccgg cagcgctctg ggtcatttc ggcgaggacc gctttcgctg gagcgcgacg       8880
atgatcggcc tgtcgcttgc ggtattcgga atcttgcacg ccctcgctca agccttcgtc      8940
actggtcccg ccaccaaacg tttcggcgag aagcaggcca ttatcgccgg catggcggcc      9000
gacgcgctgg gctacgtctt gctggcgttc gcgacgcgag gctggatggc cttccccatt      9060
atgattcttc tcgcttccgg cggcatcggg atgcccgcgt tgcaggccat gctgtccagg      9120
caggtagatg acgaccatca gggacagctt caaggatcgc tcgcggctct taccagccta      9180
acttcgatca ctggaccgct gatcgtcacg gcgatttatg ccgcctcggc gagcacatgg      9240
aacgggttgg catggattgt aggcgccgcc ctataccttg tctgcctccc gcgcgttcgt      9300
cgcggtgcat ggagccgggc cacctcgacc tgaatggaag ccggcggcac ctcgctaacg      9360
gattcaccac tccaagaatt ggagccaatc aattcttgcg gagaactgtg aatgcgcaaa      9420
```

-continued

```
ccaacccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc cataccgcca    9840
gttgtttacc ctcacaacgt tccagtaacc gggcatgttc atcatcagta acccgtatcg    9900
tgagcatcct ctctcgtttc atcggtatca ttaccccat gaacagaaat tccccttac     9960 acggaggcat caagtgacca acaggaaaa accgcccctt aacatggccc gctttatcag   10020
aagccagaca ttaacgcttc tggagaaact caacgagctg gacgcggatg aacaggcaga   10080
catctgtgaa tcgcttcacg accacgctga tgagctttac cgcagctgcc tcgcgcgttt   10140
cggtgatgac ggtgaaaacc tctgacacat gcagctcccg gagacggtca gcttgtct    10200 gtaagcggat gccggagca gacaagcccg tcagggcgcg tcagcgggtg ttggcgggtg   10260
tcggggcgca gccatgaccc agtcacgtag cgatagcgga gtgtatactg gcttaactat   10320
gcggcatcag agcagattgt actgagagtg caccatatgc ggtgtgaaat accgcacaga   10380
tgcgtaagga gaaaataccg catcaggcgc tcttccgctt cctcgctcac tgactcgctg   10440
cgctcggtcg ttcggctgcg gcgagcggta tcagctcact caaaggcggt aatacggtta   10500
tccacagaat caggggataa cgcaggaaag aacatgtgag caaaaggcca gcaaaaggcc   10560
aggaaccgta aaaaggccgc gttgctggcg ttttttccata ggctccgccc ccctgacgag   10620
catcacaaaa atcgacgctc aagtcagagg tggcgaaacc cgacaggact ataaagatac   10680
caggcgtttc ccctggaag ctccctcgtg cgctctcctg ttccgaccct gccgcttacc    10740
ggatacctgt ccgcctttct cccttcggga agcgtggcgc tttctcatag ctcacgctgt   10800
aggtatctca gttcggtgta ggtcgttcgc tccaagctgg gctgtgtgca cgaaccccc    10860 gttcagcccg accgctgcgc cttatccggt aactatcgtc ttgagtccaa cccggtaaga   10920
cacgacttat cgccactggc agcagccact ggtaacagga ttagcagagc gaggtatgta   10980
ggcggtgcta cagagttctt gaagtggtgg cctaactacg gctacactag aaggacagta   11040
tttggtatct gcgctctgct gaagccagtt accttcggaa aaagagttgg tagctcttga   11100
tccggcaaac aaaccaccgc tggtagcggt ggtttttttg tttgcaagca gcagattacg   11160
cgcagaaaaa aaggatctca agaagatcct ttgatctttt ctacggggtc tgacgctcag   11220
tggaacgaaa actcacgtta agggattttg gtcatgagat tatcaaaaag gatcttcacc   11280
tagatccttt tctagataat acgactcact ata                                 11313
```

<210> SEQ ID NO 2
<211> LENGTH: 11313
<212> TYPE: DNA
<213> ORGANISM: Artificial Sequence
<220> FEATURE:
<223> OTHER INFORMATION: Plasmid

<400> SEQUENCE: 2

```
gccagccccc gattggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
```

```
gacgaccggg tcctttcttg gatcaacccg ctcaatgcct ggagatttgg gcgtgccccc      240
gcgagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaaggg cgcgccatga ttgaacaaga tggattgcac gcaggttctc      420
cggccgcttg ggtggagagg ctattcggct atgactgggc acaacagaca atcggctgct      480
ctgatgccgc cgtgttccgg ctgtcagcgc agggggcgccc ggttcttttt gtcaagaccg      540
acctgtccgg tgccctgaat gaactgcagg acgaggcagc gcggctatcg tggctggcca      600
cgacgggcgt tccttgcgca gctgtgctcg acgttgtcac tgaagcggga agggactggc      660
tgctattggg cgaagtgccg gggcaggatc tcctgtcatc tcaccttgct cctgccgaga      720
aagtatccat catggctgat gcaatgcggc ggctgcatac gcttgatccg gctacctgcc      780
cattcgacca ccaagcgaaa catcgcatcg agcgagcacg tactcggatg aagccggtc       840 ttgtcgatca ggatgatctg gacgaagagc atcaggggct cgcgccagcc gaactgttcg      900
ccaggctcaa ggcgcgcatg cccgacgcg aggatctcgt cgtgacccat ggcgatgcct       960
gcttgccgaa tatcatggtg gaaaatggcc gcttttctgg attcatcgac tgtggccggc     1020
tgggtgtggc ggaccgctat caggacatag cgttggctac ccgtgatatt gctgaagagc     1080
ttggcggcga atgggctgac cgcttcctcg tgctttacgg tatcgccgct cccgattcgc     1140
agcgcatcgc cttctatcgc cttcttgacg agttcttctg agtttaaaca gaccacaacg     1200
gtttccctct agcgggatca attccgcccc tctccctccc cccccctaa cgttactggc      1260 cgaagccgct tggaataagg ccggtgtgcg tttgtctata tgttattttc caccatattg     1320
ccgtcttttg gcaatgtgag ggcccggaaa cctggccctg tcttcttgac gagcattcct     1380
aggggtcttt cccctctcgc caaggaatg caaggtctgt tgaatgtcgt gaaggaagca      1440 gttcctctg aagcttcttg aagacaaaca acgtctgtag cgaccctttg caggcagcgg      1500
aaccccccac ctggcgacag gtgcctctgc ggccaaaagc cacgtgtata agatacacct     1560
gcaaaggcgg cacaacccca gtgccacgtt gtgagttgga tagttgtgga aagagtcaaa     1620
tggctctcct caagcgtatt caacaagggg ctgaaggatg cccagaaggt accccattgt     1680
atgggatctg atctggggcc tcggtgcaca tgctttacat tgtgttagtc gaggttaaaa     1740
aacgtctagg cccccccgaac cacggggacg tggtttttcct ttgaaaaaca cgataatacc    1800
atggcgccta ttacggccta ctcccaacag acgcgaggcc tacttggctg catcatcact     1860
agcctcacag gccgggacag gaaccaggtc gaggggggagg tccaagtggt ctccaccgca    1920
acacaatctt tcctggcgac ctgcgtcaat ggcgtgtgtt ggactgtcta tcatggtgcc     1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc     2100
ggcagctcgg accttactt ggtcacgagg catgccgatg tcattccggt gcgccggcgg     2160
ggcgacagca gggggagcct actctccccc aggcccgtct cctacttgaa gggctcttcg     2220
ggcggtccac tgctctgccc ctcggggcac gctgtgggca tctttcgggc tgccgtgtgc     2280
acccgagggt tgcgaaggc ggtggacttt gtacccgtcg agtctatgga aaccactatg     2340
cggtccccgg tcttcacgga caactcgtcc cctccggccg taccgcagac attccaggtg     2400
gcccatctac acgcccctac tggtagcggc aagagcacta aggtgccggc tgcgtatgca     2460
gcccaagggt ataaggtgct tgtcctgaac ccgtccgtcg ccgccaccct aggtttcggg     2520
```

```
gcgtatatgt ctaaggcaca tggtatcgac cctaacatca gaaccggggt aaggaccatc    2580
accacggGtg cccccatcac gtactccacc tatggcaagt tcttgccga cggtggttgc     2640
tctggggcg cctatgacat cataatatgt gatgagtgcc actcaactga ctcgaccact     2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatcccat cgagaccatc     2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatggg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcccctcc accgaggacc tggttaacct actccctgct    4380
atcctctccc ctggcgccct agtcgtcggg gtcgtgtgcg cagcgatact gcgtcggcac    4440
gtgggcccag ggagggggc tgtgcagtgg atgaacggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcgggcgga cggcatcatg    4800
caaaccacct gccatgtgg agcacagatc accggacatg tgaaaacgg ttccatgagg    4860
atcgtggggc ctaggacctg tagtaacacg tggcatggaa cattccccat taacgcgtac    4920
```

```
accacgggcc cctgcacgcc ctccccggcg ccaaattatt ctagggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag     5460 tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg gggatcccg atctcagcga cgggtcttgg     5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggccccctg    6780
actaattcta aagggcagaa ctgccggtat cgccggtgcc gcgcgagcgg tgtactgacg    6840
accagctgcg gtaatacccc tcacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctgggacccc gcccaaacca gaatacgact tggagttgat aacatcatgc    7080
tcctccaatg tgtcagtcgc gcacgatgca tctggcaaaa gggtgtacta tctcacccgt    7140
gacccccacc ccccccttgc gcgggctgcg tgggagacag ctagacacac tccagtcaat    7200
tcctggctag gcaacatcat catgtatgcg cccaccttgt gggcaaggat gatcctgatg    7260
```

```
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccagggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
gcccgacccc gctggttcat gtggtgccta ctcctacttt ctgtaggggt aggcatctat    7740
ctactcccca accgatgaac ggggacctaa acactccagg ccaataggcc atcctgtttt    7800
tttccttttt tttttttctt tttttttttt tttttttttt tttttttttt ttctcctttt    7860 ttttcctct tttttccctt ttcttccctt tggtggctcc atcttagccc tagtcacggc     7920
tagctgtgaa aggtccgtga gccgcttgac tgcagagagt gctgatactg gcctctctgc    7980
agatcaagta ctcctgcagg cgcgccacta gtgggaatac gcggggtatg ccgcgtttta    8040
gcatattgac gacccaattc tcatgtttga cagcttatca tcgataagct taatgcggt     8100 agtttatcac agttaaattg ctaacgcagt caggcaccgt gtatgaaatc taacaatgcg    8160
ctcatcgtca tcctcggcac cgtcaccctg gatgctgtag gcataggctt ggttatgccg    8220
gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac acccgtcctg tggatcctct acgccggacg catcgtggcc    8460
ggcatcaccg gcgccacagg tgcggttgct ggcgcctata tcgccgacat caccgatggg    8520
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acggcctcaa cctactactg ggctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atcttgcacg ccctcgctca agccttcgtc    8940
actggtcccg ccaccaaacg tttcggcgag aagcaggcca ttatcgccgg catggcggcc    9000
gacgcgctgg gctacgtctt gctggcgttc gcgacgcgag gctggatggc cttccccatt    9060
atgattcttc tcgcttccgg cggcatcggg atgcccgcgt tgcaggccat gctgtccagg    9120
caggtagatg acgaccatca gggacagctt caaggatcgc tcgcggctct taccagccta    9180
acttcgatca ctggaccgct gatcgtcacg gcgatttatg ccgcctcggc gagcacatgg    9240
aacgggttgg catggattgt aggcgccgcc ctataccttg tctgcctccc cgcgttgcgt    9300
cgcggtgcat ggagccgggc cacctcgacc tgaatggaag ccggcggcac ctcgctaacg    9360
gattcaccac tccaagaatt ggagccaatc aattcttgcg gagaactgtg aatgcgcaaa    9420
ccaacccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
```

| | |
|---|---|
| tcggtttccg tgtttcgtaa agtctggaaa cgcggaagtc agcgccctgc accattatgt | 9720 |
| tccggatctg catcgcagga tgctgctggc taccctgtgg aacacctaca tctgtattaa | 9780 |
| cgaagcgctg gcattgaccc tgagtgattt ttctctggtc ccgccgcatc cataccgcca | 9840 |
| gttgtttacc ctcacaacgt tccagtaacc gggcatgttc atcatcagta accgtatcg | 9900 |
| tgagcatcct ctctcgtttc atcggtatca ttaccccat gaacagaaat tccccttac | 9960 |
| acggaggcat caagtgacca aacaggaaaa aaccgccctt aacatggccc gctttatcag | 10020 |
| aagccagaca ttaacgcttc tggagaaact caacgagctg gacgcggatg aacaggcaga | 10080 |
| catctgtgaa tcgcttcacg accacgctga tgagctttac cgcagctgcc tcgcgcgttt | 10140 |
| cggtgatgac ggtgaaaacc tctgacacat gcagctcccg gagacggtca cagcttgtct | 10200 |
| gtaagcggat gccgggagca gacaagcccg tcagggcgcg tcagcgggtg ttggcgggtg | 10260 |
| tcggggcgca gccatgaccc agtcacgtag cgatagcgga gtgtatactg gcttaactat | 10320 |
| gcggcatcag agcagattgt actgagagtg caccatatgc ggtgtgaaat accgcacaga | 10380 |
| tgcgtaagga gaaaataccg catcaggcgc tcttccgctt cctcgctcac tgactcgctg | 10440 |
| cgctcggtcg ttcggctgcg gcgagcggta tcagctcact caaaggcggt aatacggtta | 10500 |
| tccacagaat caggggataa cgcaggaaag aacatgtgag caaaaggcca gcaaaaggcc | 10560 |
| aggaaccgta aaaaggccgc gttgctggcg ttttttccata ggctccgccc ccctgacgag | 10620 |
| catcacaaaa atcgacgctc aagtcagagg tggcgaaacc cgacaggact ataaagatac | 10680 |
| caggcgtttc cccctggaag ctccctcgtg cgctctcctg ttccgaccct gccgcttacc | 10740 |
| ggatacctgt ccgcctttct cccttcggga agcgtggcgc tttctcatag ctcacgctgt | 10800 |
| aggtatctca gttcggtgta ggtcgttcgc tccaagctgg gctgtgtgca cgaaccccc | 10860 |
| gttcagcccg accgctgcgc cttatccggt aactatcgtc ttgagtccaa cccggtaaga | 10920 |
| cacgacttat cgccactggc agcagccact ggtaacagga ttagcagagc gaggtatgta | 10980 |
| ggcggtgcta cagagttctt gaagtggtgg cctaactacg gctacactag aaggacagta | 11040 |
| tttggtatct gcgctctgct gaagccagtt accttcggaa aaagagttgg tagctcttga | 11100 |
| tccggcaaac aaaccaccgc tggtagcggt ggtttttttg tttgcaagca gcagattacg | 11160 |
| cgcagaaaaa aaggatctca agaagatcct ttgatctttt ctacggggtc tgacgctcag | 11220 |
| tggaacgaaa actcacgtta agggattttg gtcatgagat tatcaaaaag gatcttcacc | 11280 |
| tagatccttt tctagataat acgactcact ata | 11313 |

<210> SEQ ID NO 3
<211> LENGTH: 11313
<212> TYPE: DNA
<213> ORGANISM: Artificial Sequence
<220> FEATURE:
<223> OTHER INFORMATION: Plasmid

<400> SEQUENCE: 3

| | |
|---|---|
| gccagccccc gattgggggc gacactccac catagatcac tccctgtga ggaactactg | 60 |
| tcttcacgca gaaagcgtct agccatggcg ttagtatgag tgtcgtgcag cctccaggac | 120 |
| cccccctccc gggagagcca tagtggtctg cggaaccggt gagtacaccg gaattgccag | 180 |
| gacgaccggg tcctttcttg gatcaaccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |

```
ctcaaagaaa aaccaaaggg cgcgccatga ttgaacaaga tggattgcac gcaggttctc      420
cggccgcttg ggtggagagg ctattcggct atgactgggc acaacagaca atcggctgct      480
ctgatgccgc cgtgttccgg ctgtcagcgc aggggcgccc ggttcttttt gtcaagaccg      540
acctgtccgg tgccctgaat gaactgcagg acgaggcagc gcggctatcg tggctggcca      600
cgacgggcgt tccttgcgca gctgtgctcg acgttgtcac tgaagcggga agggactggc      660
tgctattggg cgaagtgccg gggcaggatc tcctgtcatc tcaccttgct cctgccgaga      720
aagtatccat catggctgat gcaatgcggc ggctgcatac gcttgatccg gctacctgcc      780
cattcgacca ccaagcgaaa catcgcatcg agcgagcacg tactcggatg gaagccggtc      840
ttgtcgatca ggatgatctg gacgaagagc atcaggggct cgcgccagcc gaactgttcg      900
ccaggctcaa ggcgcgcatg cccgacgcg aggatctcgt cgtgacccat ggcgatgcct      960
gcttgccgaa tatcatggtg gaaaatggcc gcttttctgg attcatcgac tgtggccggc     1020
tgggtgtggc ggaccgctat caggacatag cgttggctac ccgtgatatt gctgaagagc     1080
ttggcggcga atgggctgac cgcttcctcg tgctttacgg tatcgccgct cccgattcgc     1140
agcgcatcgc cttctatcgc cttcttgacg agttcttctg agtttaaaca gaccacaacg     1200
gtttccctct agcgggatca attccgcccc tctccctccc cccccctaa cgttactggc      1260 cgaagccgct tggaataagg ccggtgtgcg tttgtctata tgttattttc caccatattg     1320
ccgtcttttg gcaatgtgag ggcccggaaa cctggccctg tcttcttgac gagcattcct     1380
aggggtcttt cccctctcgc caaggaatg caaggtctgt tgaatgtcgt gaaggaagca     1440
gttcctctgg aagcttcttg aagacaaaca acgtctgtag cgaccctttg caggcagcgg     1500 aacccccac ctggcgacag gtgcctctgc ggccaaaagc cacgtgtata agatacacct     1560
gcaaaggcgg cacaacccca gtgccacgtt gtgagttgga tagttgtgga aagagtcaaa     1620
tggctctcct caagcgtatt caacaagggg ctgaaggatg cccagaaggt accccattgt     1680
atgggatctg atctggggcc tcggtgcaca tgctttacat gtgtttagtc gaggttaaaa     1740
aacgtctagg ccccccgaac cacggggacg tggttttcct ttgaaaaaca cgataatacc     1800
atggcgccta ttacggccta ctcccaacag acgcgaggcc tacttggctg catcatcact     1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc     1980
ggctcaaaga cccttgccgg cccaaagggc ccaatcaccc aaatgtacac caatgtggac     2040
caggacctcg tcgctggca agcgccccc ggggcgcgtt ccttgacacc atgcacctgc      2100
ggcagctcgg acctttactt ggtcacgagg catgccgatg tcattccggt gcgccggcgg     2160
ggcgacagca ggggagcct actctccccc aggcccgtct cctacttgaa gggctcttcg     2220
ggcggtccac tgctctgccc ctcggggcac gctgtgggca tctttcgggc tgccgtgtgc     2280
acccgagggg ttgcgaaggc ggtggacttt gtacccgtcg agtctatgga aaccactatg     2340
cggtccccgg tcttcacgga caactcgtcc cctccggccg taccgcagac attccaggtg     2400
gcccatctac acgcccctac tggtagcggc aagagcacta aggtgccggc tgcgtatgca     2460
gcccaagggt ataaggtgct tgtcctgaac ccgtccgtcg ccgccaccct aggtttcggg     2520
gcgtatatgt ctaaggcaca tggtatcgac cctaacatca gaaccggggt aaggaccatc     2580
accacgggtg cccccatcac gtactccacc tatggcaagt tccttgccga cggtggttgc     2640
tctgggggcg cctatgacat cataatatgt gatgagtgcc actcaactga ctcgaccact     2700
atcctgggca tcggcacagt cctggaccaa gcggagacgg ctggagcgcg actcgtcgtg     2760
```

```
ctcgccaccg ctacgcctcc gggatcggtc accgtgccac atccaaacat cgaggaggtg    2820
gctctgtcca gcactggaga atccccttt tatggcaaag ccatccccat cgagaccatc     2880 aagggggga ggcacctcat tttctgccat tccaagaaga aatgtgatga gctcgccgcg     2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga     3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttccctac    3480 ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcagctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtctttta ccgggagttc    3840
gatgagatgg aagagtgcgc ctcacacctc ccttacatcg aacggggaat gcagctcgcc    3900
gaacatttca acagaaggc aatcgggttg ctgcaaacag ccaccaagca agcggaggct    3960
gctgctcccg cggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag gggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaacgg ttccatgagg     4860 atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtggggatt tccactacgt gacgggcatg     5040
accactgaca acgtaaagtg cccgtgtcag gttccggccc ccgaattctt cacagaagtg    5100
```

```
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag agatgggcg gaacatcac ccgcgtggag      5460
tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac cttttgacaga ctgcaggtcc tggacgacca ctaccgggac   6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg    6360
ctggaagaca ctgagacacc aattgacacc accatcatgg caaaaaatga ggttttctgc    6420
gtccaaccag agaaggggg ccgcaagcca gctcgcctta tcgtattccc agatttgggg    6480
gttcgtgtgt gcgagaaaat ggcccttttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccctg     6780
actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctgggacccc gcccaaacca gaatacgact ggagttgat aacatcatgc    7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catgccctta gcgcattttc actccatagt tactctccag gtgagatcaa tagggtggct    7440
tcatgcctca ggaaacttgg ggtaccgccc ttgcgagtct ggagacatcg ggccagaagt    7500
```

```
gtccgcgcta ggctactgtc ccagggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt    7680
gcccgacccc gctggttcat gtggtgccta ctcctacttt ctgtaggggt aggcatctat    7740
ctactcccca accgatgaac ggggacctaa acactccagg ccataggcc atcctgtttt    7800 tttcccttt tttttttctt tttttttttt tttttttttt tttttttttt ttctcctttt    7860
tttttcctct tttttccctt ttctttcctt tggtggctcc atcttagccc tagtcacggc    7920
tagctgtgaa aggtccgtga ccgcttgac tgcagagagt gctgatactg gcctctctgc    7980
agatcaagta ctcctgcagg cgcgccacta gtgggaatac gcggggtatg ccgcgtttta    8040
gcatattgac gacccaattc tcatgtttga cagcttatca tcgataagct ttaatgcggt    8100
agtttatcac agttaaattg ctaacgcagt caggcaccgt gtatgaaatc taacaatgcg    8160
ctcatcgtca tcctcggcac cgtcaccctg gatgctgtag gcataggctt ggttatgccg    8220
gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac acccgtcctg tggatcctct acgccggacg catcgtggcc    8460
ggcatcaccg gcgccacagg tgcggttgct ggcgcctata tcgccgacat caccgatggg    8520
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acggcctcaa cctactactg ggctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atccttcacg ccctcgctca agccttcgtc    8940
actggtcccg ccaccaaacg tttcggcgag aagcaggcca ttatcgccgg catggcggcc    9000
gacgcgctgg gctacgtctt gctggcgttc gcgacgcgag gctggatggc cttccccatt    9060
atgattcttc tcgcttccgg cggcatcggg atgcccgcgt tgcaggccat gctgtccagg    9120
caggtagatg acgaccatca gggacagctt caaggatcgc tcgcggctct taccagccta    9180
acttcgatca ctggaccgct gatcgtcacg gcgatttatg ccgcctcggc gagcacatgg    9240
aacgggttgg catggattgt aggcgccgcc ctataccttg tctgcctccc gcgttgcgt    9300 cgcggtgcat ggagccgggc cacctcgacc tgaatggaag ccggcggcac ctcgctaacg    9360
gattcaccac tccaagaatt ggagccaatc aattcttgcg gagaactgtg aatgcgcaaa    9420
ccaacccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc cataccgcca    9840
```

```
gttgtttacc ctcacaacgt tccagtaacc gggcatgttc atcatcagta acccgtatcg    9900
tgagcatcct ctctcgtttc atcggtatca ttaccccat gaacagaaat tccccttac     9960 acggaggcat caagtgacca acaggaaaa aaccgcctt aacatggccc gctttatcag    10020
aagccagaca ttaacgcttc tggagaaact caacgagctg acgcggatg aacaggcaga   10080 catctgtgaa tcgcttcacg accacgctga tgagctttac cgcagctgcc tcgcgcgttt  10140
cggtgatgac ggtgaaaacc tctgacacat gcagctcccg gagacggtca cagcttgtct  10200
gtaagcggat gccgggagca gacaagcccg tcagggcgcg tcagcgggtg ttggcgggtg  10260
tcggggcgca gccatgaccc agtcacgtag cgatagcgga gtgtatactg gcttaactat  10320
gcggcatcag agcagattgt actgagagtg caccatatgc ggtgtgaaat accgcacaga  10380
tgcgtaagga gaaaataccg catcaggcgc tcttccgctt cctcgctcac tgactcgctg  10440
cgctcggtcg ttcggctgcg gcgagcggta tcagctcact caaaggcggt aatacggtta  10500
tccacagaat caggggataa cgcaggaaag aacatgtgag caaaaggcca gcaaaaggcc  10560
aggaaccgta aaaaggccgc gttgctggcg ttttccata ggctccgccc ccctgacgag   10620
catcacaaaa atcgacgctc aagtcagagg tggcgaaacc cgacaggact ataaagatac  10680
caggcgtttc ccctggaag ctccctcgtg cgctctcctg ttccgaccct gccgcttacc   10740
ggatacctgt ccgcctttct cccttcggga agcgtggcgc tttctcatag ctcacgctgt  10800
aggtatctca gttcggtgta ggtcgttcgc tccaagctgg gctgtgtgca cgaaccccc   10860 gttcagcccg accgctgcgc cttatccggt aactatcgtc ttgagtccaa cccggtaaga  10920
cacgacttat cgccactggc agcagccact ggtaacagga ttagcagagc gaggtatgta  10980
ggcggtgcta cagagttctt gaagtggtgg cctaactacg gctacactag aaggacagta  11040
tttggtatct gcgctctgct gaagccagtt accttcggaa aaagagttgg tagctcttga  11100
tccggcaaac aaaccaccgc tggtagcggt ggtttttttg tttgcaagca gcagattacg  11160
cgcagaaaaa aaggatctca agaagatcct ttgatctttt ctacggggtc tgacgctcag  11220
tggaacgaaa actcacgtta agggattttg gtcatgagat tatcaaaaag gatcttcacc  11280
tagatccttt tctagataat acgactcact ata                              11313
```

<210> SEQ ID NO 4
<211> LENGTH: 11313
<212> TYPE: DNA
<213> ORGANISM: Artificial Sequence
<220> FEATURE:
<223> OTHER INFORMATION: Plasmid

<400> SEQUENCE: 4

```
gccagccccc gattggggc gacactccac catagatcac tcccctgtga ggaactactg      60
tcttcacgca gaaagcgtct agccatggcg ttagtatgag tgtcgtgcag cctccaggac    120 ccccctccc gggagagcca tagtggtctg cggaaccggt gagtacaccg gaattgccag     180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaagggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc agggggcccc ggttcttttt gtcaagaccg    540
acctgtccgg tgccctgaat gaactgcagg acgaggcagc gcggctatcg tggctggcca    600
```

```
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc ccccccctaa cgttactggc   1260
cgaagccgct tggaataagg ccggtgtgcg tttgtctata tgttatttt caccatattg   1320
ccgtcttttg gcaatgtgag ggcccggaaa cctggccctg tcttcttgac gagcattcct   1380
aggggtcttt cccctctcgc caaggaatg caaggtctgt tgaatgtcgt gaaggaagca   1440
gttcctctgg aagcttcttg aagacaaaca acgtctgtag cgaccctttg caggcagcgg   1500
aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctggggcc tcggtgcaca tgctttacat gtgtttagtc gaggttaaaa   1740
aacgtctagg ccccccgaac cacggggacg tggttttcct ttgaaaaaca cgataatacc   1800
atggcgccta ttacggccta ctcccaacag acgcgaggcc tacttggctg catcatcact   1860
agcctcacag gccgggacag gaaccaggtc gaggggagg tccaagtggt ctccaccgca   1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgcccccc ggggcgcgtt ccttgacacc atgcacctgc   2100
ggcagcgcgg acctttactt ggtcacgagg catgccgatg tcattccggt gcgccggcgg   2160
ggcgacagca gggggagcct actctccccc aggcccgttt cctacttgaa gggctcttcg   2220
ggcggtccac tgctctgccc ctcggggcac gctgtgggca tctttcgggc tgccgtgtgc   2280
acccgagggg ttgcgaaggc ggtggacttt gtaccgtcg agtctatggg aaccactatg   2340
cggtcccccg tcttcacgga caactcgtcc cctccggccg taccgcagac attccaggtg   2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacgggtg cccccatcac gtactccacc tatggcaagt tcttgccga cggtggttgc   2640
tctgggggcg cctatgacat cataatatgt gatgagtgcc actcaactga ctcgaccact   2700
atcctgggca tcggcacagt cctggaccaa gcgagacgg ctggagcgcg actcgtcgtg   2760
ctcgccaccg ctacgcctcc gggatcggtc accgtgccac atccaaacat cgaggaggtg   2820
gctctgtcca gcactggaga aatccccttt tatggcaaag ccatccccat cgagaccatc   2880
aagggggga ggcacctcat tttctgccat tccaagaaga atgtgatga gctcgccgcg   2940
```

```
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg taggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360 ccaggggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gcccctgctg   3600
tataggctgg gagccgttca aaacgaggtt actaccacac accccataac caaatacatc   3660
atggcatgca tgtcagctga cctggaggtc gtcacgagca cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtctttta ccgggagttc   3840
gatgagatga agagtgcgc ctcacacctc ccttacatcg aacggggaat gcagctcgcc   3900
gaacatttca acagaaggc aatcgggttg ctgcaaacag ccaccaagca agcggaggct   3960
gctgctcccg cggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct ggggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgcccctcc accgaggacc tggttaacct actccctgct   4380
atcctctccc ctggcgccct agtcgtcggg gtcgtgtgcg cagcgatact gcgtcggcac   4440
gtgggcccag gggagggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagg agtacgtgga ggttacgcgg gtgggggatt ccactacgt gacgggcatg   5040 accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgaccct cccacattac ggcggagacg   5280
gctaagcgta ggctggccag gggatctccc cctcccttgg ccagctcatc agctatccag   5340
```

```
ctgtctgcgc cttccttgaa ggcaacatgc actacccgtc atgactcccc ggacgctgac    5400
ctcatcgagg ccaacctcct gtggcggcag agatgggcg ggaacatcac ccgcgtggag    5460
tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatccg cagcgcaagc    6120 ctgcggcaga agaaggtcac cttttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg    6360 ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggccccctg    6780
actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctggggaccc gcccaaacca gaatacgact tggagttgat aacatcatgc    7080
tcctccaatg tgtcagtcgc gcacgatgca tctggcaaaa gggtgtacta tctcacccgt    7140
gaccccacca cccccccttgc gcgggctgcg tgggagacag ctagacacac tccagtcaat    7200
tcctggctag caacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg gccagaagt    7500 gtccgcgcta ggctactgtc ccagggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
```

```
gcccgacccc gctggttcat gtggtgccta ctcctacttt ctgtaggggt aggcatctat    7740
ctactcccca accgatgaac ggggacctaa acactccagg ccaataggcc atcctgtttt    7800 tttcccttt ttttttttctt tttttttttt tttttttttt tttttttttt ttctcctttt    7860
tttttcctct ttttttcctt ttctttcctt tggtggctcc atcttagccc tagtcacggc    7920
tagctgtgaa aggtccgtga gccgcttgac tgcagagagt gctgatactg gcctctctgc    7980
agatcaagta ctcctgcagg cgcgccacta gtgggaatac gcggggtatg ccgcgtttta    8040
gcatattgac gacccaattc tcatgtttga cagcttatca tcgataagct ttaatgcggt    8100
agtttatcac agttaaattg ctaacgcagt caggcaccgt gtatgaaatc taacaatgcg    8160
ctcatcgtca tcctcggcac cgtcaccctg gatgctgtag cataggctt ggttatgccg    8220 gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac acccgtcctg tggatcctct acgccggacg catcgtggcc    8460
ggcatcaccg gcgccacagg tgcggttgct ggcgcctata tcgccgacat caccgatggg    8520
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acggcctcaa cctactactg ggctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atcttgcacg ccctcgctca agccttcgtc    8940
actggtcccg ccaccaaacg tttcggcgag aagcaggcca ttatcgccgg catggcggcc    9000
gacgcgctgg gctacgtctt gctggcgttc gcgacgcgag gctggatggc cttccccatt    9060
atgattcttc tcgcttccgg cggcatcggg atgcccgcgt tgcaggccat gctgtccagg    9120
caggtagatg acgaccatca gggacagctt caaggatcgc tcgcggctct taccagccta    9180
acttcgatca ctggaccgct gatcgtcacg gcgatttatg ccgcctcggc gagcacatgg    9240
aacgggttgg catggattgt aggcgccgcc ctataccttg tctgcctccc cgcgttgcgt    9300
cgcggtgcat ggagccgggc cacctcgacc tgaatggaag ccggcggcac ctcgctaacg    9360
gattcaccac tccaagaatt ggagccaatc aattcttgcg gagaactgtg aatgcgcaaa    9420 ccaaccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgaccta gcaacaaca tgaatggtct    9660 tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc cataccgcca    9840
gttgtttacc ctcacaacgt tccagtaacc gggcatgttc atcatcagta acccgtatcg    9900
tgagcatcct ctctcgtttc atcggtatca ttaccccccat gaacagaaat tcccccttac    9960
acggaggcat caagtgacca aacaggaaaa aacgcgcctt aacatggccc gctttatcag   10020
aagccagaca ttaacgcttc tggagaaact caacgagctg gacgcggatg aacaggcaga   10080
```

```
catctgtgaa tcgcttcacg accacgctga tgagctttac cgcagctgcc tcgcgcgttt    10140
cggtgatgac ggtgaaaacc tctgacacat gcagctcccg agacggtca cagcttgtct    10200 gtaagcggat gccgggagca gacaagcccg tcagggcgcg tcagcgggtg ttggcgggtg    10260
tcggggcgca gccatgaccc agtcacgtag cgatagcgga gtgtatactg gcttaactat    10320
gcggcatcag agcagattgt actgagagtg caccatatgc ggtgtgaaat accgcacaga    10380
tgcgtaagga gaaaataccg catcaggcgc tcttccgctt cctcgctcac tgactcgctg    10440
cgctcggtcg ttcggctgcg gcgagcggta tcagctcact caaaggcggt aatacggtta    10500
tccacagaat caggggataa cgcaggaaag aacatgtgag caaaaggcca gcaaaaggcc    10560
aggaaccgta aaaaggccgc gttgctggcg ttttccata ggctccgccc cctgacgag     10620 catcacaaaa atcgacgctc aagtcagagg tggcgaaacc cgacaggact ataaagatac    10680
caggcgtttc ccctggaag ctccctcgtg cgctctcctg ttccgaccct gccgcttacc    10740
ggatacctgt ccgcctttct cccttcggga agcgtggcgc tttctcatag ctcacgctgt    10800
aggtatctca gttcggtgta ggtcgttcgc tccaagctgg gctgtgtgca cgaaccccc     10860 gttcagcccg accgctgcgc cttatccggt aactatcgtc ttgagtccaa cccggtaaga    10920
cacgacttat cgccactggc agcagccact ggtaacagga ttagcagagc gaggtatgta    10980
ggcggtgcta cagagttctt gaagtggtgg cctaactacg gctacactag aaggacagta    11040
tttggtatct gcgctctgct gaagccagtt accttcggaa aaagagttgg tagctcttga    11100
tccggcaaac aaaccaccgc tggtagcggt ggtttttttg tttgcaagca gcagattacg    11160
cgcagaaaaa aaggatctca agaagatcct ttgatctttt ctacggggtc tgacgctcag    11220
tggaacgaaa actcacgtta agggattttg gtcatgagat tatcaaaaag gatcttcacc    11280
tagatccttt tctagataat acgactcact ata                                 11313
```

<210> SEQ ID NO 5
<211> LENGTH: 11313
<212> TYPE: DNA
<213> ORGANISM: Artificial Sequence
<220> FEATURE:
<223> OTHER INFORMATION: Plasmid

<400> SEQUENCE: 5

```
gccagccccc gattggggc gacactccac catagatcac tcccctgtga ggaactactg      60
tcttcacgca gaaagcgtct agccatggcg ttagtatgag tgtcgtgcag cctccaggac    120 ccccctccc gggagagcca tagtggtctg cggaaccggt gagtacaccg gaattgccag    180
gacgaccggg tccttcttg gatcaaccc ctcaatgcct ggagatttgg gcgtgccccc     240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaagggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc agggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
```

```
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc    1260 cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
gttcctctgg aagcttcttg aagacaaaca acgtctgtag cgacccttg caggcagcgg    1500 aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctggggcc tcggtgcaca tgctttacat gtgtttagtc gaggttaaaa   1740
aacgtctagg ccccccgaac cacggggacg tggttttcct ttgaaaaaca cgataatacc   1800
atggcgccta ttacggccta ctcccaacag acgcgaggcc tacttggctg catcatcact   1860
agcctcacag gccgggacag gaaccaggtc gagggggagg tccaagtggt ctccaccgca   1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgccccc ggggcgcgtt ccttgacacc atgcacctgc    2100
ggcagctcgg acctttactt ggtcacgagg catgccgatg tcattccggt cgccggcgg    2160 ggcgacagca gggggagcct actctccccc aggcccgtct cctacttgaa gggtctcttcg   2220 ggcggtccac tgctctgccc ctcggggcac gctgtgggca tctttcgggc tgccgtgtgc   2280
acccgagggg ttgcgaaggc ggtggactt gtaccgtcg agtctatggg aaccactatg     2340
cggtccccgg tcttcacgga caactcgtcc cctccggccg taccgcagac attccaggtg   2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacgggtg cccccatcac gtactccacc tatgcaagt tcttgccga cggtggttgc     2640 tctggggcg cctatgacat cataatatgt gatgagtgcc actcaactga ctcgaccact    2700
atcctgggca tcggcacagt cctggaccaa gcggagacgc tggagcgcg actcgtcgtg    2760 ctcgccaccg ctacgcctcc gggatcggtc accgtgccac atccaaacat cgaggaggtg   2820
gctctgtcca gcactggaga atccccttt tatggcaaag ccatcccat cgagaccatc      2880 aagggggggga ggcacctcat tttctgccat tccaagaaga aatgtgatga gctcgccgcg   2940
aagctgtccg gcctcggact caatgctgta gcatattacc ggggccttga tgtatccgtc    3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
```

```
cagcggcgag gcaggactgg tagggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcagctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtctttta ccgggagttc    3840
gatgagatgg aagagtgcgc ctcacacctc ccttacatcg aacggggaat gcagctcgcc    3900
gaacatttca acagaaggc aatcgggttg ctgcaaacag ccaccaagca agcggaggct    3960
gctgctcccg cggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcccctcc accgaggacc tggttaacct actccctgct    4380
atcctctccc ctggcgccct agtcgtcggg gtcgtgtgcg cagcgatact gcgtcggcac    4440
gtgggcccag ggggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtcccctcct tctcatgtca acgtgggtac aagggagtct ggcggggcga cggcatcatg    4800
caaaccacct gccatgtgg agcacagatc accggacatg tgaaaaacgg ttccatgagg    4860
atcgtggggc ctaggacctg tagtaacacg tggcatggaa cattcccccat taacgcgtac    4920
accacgggcc cctgcacgcc ctccccggcg ccaaattatt ctagggcgct gtggcgggtg    4980
gctgctgagg agtacgtgga ggttacgcgg gtgggggatt ccactacgt gacgggcatg    5040
accactgaca acgtaaagtg cccgtgtcag gttccggccc cgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc cctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460
tcagaaaata aggtagtaat tttggagtct ttcgagccgc tccaagcgga ggaggatgag    5520
```

| | | | | |
|---|---|---|---|---|
| agggaagtat | ccgttccggc | ggagatcctg | cggaggtcca | ggaaattccc tcgagcgatg | 5580 |
| cccatatggg | cacgcccgga | ttacaaccct | ccactgttag | agtcctggaa ggacccggac | 5640 |
| tacgtccctc | cagtggtaca | cgggtgtcca | ttgccgcctg | ccaaggcccc tccgatacca | 5700 |
| cctccacgga | ggaagaggac | ggttgtcctg | tcagaatcta | ccgtgtcttc tgccttggcg | 5760 |
| gagctcgcca | caaagacctt | cggcagctcc | gaatcgtcgg | ccgtcgacag cggcacggca | 5820 |
| acggcctctc | ctgaccagcc | ctccgacgac | ggcgacgcgg | gatccgacgt tgagtcgtac | 5880 |
| tcctccatgc | ccccccttga | ggggagccg | ggggatcccg | atctcagcga cgggtcttgg | 5940 |
| tctaccgtaa | gcgaggaggc | tagtgaggac | gtcgtctgct | gctcgatgtc ctacacatgg | 6000 |
| acaggcgccc | tgatcacgcc | atgcgctgcg | gaggaaacca | agctgcccat caatgcactg | 6060 |
| agcaactctt | tgctccgtca | ccacaacttg | gtctatgcta | caacatctcg cagcgcaagc | 6120 |
| ctgcggcaga | agaaggtcac | ctttgacaga | ctgcaggtcc | tggacgacca ctaccgggac | 6180 |
| gtgctcaagg | agatgaaggc | gaaggcgtcc | acagttaagg | ctaaacttct atccgtggag | 6240 |
| gaagcctgta | agctgacgcc | cccacattcg | gccagatcta | aatttggcta tggggcaaag | 6300 |
| gacgtccgga | acctatccag | caaggccgtt | aaccacatcc | gctccgtgtg gaaggacttg | 6360 |
| ctggaagaca | ctgagacacc | aattgacacc | accatcatgg | caaaaaatga ggttttctgc | 6420 |
| gtccaaccag | agaagggggg | ccgcaagcca | gctcgcctta | tcgtattccc agatttgggg | 6480 |
| gttcgtgtgt | gcgagaaaat | ggcccttac | gatgtggtct | ccaccctccc tcaggccgtg | 6540 |
| atgggctctt | catacggatt | ccaatactct | cctggacagc | gggtcgagtt cctggtgaat | 6600 |
| gcctggaaag | cgaagaaatg | ccctatgggc | ttcgcatatg | acacccgctg ttttgactca | 6660 |
| acggtcactg | agaatgacat | ccgtgttgag | gagtcaatct | accaatgttg tgacttggcc | 6720 |
| cccgaagcca | gacaggccat | aaggtcgctc | acagagcggc | tttacatcgg gggcccctg | 6780 |
| actaattcta | aagggcagaa | ctgccggcat | cgccggtgcc | gcgcgagcgg tgtactgacg | 6840 |
| accagctgcg | gtaatacccct | cacatgttac | ttgaaggccg | ctgcggcctg tcgagctgcg | 6900 |
| aagctccagg | actgcacgat | gctcgtatgc | ggagacgacc | ttgtcgttat ctgtgaaagc | 6960 |
| gcggggaccc | aagaggacga | ggcgagccta | cgggccttca | cggaggctat gactagatac | 7020 |
| tctgccccc | ctggggaccc | gcccaaacca | gaatacgact | tggagttgat aacatcatgc | 7080 |
| tcctccaatg | tgtcagtcgc | gcacgatgca | tctggcaaaa | gggtgtacta tctcacccgt | 7140 |
| gaccccacca | ccccccttgc | gcgggctgcg | tgggagacag | ctagacacac tccagtcaat | 7200 |
| tcctggctag | gcaacatcat | catgtatgcg | cccaccttgt | gggcaaggat gatcctgatg | 7260 |
| actcatttct | tctccatcct | tctagctcag | gaacaacttg | aaaaagccct agattgtcag | 7320 |
| atctacgggg | cctgttactc | cattgagcca | cttgacctac | ctcagatcat tcaacgactc | 7380 |
| catggcctta | gcgcatttc | actccatagt | tactctccag | gtgagatcaa tagggtggct | 7440 |
| tcatgcctca | ggaaacttgg | ggtaccgccc | ttgcgagtct | ggagacatcg ggccagaagt | 7500 |
| gtccgcgcta | ggctactgtc | ccaggggggg | agggctgcca | cttgtggcaa gtacctcttc | 7560 |
| aactgggcag | taaggaccaa | gctcaaactc | actccaatcc | cggctgcgtc ccagttggat | 7620 |
| ttatccagct | ggttcgttgc | tggttacagc | ggggagaca | tatatcacag cctgtctcgt | 7680 |
| gcccgacccc | gctggttcat | gtggtgccta | ctcctacttt | ctgtagggt aggcatctat | 7740 |
| ctactcccca | accgatgaac | ggggacctaa | acactccagg | ccaataggcc atcctgtttt | 7800 |
| tttcccttt | tttttttctt | tttttttttt | tttttttttt | tttttttttt ttctcctttt | 7860 |
| tttttcctct | tttttttcctt | ttctttcctt | tggtggctcc | atcttagccc tagtcacggc | 7920 |

-continued

| | |
|---|---|
| tagctgtgaa aggtccgtga gccgcttgac tgcagagagt gctgatactg gcctctctgc | 7980 |
| agatcaagta ctcctgcagg cgcgccacta gtgggaatac gcggggtatg ccgcgtttta | 8040 |
| gcatattgac gacccaattc tcatgtttga cagcttatca tcgataagct ttaatgcggt | 8100 |
| agtttatcac agttaaattg ctaacgcagt caggcaccgt gtatgaaatc taacaatgcg | 8160 |
| ctcatcgtca tcctcggcac cgtcaccctg gatgctgtag cataggctt ggttatgccg | 8220 |
| gtactgccgg gcctcttgcg ggatatcgtc cattccgaca gcatcgccag tcactatggc | 8280 |
| gtgctgctag cgctatatgc gttgatgcaa tttctatgcg cacccgttct cggagcactg | 8340 |
| tccgaccgct ttggccgccg cccagtcctg ctcgcttcgc tacttggagc cactatcgac | 8400 |
| tacgcgatca tggcgaccac acccgtcctg tggatcctct acgccggacg catcgtggcc | 8460 |
| ggcatcaccg cgccacagg tgcggttgct ggcgcctata tcgccgacat caccgatggg | 8520 |
| gaagatcggg ctcgccactt cgggctcatg agcgcttgtt tcggcgtggg tatggtggca | 8580 |
| ggccccgtgg ccgggggact gttgggcgcc atctccttgc atgcaccatt ccttgcggcg | 8640 |
| gcggtgctca acggcctcaa cctactactg gctgcttcc taatgcagga gtcgcataag | 8700 |
| ggagagcgtc gaccgatgcc cttgagagcc ttcaacccag tcagctcctt ccggtgggcg | 8760 |
| cggggcatga ctatcgtcgc cgcacttatg actgtcttct ttatcatgca actcgtagga | 8820 |
| caggtgccgg cagcgctctg ggtcattttc ggcgaggacc gctttcgctg gagcgcgacg | 8880 |
| atgatcggcc tgtcgcttgc ggtattcgga atcttgcacg ccctcgctca agccttcgtc | 8940 |
| actggtcccg ccaccaaacg tttcggcgag aagcaggcca ttatcgccgg catggcggcc | 9000 |
| gacgcgctgg gctacgtctt gctggcgttc gcgacgcgag gctggatggc cttccccatt | 9060 |
| atgattcttc tcgcttccgg cggcatcggg atgcccgcgt tgcaggccat gctgtccagg | 9120 |
| caggtagatg acgaccatca gggacagctt caaggatcgc tcgcggctct taccagccta | 9180 |
| acttcgatca ctggaccgct gatcgtcacg gcgatttatg ccgcctcggc gagcacatgg | 9240 |
| aacgggttgg catggattgt aggcgccgcc ctataccttg tctgcctccc cgcgttgcgt | 9300 |
| cgcggtgcat ggagccgggc cacctcgacc tgaatgaag ccggcggcac ctcgctaacg | 9360 |
| gattcaccac tccaagaatt ggagccaatc aattcttgcg gagaactgtg aatgcgcaaa | 9420 |
| ccaacccttg gcagaacata tccatcgcgt ccgccatctc cagcagccgc acgcggcgca | 9480 |
| tctcgggcag cgttgggtcc tggccacggg tgcgcatgat cgtgctcctg tcgttgagga | 9540 |
| cccggctagc ctggcgggt tgccttactg gttagcagaa tgaatcaccg atacgcgagc | 9600 |
| gaacgtgaag cgactgctgc tgcaaaacgt ctgcgacctg agcaacaaca tgaatggtct | 9660 |
| tcggtttccg tgtttcgtaa agtctggaaa cgcggaagtc agcgccctgc accattatgt | 9720 |
| tccggatctg catcgcagga tgctgctggc taccctgtgg aacacctaca tctgtattaa | 9780 |
| cgaagcgctg gcattgaccc tgagtgattt ttctctggtc ccgccgcatc cataccgcca | 9840 |
| gttgtttacc ctcacaacgt tccagtaacc gggcatgttc atcatcagta acccgtatcg | 9900 |
| tgagcatcct ctctcgtttc atcggtatca ttaccccccat gaacagaaat tccccccttac | 9960 |
| acggaggcat caagtgacca aacaggaaaa aaccgcccct aacatggccc gctttatcag | 10020 |
| aagccagaca ttaacgcttc tggagaaact caacgagctg gacgcggatg aacaggcaga | 10080 |
| catctgtgaa tcgcttcacg accacgctga tgagctttac cgcagctgcc tcgcgcgttt | 10140 |
| cggtgatgac ggtgaaaacc tctgacacat gcagctcccg gagacggtca cagcttgtct | 10200 |
| gtaagcggat gccgggagca gacaagcccg tcagggcgcg tcagcgggtg ttggcgggtg | 10260 |

| | | | | |
|---|---|---|---|---|
| tcggggcgca | gccatgaccc | agtcacgtag | cgatagcgga | gtgtatactg gcttaactat | 10320 |
| gcggcatcag | agcagattgt | actgagagtg | caccatatgc | ggtgtgaaat accgcacaga | 10380 |
| tgcgtaagga | gaaaataccg | catcaggcgc | tcttccgctt | cctcgctcac tgactcgctg | 10440 |
| cgctcggtcg | ttcggctgcg | gcgagcggta | tcagctcact | caaaggcggt aatacggtta | 10500 |
| tccacagaat | caggggataa | cgcaggaaag | aacatgtgag | caaaaggcca gcaaaaggcc | 10560 |
| aggaaccgta | aaaaggccgc | gttgctggcg | tttttccata | ggctccgccc cctgacgag | 10620 |
| catcacaaaa | atcgacgctc | aagtcagagg | tggcgaaacc | cgacaggact ataaagatac | 10680 |
| caggcgtttc | cccctggaag | ctccctcgtg | cgctctcctg | ttccgaccct gccgcttacc | 10740 |
| ggatacctgt | ccgcctttct | cccttcggga | agcgtggcgc | tttctcatag ctcacgctgt | 10800 |
| aggtatctca | gttcggtgta | ggtcgttcgc | tccaagctgg | gctgtgtgca cgaaccccc | 10860 |
| gttcagcccg | accgctgcgc | cttatccggt | aactatcgtc | ttgagtccaa cccggtaaga | 10920 |
| cacgacttat | cgccactggc | agcagccact | ggtaacagga | ttagcagagc gaggtatgta | 10980 |
| ggcggtgcta | cagagttctt | gaagtggtgg | cctaactacg | gctacactag aaggacagta | 11040 |
| tttggtatct | gcgctctgct | gaagccagtt | accttcggaa | aaagagttgg tagctcttga | 11100 |
| tccggcaaac | aaaccaccgc | tggtagcggt | ggttttttg | tttgcaagca gcagattacg | 11160 |
| cgcagaaaaa | aaggatctca | agaagatcct | ttgatctttt | ctacggggtc tgacgctcag | 11220 |
| tggaacgaaa | actcacgtta | agggattttg | gtcatgagat | tatcaaaaag gatcttcacc | 11280 |
| tagatccttt | tctagataat | acgactcact | ata | | 11313 |

<210> SEQ ID NO 6
<211> LENGTH: 11313
<212> TYPE: DNA
<213> ORGANISM: Artificial Sequence
<220> FEATURE:
<223> OTHER INFORMATION: Plasmid

<400> SEQUENCE: 6

| | | | | |
|---|---|---|---|---|
| gccagccccc | gattgggggc | gacactccac | catagatcac | tcccctgtga ggaactactg | 60 |
| tcttcacgca | gaaagcgtct | agccatggcg | ttagtatgag | tgtcgtgcag cctccaggac | 120 |
| cccccctccc | gggagagcca | tagtggtctg | cggaaccggt | gagtacaccg gaattgccag | 180 |
| gacgaccggg | tcctttcttg | gatcaacccg | ctcaatgcct | ggagatttgg gcgtgccccc | 240 |
| gcgagactgc | tagccgagta | gtgttgggtc | gcgaaaggcc | ttgtggtact gcctgatagg | 300 |
| gtgcttgcga | gtgccccggg | aggtctcgta | gaccgtgcac | catgagcacg aatcctaaac | 360 |
| ctcaaagaaa | aaccaaaggg | cgcgccatga | ttgaacaaga | tggattgcac gcaggttctc | 420 |
| cggccgcttg | ggtggagagg | ctattcggct | atgactggga | caacagaca atcggctgct | 480 |
| ctgatgccgc | cgtgttccgg | ctgtcagcgc | aggggcgccc | ggttcttttt gtcaagaccg | 540 |
| acctgtccgg | tgccctgaat | gaactgcagg | acgaggcagc | gcggctatcg tggctggcca | 600 |
| cgacgggcgt | tccttgcgca | gctgtgctcg | acgttgtcac | tgaagcggga agggactggc | 660 |
| tgctattggg | cgaagtgccg | gggcaggatc | tcctgtcatc | tcaccttgct cctgccgaga | 720 |
| aagtatccat | catggctgat | gcaatgcggc | ggctgcatac | gcttgatccg gctacctgcc | 780 |
| cattcgacca | ccaagcgaaa | catcgcatcg | agcgagcacg | tactcggatg gaagccggtc | 840 |
| ttgtcgatca | ggatgatctg | gacgaagagc | atcaggggct | cgcgccagcc gaactgttcg | 900 |
| ccaggctcaa | ggcgcgcatg | cccgacgcg | aggatctcgt | cgtgacccat ggcgatgcct | 960 |
| gcttgccgaa | tatcatggtg | gaaaatggcc | gcttttctgg | attcatcgac tgtggccggc | 1020 |

```
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc    1260 cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
gttcctctgg aagcttcttg aagacaaaca acgtctgtag cgacccttg caggcagcgg    1500 aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctggggcc tcggtgcaca tgctttacat gtgtttagtc gaggttaaaa   1740
aacgtctagg cccccgaac cacggggacg tggttttcct ttgaaaaaca cgataatacc    1800
atggcgccta ttacggccta ctcccaacag acgcgaggcc tacttggctg catcatcact   1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgcccccc ggggcgcgtt ccttgacacc atgcacctgc   2100
ggcagcgcgg acctttactt ggtcacgagg catgccgatg tcattccggt gcgccggcgg   2160
ggcgacagca gggggagcct actctccccc aggcccgttt cctacttgaa gggctcttcg   2220
ggcggtccac tgctctgccc ctcggggcac gctgtgggca tctttcgggc tgccgtgtgc   2280
acccgagggg ttgcgaaggc ggtggacttt gtacccgtcg agtctatggg aaccactatg   2340
cggtccccgg tcttcacgga caactcgtcc cctccggccg taccgcagac attccaggtg   2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580 accacggggtg cccccatcac gtactccacc tatggcaagt tccttgccga cggtggttgc   2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatccccttt tatggcaaag ccatccccat cgagaccatc   2880
aaggggggga ggcacctcat tttctgccat tccaagaaga atgtgatga gctcgccgcg    2940 aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg tagggcagg atgggcattt acaggtttgt gactccagga   3240 gaacggcct cggcatgtt cgattcctcg gttctgtgcg agtgctatga cgcgggctgt    3300
gcttggtacg agctcacgcc cgccgagacc tcagttaggt tgcgggctta cctaaacaca   3360
```

-continued

```
ccagggttgc ccgtctgcca ggaccatctg gagttctggg agagcgtctt tacaggcctc    3420
acccacatag acgcccattt cttgtcccag actaagcagg caggagacaa cttccctac     3480 ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcagctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtctttta ccgggagttc    3840
gatgagatgg aagagtgcgc ctcacacctc ccttacatcg aacggggaat gcagctcgcc    3900
gaacatttca aacagaaggc aatcggggttg ctgcaaacag ccaccaagca agcggaggct    3960
gctgctcccg cggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctcc accgaggacc tggttaacct actccctgct    4380
atcctctccc ctggcgccct agtcgtcggg gtcgtgtgcg cagcgatact gcgtcggcac    4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtgggggatt ccactacgt gacgggcatg    5040 accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460 tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggag ggacccggac    5640
tacgtccctc cagtggtaca cggggtgtcca ttgccgcctg ccaaggcccc tccggtacca    5700
cctccacgga ggaagaggac ggttgtcctg ccagaatcta ccgtgtcttc cgccctggcg    5760
```

```
gagctcgcca caaagacctt cggcagctcc gaatcgtcgg ccgtcgacag cggcacggca    5820
acggcctctc ctgactagcc ctccaacgac ggcgacgcgg gatccgacgt tgagtcgtac    5880
tcccccatgc ccccccttga gggggagccg ggggatcccg attccagcga cgggtcttgg    5940
tctaccgtaa gcgaggggt tagtgaggac gtcgtctgct gctcgatgtc ctacacatgg     6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac cttttgacaga ctgcaggtcc tggacgacca ctaccgggac   6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg     6360
ctggaagaca ctgagacacc aattgacacc accatcatgg caaaaaatga gttttctgc     6420
gtccaaccag agaaggggggg ccgcaagcca gctcgcctta tcgtattccc agatttgggg   6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acaccccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggcccctg     6780
actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg   6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgccccc ctggggaccc gcccaaacca gaatacgact tggagttgat aacatcatgc     7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagcccct agattgtcag   7320
atctacgggg cctgttactc cattgagcca cttgacctac ctcagatcat tcaacgactc    7380
catgccctta gcgcattttc actccatagt tactctccag gtgagatcaa tagggtggct    7440
tcatgcctca ggaaacttgg ggtaccgccc ttgcgagtct ggagacatcg gccagaagt     7500
gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt     7680
gcccgacccc gctggttcat gtggtgccta ctcctacttt ctgtaggggt aggcatctat    7740
ctactcccca accgatgaac ggggacctaa acactccagg ccaataggcc atcctgtttt    7800
tttcccttt tttttttctt tttttttttt tttttttttt tttttttttt ttctcctttt     7860
tttttcctct ttttttcctt ttcttttcctt tggtggctcc atcttagccc tagtcacggc    7920
tagctgtgaa aggtccgtga gccgcttgac tgcagagagt gctgatactg gcctctctgc    7980
agatcaagta ctcctgcagg cgcgccacta gtgggaatac gcggggtatg ccgcgtttta    8040
gcatattgac gacccaattc tcatgtttga cagcttatca tcgataagct ttaatgcggt    8100
```

```
agtttatcac agttaaattg ctaacgcagt caggcaccgt gtatgaaatc taacaatgcg    8160
ctcatcgtca tcctcggcac cgtcaccctg gatgctgtag gcataggctt ggttatgccg    8220
gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac acccgtcctg tggatcctct acgccggacg catcgtggcc    8460
ggcatcaccg cgccacagg tgcggttgct ggcgcctata tcgccgacat caccgatggg    8520
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acgcctcaa cctactactg gctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atcttgcacg ccctcgctca agccttcgtc    8940
actggtcccg ccaccaaacg tttcggcgag aagcaggcca ttatcgccgg catggcggcc    9000
gacgcgctgg gctacgtctt gctggcgttc gcgacgcgag gctggatggc cttccccatt    9060
atgattcttc tcgcttccgg cggcatcggg atgcccgcgt gcaggccat gctgtccagg    9120
caggtagatg acgaccatca gggacagctt caaggatcgc tcgcggctct taccagccta    9180
acttcgatca ctggaccgct gatcgtcacg gcgatttatg ccgcctcggc gagcacatgg    9240
aacgggttgg catggattgt aggcgccgcc ctataccttg tctgcctccc cgcgttgcgt    9300
cgcggtgcat ggagccgggc cacctcgacc tgaatggaag ccggcggcac ctcgctaacg    9360
gattcaccac tccaagaatt ggagccaatc aattcttgcg gagaactgtg aatgcgcaaa    9420
ccaacccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc cataccgcca    9840
gttgtttacc ctcacaacgt tccagtaacc gggcatgttc atcatcagta acccgtatcg    9900
tgagcatcct ctctcgtttc atcggtatca ttaccccat gaacagaaat tcccccttac    9960
acggaggcat caagtgacca aacaggaaaa aaccgcccct aacatggccc gctttatcag   10020
aagccagaca ttaacgcttc tggagaaact caacgagctg gacgcggatg aacaggcaga   10080
catctgtgaa tcgcttcacg accacgctga tgagctttac cgcagctgcc tcgcgcgttt   10140
cggtgatgac ggtgaaaacc tctgacacat gcagctcccg gagacggtca cagcttgtct   10200
gtaagcggat gccgggagca gacaagcccg tcagggcgcg tcagcgggtg ttggcgggtg   10260
tcggggcgca gccatgaccc agtcacgtag cgatagcgga gtgtatactg gcttaactat   10320
gcggcatcag agcagattgt actgagagtg caccatatgc ggtgtgaaat accgcacaga   10380
tgcgtaagga gaaaataccg catcaggcgc tcttccgctt cctcgctcac tgactcgctg   10440
cgctcggtcg ttcggctgcg gcgagcggta tcagctcact caaaggcggt aatacggtta   10500
```

```
tccacagaat cagggqataa cgcaggaaag aacatgtgag caaaaggcca gcaaaaggcc    10560
aggaaccgta aaaaggccgc gttgctggcg ttttttccata ggctccgccc ccctgacgag    10620
catcacaaaa atcgacgctc aagtcagagg tggcgaaacc cgacaggact ataaagatac    10680
caggcgtttc ccectggaag ctccctcgtg cgctctcctg ttccgaccct gccgcttacc    10740
ggatacctgt ccgcctttct cccttcggga agcgtggcgc tttctcatag ctcacgctgt    10800
aggtatctca gttcggtgta ggtcgttcgc tccaagctgg gctgtgtgca cgaaccccec    10860 gttcagcccg accgctgcgc cttatccggt aactatcgtc ttgagtccaa cccggtaaga    10920
cacgacttat cgccactggc agcagccact ggtaacagga ttagcagagc gaggtatgta    10980
ggcggtgcta cagagttctt gaagtggtgg cctaactacg gctacactag aaggacagta    11040
tttggtatct gcgctctgct gaagccagtt accttcggaa aaagagttgg tagctcttga    11100
tccggcaaac aaaccaccgc tggtagcggt ggtttttttg tttgcaagca gcagattacg    11160
cgcagaaaaa aaggatctca agaagatcct ttgatctttt ctacggggtc tgacgctcag    11220
tggaacgaaa actcacgtta agggattttg gtcatgagat tatcaaaaag gatcttcacc    11280
tagatccttt tctagataat acgactcact ata                                  11313
```

<210> SEQ ID NO 7
<211> LENGTH: 11313
<212> TYPE: DNA
<213> ORGANISM: Artificial Sequence
<220> FEATURE:
<223> OTHER INFORMATION: Plasmid

<400> SEQUENCE: 7

```
gccagccccc gattgggggc gacactccac catagatcac tccectgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg atcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc agggggcgcc cggttctttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg aagccggtc     840 ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
```

```
gtttccctct agcgggatca attccgcccc tctccctccc cccccctaa cgttactggc    1260 cgaagccgct tggaataagg ccggtgtgcg tttgtctata tgttatttc caccatattg    1320 ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttg caggcagcgg     1500 aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagcgcgg acctttactt ggtcacgagg catgccgatg tcattccggt gcgccggcgg    2160
ggcgacagca gggggagcct actctccccc aggcccgttt cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatggg aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggttcgggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc    2640 tctggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggga ggcacctcat tttctgccat tccaagaaga atgtgatga gctcgccgcg      2940 aagctgtccg gcctcggact caatgctgta gcatattacc ggggccttga tgtatccgtc    3000
ataccaacta gcggagacgt cattgtcgta gcaacgacg ctctaatgac gggctttacc     3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga     3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gccctgctg     3600
```

```
tataggctgg gagccgttca aaacgaggtt actaccacac accccataac caaatacatc   3660
atggcatgca tgtcagctga cctggaggtc gtcacgagca cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtctttta ccgggagttc   3840
gatgagatga agagtgcgc ctcacacctc ccttacatcg aacggggaat gcagctcgcc   3900
gaacatttca acagaaggc aatcgggttg ctgcaaacag ccaccaagca agcggaggct   3960
gctgctcccg cggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgccctcc accgaggacc tggttaacct actccctgct   4380
atcctctccc ctggcgccct agtcgtcggg gtcgtgtgcg cagcgatact gcgtcggcac   4440
gtgggcccag gggagggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagt agtacgtgga ggttacgcgg gtggggatt tccactacgt gacgggcatg   5040
accactgaca acgtaaagtg cccgtgtcag gttccggccc ccgaattctt cacagaagtg   5100 gatgggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgaccct cccacattac ggcggagacg   5280
gctaagcgta ggctggccag gggatctccc ccctccttgg ccagctcatc agctagccag   5340
ctgtctgcgc cttccttgaa ggcaacatgc actaccgtc atgactcccc ggacgctgac   5400
ctcatcgagg ccaacctcct gtggcggcag gagatgggcg ggaacatcac ccgcgtggag   5460
tcagaaaata aggtagtaat tttgactct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggag ggacccggac   5640
tacgtccctc cagtggtaca cgggtgtcca ttgccgcctg ccaaggcccc tccggtacca   5700
cctccacgga ggaagaggac ggttgtcctg ccagaatcta ccgtgtcttc cgccctggcg   5760
gagctcgcca caaagacctt cggcagctcc gaatcgtcgg ccgtcgacag cggcacggca   5820
acggcctctc ctgactagcc ctccaacgac ggcgacgcgg gatccgacgt tgagtcgtac   5880
tcccccatgc ccccccttga gggggagccg ggggatcccg attccagcga cgggtcttgg   5940
```

```
tctaccgtaa gcgaggtggt tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tggggcaaag   6300
gacgtccgga acctatccag caaggccgtt aaccacatcc gctccgtgtg aaggacttg    6360 ctggaagaca ctgagacacc aattgacacc accatcatgg caaaaaatga ggttttctgc   6420
gtccaaccag agaagggggg ccgcaagcca gctcgcctta tcgtattccc agatttgggg   6480
gttcgtgtgt gcgagaaaat ggccctttac gatgtggtct ccaccctccc tcaggccgtg   6540
atgggctctt catacggatt ccaatactct cctggacagc gggtcgagtt cctggtgaat   6600
gcctggaaag cgaagaaatg ccctatgggc ttcgcatatg acacccgctg ttttgactca   6660
acggtcactg agaatgacat ccgtgttgag gagtcaatct accaatgttg tgacttggcc   6720
cccgaagcca gacaggccat aaggtcgctc acagagcggc tttacatcgg ggcccctg    6780 actaattcta aagggcagaa ctgcggctat cgccggtgcc gcgcgagcgg tgtactgacg   6840
accagctgcg gtaataccct cacatgttac ttgaaggccg ctgcggcctg tcagctgcg    6900 aagctccagg actgcacgat gctcgtatgc ggagacgacc ttgtcgttat ctgtgaaagc   6960
gcggggaccc aagaggacga ggcgagccta cgggccttca cggaggctat gactagatac   7020
tctgcccccc ctggggaccc gcccaaacca gaatacgact tggagttgat aacatcatgc   7080
tcctccaatg tgtcagtcgc gcacgatgca tctggcaaaa gggtgtacta tctcacccgt   7140
gaccccacca ccccccttgc gcgggctgcg tgggagacag ctagacacac tccagtcaat   7200
tcctggctag gcaacatcat catgtatgcg cccaccttgt gggcaaggat gatcctgatg   7260
actcatttct tctccatcct tctagctcag gaacaacttg aaaaagccct agattgtcag   7320
atctacgggg cctgttactc cattgagcca cttgacctac ctcagatcat tcaacgactc   7380
catggcctta gcgcattttc actccatagt tactctccag gtgagatcaa tagggtggct   7440
tcatgcctca ggaaacttgg ggtaccgccc ttgcgagtct ggagacatcg gccagaagt    7500 gtccgcgcta ggctactgtc ccaggggggg agggctgcca cttgtggcaa gtacctcttc   7560
aactgggcag taaggaccaa gctcaaactc actccaatcc cggctgcgtc ccagttggat   7620
ttatccagct ggttcgttgc tggttacagc gggggagaca tatatcacag cctgtctcgt   7680
gcccgacccc gctggttcat gtggtgccta ctcctacttt ctgtaggggt aggcatctat   7740
ctactcccca accgatgaac ggggacctaa acactccagg ccaataggcc atcctgtttt   7800
tttccctttt ttttttttctt ttttttttttt tttttttttt ttctcctttt   7860 ttttttcctct ttttttcctt ttctttcctt tggtggctcc atcttagccc tagtcacggc   7920
tagctgtgaa aggtccgtga gccgcttgac tgcagagagt gctgatactg gcctctctgc   7980
agatcaagta ctcctgcagg cgcgccacta gtgggaatac gcggggtatg ccgcgtttta   8040
gcatattgac gacccaattc tcatgtttga cagcttatca tcgataagct ttaatgcggt   8100
agtttatcac agttaaattg ctaacgcagt caggcaccgt gtatgaaatc taacaatgcg   8160
ctcatcgtca tcctcggcac cgtcaccctg gatgctgtag catagggctt ggttatgccg   8220
gtactgccgg gcctcttgcg ggatatcgtc cattccgaca gcatcgccag tcactatggc   8280
gtgctgctag cgctatatgc gttgatgcaa tttctatgcg cacccgttct cggagcactg   8340
```

```
tccgaccgct tggccgccg cccagtcctg ctcgcttcgc tacttggagc cactatcgac    8400
tacgcgatca tggcgaccac acccgtcctg tggatcctct acgccggacg catcgtggcc    8460
ggcatcaccg gcgccacagg tgcggttgct ggcgcctata tcgccgacat caccgatggg    8520
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acggcctcaa cctactactg ggctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atcttgcacg ccctcgctca agccttcgtc    8940
actggtcccg ccaccaaacg tttcggcgag aagcaggcca ttatcgccgg catggcggcc    9000
gacgcgctgg gctacgtctt gctggcgttc gcgacgcgag gctggatggc cttccccatt    9060
atgattcttc tcgcttccgg cggcatcggg atgcccgcgt tgcaggccat gctgtccagg    9120
caggtagatg acgaccatca gggacagctt caaggatcgc tcgcggctct taccagccta    9180
acttcgatca ctggaccgct gatcgtcacg gcgatttatg ccgcctcggc gagcacatgg    9240
aacgggttgg catggattgt aggcgccgcc ctataccttg tctgcctccc cgcgttgcgt    9300
cgcggtgcat ggagccgggc cacctcgacc tgaatggaag ccggcggcac ctcgctaacg    9360
gattcaccac tccaagaatt ggagccaatc aattcttgcg gagaactgtg aatgcgcaaa    9420
ccaacccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc cataccgcca    9840
gttgtttacc ctcacaacgt tccagtaacc gggcatgttc atcatcagta acccgtatcg    9900
tgagcatcct ctctcgtttc atcggtatca ttacccccat gaacagaaat tcccccttac    9960
acggaggcat caagtgacca aacaggaaaa aaccgccctt aacatggccc gctttatcag   10020
aagccagaca ttaacgcttc tggagaaact caacgagctg gacgcggatg aacaggcaga   10080
catctgtgaa tcgcttcacg accacgctga tgagctttac cgcagctgcc tcgcgcgttt   10140
cggtgatgac ggtgaaaacc tctgacacat gcagctcccg gagacggtca cagcttgtct   10200
gtaagcggat gccgggagca gacaagcccg tcagggcgcg tcagcgggtg ttggcgggtg   10260
tcggggcgca gccatgaccc agtcacgtag cgatagcgga gtgtatactg gcttaactat   10320
gcggcatcag agcagattgt actgagagtg caccatatgc ggtgtgaaat accgcacaga   10380
tgcgtaagga gaaaataccg catcaggcgc tcttccgctt cctcgctcac tgactcgctg   10440
cgctcggtcg ttcggctgcg gcgagcggta tcagctcact caaaggcggt aatacggtta   10500
tccacagaat caggggataa cgcaggaaag aacatgtgag caaaaggcca gcaaaaggcc   10560
aggaaccgta aaaaggccgc gttgctggcg ttttttccata ggctccgccc ccctgacgag   10620
catcacaaaa atcgacgctc aagtcagagg tggcgaaacc cgacaggact ataaagatac   10680
```

```
caggcgtttc cccctggaag ctccctcgtg cgctctcctg ttccgaccct gccgcttacc   10740
ggatacctgt ccgcctttct cccttcggga agcgtggcgc tttctcatag ctcacgctgt   10800
aggtatctca gttcggtgta ggtcgttcgc tccaagctgg gctgtgtgca cgaaccccc    10860 gttcagcccg accgctgcgc cttatccggt aactatcgtc ttgagtccaa cccggtaaga   10920
cacgacttat cgccactggc agcagccact ggtaacagga ttagcagagc gaggtatgta   10980
ggcggtgcta cagagttctt gaagtggtgg cctaactacg gctacactag aaggacagta   11040
tttggtatct gcgctctgct gaagccagtt accttcggaa aaagagttgg tagctcttga   11100
tccggcaaac aaaccaccgc tggtagcggt ggttttttg tttgcaagca gcagattacg    11160
cgcagaaaaa aaggatctca agaagatcct ttgatctttt ctacggggtc tgacgctcag   11220
tggaacgaaa actcacgtta agggattttg gtcatgagat tatcaaaaag gatcttcacc   11280
tagatccttt tctagataat acgactcact ata                                11313
```

<210> SEQ ID NO 8
<211> LENGTH: 11313
<212> TYPE: DNA
<213> ORGANISM: Artificial Sequence
<220> FEATURE:
<223> OTHER INFORMATION: Plasmid

<400> SEQUENCE: 8

```
gccagccccc gattgggggc gacactccac catagatcac tccctgtga ggaactactg    60 tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tccttttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
ctcaaagaaa aaccaagggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc aggggcgccc ggttcttttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga   720
aagtatccat catggctgat gcaatgcggc ggctgcatac gcttgatccg gctacctgcc   780
cattcgacca ccaagcgaaa catcgcatcg agcgagcacg tactcggatg aagccggtc    840 ttgtcgatca ggatgatctg gacgaagagc atcaggggct cgcgccagcc gaactgttcg   900
ccaggctcaa ggcgcgcatg cccgacggcg aggatctcgt cgtgacccat ggcgatgcct   960
gcttgccgaa tatcatggtg aaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc   1260 cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
```

```
gttcctctgg aagcttcttg aagacaaaca acgtctgtag cgacccttty caggcagcgg   1500
aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctgggggcc tcggtgcaca tgctttacat gtgtttagtc gaggttaaaa   1740
aacgtctagg ccccccgaac cacggggacg tggttttcct ttgaaaaaca cgataatacc   1800
atggcgccta ttacgcccta ctcccaacag acgcgaggcc tacttggctg catcatcact   1860
agcctcacag gccgggacag gaaccaggtc gaggggggagg tccaagtggt ctccaccgca   1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgcccccc ggggcgcgtt ccttgacacc atgcacctgc   2100
ggcagctcgg acctttactt ggtcacgagg catgccgatg tcattccggt gcgccggcgg   2160
ggcgacagca gggggagcct actctccccc aggcccgtct cctacttgaa gggctcttcg   2220
ggcggtccac tgctctgccc ctcggggcac gctgtgggca tctttcgggc tgccgtgtgc   2280
acccgagggg ttgcgaaggc ggtggacttt gtaccgtcg agtctatggg aaccactatg   2340
cggtccccgg tcttcacgga caactcgtcc cctccggccg taccgcagac attccaggtg   2400
gcccatctac acgcccctac tggtagcggg aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacgggtg cccccatcac gtactccacc tatggcaagt tcttgccgga cggtggttgc   2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatccccttt tatggcaaag ccatccccat cgagaccatc   2880 aagggggggga ggcacctcat tttctgccat tccaagaaga aatgtgatga gctcgccgcg   2940
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg tagggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360
ccagggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gcccctgctg   3600
tataggctgg gagccgttca aaacgaggtt actaccacac accccataac caaatacatc   3660
atggcatgca tgtcggctga cctggaggtc gtcacgagca cctgggtgct ggtaggcgga   3720
gtcctagcag ctctggccgc gtattgcctg acaacaggca gcgtggtcat tgtgggcagg   3780
```

```
atcatcttgt ccggaaagcc ggccatcatt cccgacaggg aagtcctttta ccgggagttc    3840 gatgagatgg aagagtgcgc ctcacacctc ccttacatcg aacagggaat gcagctcgcc    3900
gaacaattca aacagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgaccct cccacattac ggcggagacg    5280
gctaagcgta ggctgccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatggggc ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgccgga ttacaaccct ccactgttag agtcctggaa ggaccccgac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
```

```
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggcccttttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggcccctg    6780 actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctggggaccc gcccaaacca gaatacgact tggagttgat aacatcatgc    7080
tcctccaatg tgtcagtcgc gcacgatgca tctggcaaaa gggtgtacta tctcacccgt    7140
gaccccacca cccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcatttttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
gcccgacccc gctggttcat gtggtgccta ctcctacttt ctgtaggggt aggcatctat    7740
ctactcccca accgatgaac ggggacctaa acactccagg ccaataggcc atcctgtttt    7800
tttccctttt ttttttttctt tttttttttt tttttttttt ttttttttttt ttctcctttt    7860 ttttcctct ttttttcctt ttctttcctt tggtggctcc atcttagccc tagtcacggc    7920
tagctgtgaa aggtccgtga gccgcttgac tgcagagagt gctgatactg gcctctctgc    7980
agatcaagta ctcctgcagg cgcgccacta gtgggaatac gcggggtatg ccgcgtttta    8040
gcatattgac gacccaattc tcatgtttga cagcttatca tcgataagct ttaatgcggt    8100
agtttatcac agttaaattg ctaacgcagt caggcaccgt gtatgaaatc taacaatgcg    8160
ctcatcgtca tcctcggcac cgtcaccctg atgctgtag gcataggctt ggttatgccg    8220
gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac accgtcctg tggatcctct acgccggacg catcgtggcc    8460
ggcatcaccg gcgccacagg tgcggttgct ggcgcctata tcgccgacat caccgatggg    8520
```

```
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acggcctcaa cctactactg ggctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atcttgcacg ccctcgctca agccttcgtc    8940
actggtcccg ccaccaaacg tttcggcgag aagcaggcca ttatcgccgg catggcggcc    9000
gacgcgctgg gctacgtctt gctggcgttc gcgacgcgag gctggatggc cttccccatt    9060
atgattcttc tcgcttccgg cggcatcggg atgcccgcgt gcaggccat gctgtccagg     9120
caggtagatg acgaccatca gggacagctt caaggatcgc tcgcggctct taccagccta    9180
acttcgatca ctggaccgct gatcgtcacg gcgatttatg ccgcctcggc gagcacatgg    9240
aacgggttgg catggattgt aggcgccgcc ctataccttg tctgcctccc cgcgttgcgt    9300
cgcggtgcat ggagccgggc cacctcgacc tgaatgaaag ccggcggcac ctcgctaacg    9360
gattcaccac tccaagaatt ggagccaatc aattcttgcg gagaactgtg aatgcgcaaa    9420
ccaacccttg gcagaacata tccatcgcgt ccgccatctc cagcagccgc acgcggcgca    9480
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc cataccgcca    9840
gttgtttacc ctcacaacgt tccagtaacc gggcatgttc atcatcagta acccgtatcg    9900
tgagcatcct ctctcgtttc atcggtatca ttaccccccat gaacagaaat tcccccttac    9960
acggaggcat caagtgacca aacaggaaaa aaccgcccct aacatggccc gctttatcag   10020
aagccagaca ttaacgcttc tggagaaact caacgagctg gacgcggatg aacaggcaga   10080
catctgtgaa tcgcttcacg accacgctga tgagctttac cgcagctgcc tcgcgcgttt   10140
cggtgatgac ggtgaaaacc tctgacacat gcagctcccg gagacggtca gcttgtct    10200
gtaagcggat gccgggagca gacaagcccg tcagggcgcg tcagcgggtg ttggcggtg    10260
tcggggcgca gccatgaccc agtcacgtag cgatagcgga gtgtatactg gcttaactat   10320
gcggcatcag agcagattgt actgagagtg caccatatgc ggtgtgaaat accgcacaga   10380
tgcgtaagga gaaaataccg catcaggcgc tcttccgctt cctcgctcac tgactcgctg   10440
cgctcggtcg ttcggctgcg gcgagcggta tcagctcact caaaggcggt aatacggtta   10500
tccacagaat caggggataa cgcaggaaag aacatgtgag caaaaggcca gcaaaaggcc   10560
aggaaccgta aaaaggccgc gttgctggcg ttttccata ggctccgccc cctgacgag     10620
catcacaaaa atcgacgctc aagtcagagg tggcgaaacc cgacaggact ataaagatac   10680
caggcgtttc ccctggaag ctccctcgtg cgctctcctg ttccgaccct gccgcttacc    10740
ggatacctgt ccgcctttct cccttcggga agcgtggcgc tttctcatag ctcacgctgt   10800
aggtatctca gttcggtgta ggtcgttcgc tccaagctgg gctgtgtgca cgaaccccc    10860
gttcagcccg accgctgcgc cttatccggt aactatcgtc ttgagtccaa cccggtaaga   10920
```

-continued

```
cacgacttat cgccactggc agcagccact ggtaacagga ttagcagagc gaggtatgta   10980
ggcggtgcta cagagttctt gaagtggtgg cctaactacg gctacactag aaggacagta   11040
tttggtatct gcgctctgct gaagccagtt accttcggaa aaagagttgg tagctcttga   11100
tccggcaaac aaaccaccgc tggtagcggt ggttttttg  tttgcaagca gcagattacg   11160
cgcagaaaaa aaggatctca agaagatcct ttgatctttt ctacgggtc  tgacgctcag   11220 tggaacgaaa actcacgtta agggattttg gtcatgagat tatcaaaaag gatcttcacc   11280
tagatccttt tctagataat acgactcact ata                                11313
```

<210> SEQ ID NO 9
<211> LENGTH: 11313
<212> TYPE: DNA
<213> ORGANISM: Artificial Sequence
<220> FEATURE:
<223> OTHER INFORMATION: Plasmid

<400> SEQUENCE: 9

```
gccagccccc gattgggggc gacactccac catagatcac tcccctgtga ggaactactg     60
tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactggga caacagaca  atcggctgct    480 ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg aagccggtc    840 ttgtcgatca ggatgatctg gacgaagagc atcaggggct cgcgccagcc gaactgttcg    900
ccaggctcaa ggcgcgcatg cccgacgcg  aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc ccccccctaa cgttactggc   1260
cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
gttcctctgg aagcttcttg aagacaaaca acgtctgtag cgacccttg  caggcagcgg   1500 aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
```

-continued

```
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacgggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcgctggca agcgcccccc ggggcgcgtt ccttgacacc atgcacctgc    2100
ggcagctcgg accttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatggg aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg ccccccatcac gtactccacc tatggcaagt tcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880
aagggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcgagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggcagg atgggcattt acaggtttgt gactccagga    3240
gaacggcccct cggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca cgtggtcat tgtgggcagg    3780
atcatcttgt ccggaaagcc ggccatcatt cccgacaggg aagtccttta ccggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
```

```
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgccctcc accgaggacc tggttaacct actccctgct   4380
atcctctccc ctggcgccct agtcgtcggg gtcgtgtgcg cagcgatact gcgtcggcac   4440
gtgggcccag ggagggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
caaaccacct gcccatgtgg agcacagatc accggacatg tgaaaacgg ttccatgagg   4860 atcgtggggc ctaggacctg tagtaacacg tggcatggaa cattccccat taacgcgtac   4920
accacgggcc cctgcacgcc ctcccggcg ccaaattatt ctaggcgct gtggcgggtg   4980 gctgctgagg agtacgtgga ggttacgcgg gtgggggatt tccactacgt gacgggcatg   5040
accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgaccct ccacattac ggcggagacg   5280 gctaagcgta ggctggccag gggatctccc ccctccttgg ccagctcatc agctatccag   5340
ctgtctgcgc cttccttgaa ggcaacatgc actacccgtc atgactcccc ggacgctgac   5400
ctcatcgagg ccaacctcct gtggcggcag gagatgggcg gaacatcac ccgcgtggag   5460 tcagaaaata aggtagtaat tttggagtct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggaa ggacccggac   5640
tacgtccctc cagtggtaca cggggtgtcca ttgccgcctg ccaaggcccc tcgataccca   5700
cctccacgga ggaagaggac ggttgtcctg tcagaatcta ccgtgtcttc tgccttggcg   5760
gagctcgcca caaagaccctt cggcagctcc gaatcgtcgg ccgtcgacag cggcacggca   5820
acggcctctc ctgaccagcc ctccgacgac ggcgacgcgg atccgacgt tgagtcgtac   5880 tcctccatgc ccccccttga gggggagccg ggggatcccg atctcagcga cgggtcttgg   5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta gctgacgcc cccacattcg gccagatcta aatttggcta tggggcaaag   6300
gacgtccgga acctatccag caaggccgtt aaccacatcg gctccgtgtg gaaggacttg   6360
```

```
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggcccttttac gatgtggtct ccaccctccc tcaggccgtg   6540
atgggctctt catacggatt ccaatactct cctggacagc gggtcgagtt cctggtgaat    6600
gcctggaaag cgaagaaatg ccctatgggc ttcgcatatg acaccgctg ttttgactca     6660
acggtcactg agaatgacat ccgtgttgag gagtcaatct accaatgttg tgacttggcc    6720
cccgaagcca gacaggccat aaggtcgctc acagagcggc tttacatcgg gggcccctg     6780
actaattcta aagggcagaa ctgcggctat cgccggtgcc gcgcgagcgg tgtactgacg    6840
accagctgcg gtaatacccct cacatgttac ttgaaggccg ctgcggcctg tcgagctgcg   6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctgggacccc gcccaaacca gaatacgact ggagttgat aacatcatgc     7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagcccct agattgtcag   7320
atctacgggg cctgttactc cattgagcca cttgacctac ctcagatcat tcaacgactc    7380
catgccctta gcgcatttttc actccatagt tactctccag gtgagatcaa tagggtggct   7440
tcatgcctca ggaaacttgg ggtaccgccc ttgcgagtct ggagacatcg ggccagaagt    7500
gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt     7680
gcccgacccc gctggttcat gtggtgccta ctcctacttt ctgtagggt aggcatctat     7740
ctactcccca accgatgaac ggggacctaa acactccagg ccaataggcc atcctgtttt    7800
tttccctttt tttttttctt tttttttttt tttttttttt tttttttttt ttctccttttt   7860
ttttttctct ttttttcctt ttcttttcctt tggtggctcc atcttagccc tagtcacggc   7920
tagctgtgaa aggtccgtga gccgcttgac tgcagagagt gctgatactg gcctctctgc    7980
agatcaagta ctcctgcagg cgcgccacta gtgggaatac gcggggtatg ccgcgttta    8040
gcatattgac gacccaattc tcatgtttga cagcttatca tcgataagct ttaatgcggt    8100
agtttatcac agttaaattg ctaacgcagt caggcaccgt gtatgaaatc taacaatgcg    8160
ctcatcgtca tcctcggcac cgtcaccctg gatgctgtag gcataggctt ggttatgccg    8220
gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac acccgtcctg tggatcctct acgccggacg catcgtggcc    8460
ggcatcaccg cgccacagg tgcggttgct ggcgcctata tcgccgacat caccgatggg     8520
gaagatcggc tcgccacttt cgggctcatg agcgcttgtt tcggcgtggg tatggtggca    8580
ggccccgtgg ccgggggact gttgggcgcc atctccttgc atgcaccatt ccttgcggcg    8640
gcggtgctca acgcctcaa cctactctg ggctgcttcc taatgcagga gtcgcataag      8700
ggagagcgtc gaccgatgcc cttgagagcc ttcaacccag tcagctcctt ccggtgggcg    8760
```

```
cggggcatga ctatcgtcgc cgcacttatg actgtcttct ttatcatgca actcgtagga   8820
caggtgccgg cagcgctctg ggtcattttc ggcgaggacc gctttcgctg gagcgcgacg   8880
atgatcggcc tgtcgcttgc ggtattcgga atcttgcacg ccctcgctca agccttcgtc   8940
actggtcccg ccaccaaacg tttcggcgag aagcaggcca ttatcgccgg catggcggcc   9000
gacgcgctgg gctacgtctt gctggcgttc gcgacgcgag gctggatggc cttccccatt   9060
atgattcttc tcgcttccgg cggcatcggg atgcccgcgt tgcaggccat gctgtccagg   9120
caggtagatg acgaccatca gggacagctt caaggatcgc tcgcggctct taccagccta   9180
acttcgatca ctggaccgct gatcgtcacg gcgatttatg ccgcctcggc gagcacatgg   9240
aacgggttgg catggattgt aggcgccgcc ctataccttg tctgcctccc cgcgttgcgt   9300
cgcggtgcat ggagccgggc cacctcgacc tgaatggaag ccggcggcac ctcgctaacg   9360
gattcaccac tccaagaatt ggagccaatc aattcttgcg gagaactgtg aatgcgcaaa   9420
ccaacccttg gcagaacata tccatcgcgt ccgccatctc cagcagccgc acgcggcgca   9480
tctcgggcag cgttgggtcc tggccacggg tgcgcatgat cgtgctcctg tcgttgagga   9540
cccggctagg ctggcggggt tgccttactg gttagcagaa tgaatcaccg atacgcgagc   9600
gaacgtgaag cgactgctgc tgcaaaacgt ctgcgacctg agcaacaaca tgaatggtct   9660
tcggtttccg tgtttcgtaa agtctggaaa cgcggaagtc agcgccctgc accattatgt   9720
tccggatctg catcgcagga tgctgctggc taccctgtgg aacacctaca tctgtattaa   9780
cgaagcgctg gcattgaccc tgagtgattt ttctctggtc ccgccgcatc cataccgcca   9840
gttgtttacc ctcacaacgt tccagtaacc gggcatgttc atcatcagta acccgtatcg   9900
tgagcatcct ctctcgtttc atcggtatca ttaccccat gaacagaaat tccccttac    9960
acggaggcat caagtgacca aacaggaaaa aaccgccctt aacatggccc gctttatcag  10020
aagccagaca ttaacgcttc tggagaaact caacgagctg gacgcggatg aacaggcaga  10080
catctgtgaa tcgcttcacg accacgctga tgagctttac cgcagctgcc tcgcgcgttt  10140
cggtgatgac ggtgaaaacc tctgacacat gcagctcccg gagacggtca cagcttgtct  10200
gtaagcggat gccgggagca gacaagcccg tcagggcgcg tcagcgggtg ttggcgggtg  10260
tcggggcgca gccatgaccc agtcacgtag cgatagcgga gtgtatactg gcttaactat  10320
gcggcatcag agcagattgt actgagagtg caccatatgc ggtgtgaaat accgcacaga  10380
tgcgtaagga gaaaataccg catcaggcgc tcttccgctt cctcgctcac tgactcgctg  10440
cgctcggtcg ttcggctgcg gcgagcggta tcagctcact caaaggcggt aatacggtta  10500
tccacagaat caggggataa cgcaggaaag aacatgtgag caaaaggcca gcaaaaggcc  10560
aggaaccgta aaaaggccgc gttgctggcg tttttccata ggctccgccc ccctgacgag  10620
catcacaaaa atcgacgctc aagtcagagg tggcgaaacc cgacaggact ataaagatac  10680
caggcgtttc cccctggaag ctccctcgtg cgctctcctg ttccgaccct gccgcttacc  10740
ggatacctgt ccgcctttct cccttcggga agcgtggcgc tttctcatag ctcacgctgt  10800
aggtatctca gttcggtgta ggtcgttcgc tccaagctgg gctgtgtgca cgaaccccc   10860
gttcagcccg accgctgcgc cttatccggt aactatcgtc ttgagtccaa cccgtaaga  10920
cacgacttat cgccactggc agcagccact ggtaacagga ttagcagagc gaggtatgta  10980
ggcggtgcta cagagttctt gaagtggtgg cctaactacg gctacactag aaggacagta  11040
tttggtatct gcgctctgct gaagccagtt accttcggaa aaagagttgg tagctcttga  11100
```

-continued

```
tccggcaaac aaaccaccgc tggtagcggt ggttttttg tttgcaagca gcagattacg    11160
cgcagaaaaa aaggatctca agaagatcct ttgatctttt ctacgggtc tgacgctcag    11220
tggaacgaaa actcacgtta agggattttg gtcatgagat tatcaaaaag gatcttcacc   11280
tagatccttt tctagataat acgactcact ata                                11313
```

<210> SEQ ID NO 10
<211> LENGTH: 11313
<212> TYPE: DNA
<213> ORGANISM: Artificial Sequence
<220> FEATURE:
<223> OTHER INFORMATION: Plasmid

<400> SEQUENCE: 10

```
gccagccccc gattgggggc gacactccac catagatcac tcccctgtga ggaactactg     60
tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc ccccctaa cgttactggc    1260
cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtctttt cccctctcgc caaaggaatg caaggtctgt tgaatgtcgt gaaggaagca   1440
gttcctctgg aagcttcttg aagacaaaca acgtctgtag cgaccctttg caggcagcgg   1500
aacccccac ctggcgacag tgcctctgc ggccaaaagc cacgtgtata agatacacct    1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctggggcc tcggtgcaca tgctttacat gtgtttagtc gaggttaaaa   1740
aacgtctagg ccccccgaac cacggggacg tggttttcct ttgaaaaaca cgataatacc   1800
atggcgccta ttacggccta ctcccaacag acgcgaggcc tacttggctg catcatcact   1860
```

```
agcctcacag gccgggacag gaaccaggtc gagggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgcggcgg     2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatggg aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tccttgccga cggtggttgc    2640
tctgggggcg cctatgacat cataatatgt gatgagtgcc actcaactga ctcgaccact    2700
atcctgggca tcggcacagt cctgaccaa gcggagacgg ctggagcgcg actcgtcgtg     2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacgacg ctctaatgac gggctttacc      3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcagctga cctggaggtc gtcacgagca cctgggtgct ggtaggcgga    3720
gtcctagcag ctctggccgc gtattgcctg acaacaggca cgtggtcat tgtgggcagg     3780
atcatcttgt ccggaaagcc ggccatcatt cccgacaggg aagtctttta ccgggagttc    3840
gatgagatgg aagagtgcgc ctcacacctc ccttacatcg aacggggaat gcagctcgcc    3900
gaacatttca acagaaggc aatcgggttg ctgcaaacag ccaccaagca agcggaggct    3960
gctgctcccg cggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggggatgg gtggccgccc aacttgctcc tcccagcgct    4200
```

```
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860 atcgtgggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagt agtacgtgga ggttacgcgg gtgggggatt ccactacgt gacgggcatg    5040 accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460 tcagaaaata agtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccggac    6180 gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg    6360 ctggaagaca ctgagacacc aattgacacc accatcatgg caaaaaatga gttttctgc    6420 gtccaaccag agaagggggg ccgcaagcca gctcgcctta tcgtattccc agatttgggg    6480
gttcgtgtgt gcgagaaaat ggcccttac gatgtggtct ccaccctccc tcaggccgtg    6540
atgggctctt catacggatt ccaatactct cctggacagc gggtcgagtt cctggtgaat    6600
```

```
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccctg     6780 actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctggggaccc gcccaaacca gaatacgact tggagttgat aacatcatgc    7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag caacatcat catgtatgcg cccaccttgt gggcaaggat gatcctgatg     7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg gccagaagt     7500 gtccgcgcta ggctactgtc ccagggggggg agggctgcca cttgtggcaa gtacctcttc   7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
gcccgacccc gctggttcat gtggtgccta ctcctacttt ctgtaggggt aggcatctat    7740
ctactcccca accgatgaac ggggacctaa acactccagg ccaataggcc atcctgtttt    7800
tttccctttt tttttttctt tttttttttt tttttttttt tttttttttt ttctcctttt    7860
tttttcctct tttttttcctt ttctttcctt tggtggctcc atcttagccc tagtcacggc   7920
tagctgtgaa aggtccgtga ccgcttgac tgcagagagt gctgatactg gcctctctgc     7980
agatcaagta ctcctgcagg cgcgccacta gtgggaatac gcggggtatg ccgcgtttta    8040
gcatattgac gacccaattc tcatgtttga cagcttatca tcgataagct ttaatgcggt    8100
agtttatcac agttaaattg ctaacgcagt caggcaccgt gtatgaaatc taacaatgcg    8160
ctcatcgtca tcctcggcac cgtcaccctg gatgctgtag cataggctt ggttatgccg     8220 gtactgccgg gcctcttgcg ggatatcgtc cattccgaca gcatcgccag tcactatggc    8280
gtgctgctag cgctatatgc gttgatgcaa tttctatgcg cacccgttct cggagcactg    8340
tccgaccgct ttggccgccg cccagtcctg ctcgcttcgc tacttggagc cactatcgac    8400
tacgcgatca tggcgaccac accgtcctg tggatcctct acgccggacg catcgtggcc     8460
ggcatcaccg gcgccacagg tgcggttgct ggcgcctata tcgccgacat caccgatggg    8520
gaagatcggg ctcgccactt cgggctcatg agcgcttgtt tcggcgtggg tatggtggca    8580
ggccccgtgg ccgggggact gttgggcgcc atctccttgc atgcaccatt ccttgcggcg    8640
gcggtgctca acggcctcaa cctactactg ggctgcttcc taatgcagga gtcgcataag    8700
ggagagcgtc gaccgatgcc cttgagagcc ttcaacccag tcagctcctt ccggtgggcg    8760
cggggcatga ctatcgtcgc cgcacttatg actgtcttct ttatcatgca actcgtagga    8820
caggtgccgg cagcgctctg ggtcattttc ggcgaggacc gctttcgctg gagcgcgacg    8880
atgatcggcc tgtcgcttgc ggtattcgga atcttgcacg ccctcgctca agccttcgtc    8940
```

```
actggtcccg ccaccaaacg tttcggcgag aagcaggcca ttatcgccgg catggcggcc   9000
gacgcgctgg gctacgtctt gctggcgttc gcgacgcgag gctggatggc cttccccatt   9060
atgattcttc tcgcttccgg cggcatcggg atgcccgcgt tgcaggccat gctgtccagg   9120
caggtagatg acgaccatca gggacagctt caaggatcgc tcgcggctct taccagccta   9180
acttcgatca ctggaccgct gatcgtcacg gcgatttatg ccgcctcggc gagcacatgg   9240
aacgggttgg catggattgt aggcgccgcc ctataccttg tctgcctccc cgcgttgcgt   9300
cgcggtgcat ggagccgggc cacctcgacc tgaatggaag ccggcggcac ctcgctaacg   9360
gattcaccac tccaagaatt ggagccaatc aattcttgcg gagaactgtg aatgcgcaaa   9420
ccaacccttg gcagaacata tccatcgcgt ccgccatctc cagcagccgc acgcggcgca   9480
tctcgggcag cgttgggtcc tggccacggg tgcgcatgat cgtgctcctg tcgttgagga   9540
cccggctagg ctggcggggt tgccttactg gttagcagaa tgaatcaccg atacgcgagc   9600
gaacgtgaag cgactgctgc tgcaaaacgt ctgcgacctg agcaacaaca tgaatggtct   9660
tcggtttccg tgtttcgtaa agtctggaaa cgcggaagtc agcgccctgc accattatgt   9720
tccgatctg catcgcagga tgctgctggc taccctgtgg aacacctaca tctgtattaa   9780
cgaagcgctg gcattgaccc tgagtgattt ttctctggtc ccgccgcatc cataccgcca   9840
gttgtttacc ctcacaacgt tccagtaacc gggcatgttc atcatcagta acccgtatcg   9900
tgagcatcct ctctcgtttc atcggtatca ttaccccat gaacagaaat tccccttac   9960
acggaggcat caagtgacca aacaggaaaa aaccgccctt aacatggccc gctttatcag  10020
aagccagaca ttaacgcttc tggagaaact caacgagctg gacgcggatg aacaggcaga  10080
catctgtgaa tcgcttcacg accacgctga tgagctttac cgcagctgcc tcgcgcgttt  10140
cggtgatgac ggtgaaaacc tctgacacat gcagctcccg gagacggtca gcttgtct  10200
gtaagcggat gccgggagca gacaagcccg tcagggcgcg tcagcgggtg ttggcgggtg  10260
tcggggcgca gccatgaccc agtcacgtag cgatagcgga gtgtatactg gcttaactat  10320
gcggcatcag agcagattgt actgagagtg caccatatgc ggtgtgaaat accgcacaga  10380
tgcgtaagga gaaaataccg catcaggcgc tcttccgctt cctcgctcac tgactcgctg  10440
cgctcggtcg ttcggctgcg gcgagcggta tcagctcact caaaggcggt aatacggtta  10500
tccacagaat caggggataa cgcaggaaag aacatgtgag caaaaggcca gcaaaggcc  10560
aggaaccgta aaaaggccgc gttgctggcg ttttttccata ggctccgccc cctgacgag  10620
catcacaaaa atcgacgctc aagtcagagg tggcgaaacc cgacaggact ataaagatac  10680
caggcgtttc ccctggaag ctccctcgtg cgctctcctg ttccgaccct gccgcttacc  10740
ggatacctgt ccgcctttct cccttcggga agcgtggcgc tttctcatag ctcacgctgt  10800
aggtatctca gttcggtgta ggtcgttcgc tccaagctgg gctgtgtgca cgaacccccc  10860
gttcagcccg accgctgcgc cttatccggt aactatcgtc ttgagtccaa cccggtaaga  10920
cacgacttat cgccactggc agcagccact ggtaacagga ttagcagagc gaggtatgta  10980
ggcggtgcta cagagttctt gaagtggtgg cctaactacg gctacactag aaggacagta  11040
tttggtatct gcgctctgct gaagccagtt accttcggaa aaagagttgg tagctcttga  11100
tccggcaaac aaaccaccgc tggtagcggt ggtttttttg tttgcaagca gcagattacg  11160
cgcagaaaaa aaggatctca agaagatcct ttgatctttt ctacggggtc tgacgctcag  11220
tggaacgaaa actcacgtta agggattttg gtcatgagat tatcaaaaag gatcttcacc  11280
tagatccttt tctagataat acgactcact ata                                11313
```

-continued

<210> SEQ ID NO 11
<211> LENGTH: 11184
<212> TYPE: DNA
<213> ORGANISM: Artificial Sequence
<220> FEATURE:
<223> OTHER INFORMATION: Plasmid

<400> SEQUENCE: 11

```
gccagccccc gattgggggc gacactccac catagatcac tcccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg aagccggtc      840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc cccccctaa cgttactggc     1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttg caggcagcgg     1500
aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctgggcc tcggtgcaca tgctttacat gtgtttagtc gaggttaaaa     1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca     1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
```

```
caggacctcg tcggctggca agcgccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc    2640 tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga gtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtcctttta ccgggagttc    3840 gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcccctcc accgaggacc tggttaacct actccctgct    4380
atcctctccc ctggcgccct agtcgtcggg gtcgtgtgcg cagcgatact cgtcgcac    4440
```

```
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtcccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtgggc ctaggacctg tagtaacacg tggcatggaa cattccccat taacgcgtac    4920
accacgggcc cctgcacgcc ctccccggcg ccaaattatt ctaggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatgggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgaccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cactcccgga ttacaaccct ccactgttag agtcctggaa ggaccccggac    5640
tacgtccctc cagtggtaca cgggtgtcca ttgccgcctg ccaaggcccc tccggtacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctggtgagga cgtcgtctgc tgctcgatgt cctacacatg gacaggcgcc    5880
ctgatcacgc catgcgctgc ggaggaaacc aagctgccca tcaatgcact gagcaactct    5940
ttgctccgac accacaactt ggtctatgct acaacatctc gcagcgcaag cctgcggcag    6000
aagaaggtca cctttgacag actgcaggtc ctggacgacc actaccggga cgtgctcaag    6060
gagatgaagg cgaaggcgtc cacagttaag gctaaacttc tatccgtgga ggaagcctgt    6120
aagctgacgc ccccacattc ggccagatct aaatttggct atgggcaaa ggacgtccgg    6180
aacctatcca gcaaggccgt taaccacatc cgctccgtgt ggaaggactt gctggaagac    6240
actgagacac caattgacac caccatcatg gcaaaaaatg aggttttctg cgtccaacca    6300
gagaaggggg gccgcaagcc agctcgcctt atcgtattcc cagatttggg ggttcgtgtg    6360
tgcgagaaaa tggcccttta cgatgtggtc tccaccctcc ctcaggccgt gatgggctct    6420
tcatacggat ccaatactc tcctggacag cgggtcgagt tcctggtgaa tgcctggaaa    6480
gcgaagaaat gccctatggg cttcgcatat gacacccgct gttttgactc aacggtcact    6540
gagaatgaca tccgtgttga ggagtcaatc taccaatgtt gtgacttggc ccccgaagcc    6600
agacaggcca taggtcgct cacagagcgg ctttacatcg ggggcccct gactaattct    6660
aaagggcaga actgcggcta tcgcggtgc cgcgcgagcg tgtactgac gaccagctgc    6720
ggtaataccc tcacatgtta cttgaaggcc gctgcggcct gtcgagctgc gaagctccag    6780
```

```
gactgcacga tgctcgtatg cggagacgac cttgtcgtta tctgtgaaag cgcggggacc   6840
caagaggacg aggcgagcct acgggccttc acggaggcta tgactagata ctctgccccc   6900
cctggggacc cgcccaaacc agaatacgac ttggagttga taacatcatg ctcctccaat   6960
gtgtcagtcg cgcacgatgc atctggcaaa agggtgtact atctcacccg tgaccccacc   7020
accccccttg cgcgggctgc gtgggagaca gctagacaca ctccagtcaa ttcctggcta   7080
ggcaacatca tcatgtatgc gcccaccttg tgggcaagga tgatcctgat gactcatttc   7140
ttctccatcc ttctagctca ggaacaactt gaaaaagccc tagattgtca gatctacggg   7200
gcctgttact ccattgagcc acttgaccta cctcagatca ttcaacgact ccatggcctt   7260
agcgcatttt cactccatag ttactctcca ggtgagatca ataggggtggc ttcatgcctc   7320
aggaaacttg gggtaccgcc cttgcgagtc tggagacatc gggccagaag tgtccgcgct   7380
aggctactgt cccaggggggg gagggctgcc acttgtggca agtacctctt caactgggca   7440
gtaaggacca agctcaaact cactccaatc ccggctgcgt cccagttgga tttatccagc   7500
tggttcgttg ctggttacag cgggggagac atatatcaca gcctgtctcg tgcccgaccc   7560
cgctggttca tgtggtgcct actcctactt tctgtagggg taggcatcta tctactcccc   7620
aaccgatgaa cggggaccta aacactccag gccaataggc catcctgttt ttttccctttt  7680
tttttttcct tttttttttt tttttttttt tttttttttt ttctcctttt tttttttcctc   7740
tttttttcct tttctttcct ttggtggctc catcttagcc ctagtcacgg ctagctgtga   7800
aaggtccgtg agccgcttga ctgcagagag tgctgatact ggcctctctg cagatcaagt   7860
actcctgcag gcgcgccact agtgggaata cgcggggtat gccgcgtttt agcatattga   7920
cgacccaatt ctcatgtttg acagcttatc atcgataagc tttaatgcgg tagtttatca   7980
cagttaaatt gctaacgcag tcaggcaccg tgtatgaaat ctaacaatgc gctcatcgtc   8040
atcctcggca ccgtcaccct ggatgctgta ggcataggct tggttatgcc ggtactgccg   8100
ggcctcttgc gggatatcgt ccattccgac agcatcgcca gtcactatgg cgtgctgcta   8160
gcgctatatg cgttgatgca atttctatgc gcacccgttc tcggagcact gtccgaccgc   8220
tttggccgcc gcccagtcct gctcgcttcg ctacttggag ccactatcga ctacgcgatc   8280
atggcgacca cacccgtcct gtggatcctc tacgccggac gcatcgtggc cggcatcacc   8340
ggcgccacag gtgcggttgc tggcgcctat atcgccgaca tcaccgatgg ggaagatcgg   8400
gctcgccact tcgggctcat gagcgcttgt ttcggcgtgg gtatggtggc aggccccgtg   8460
gccggggggac tgttgggcgc catctccttg catgcaccat tccttgcggc ggcggtgctc   8520
aacggcctca acctactact gggctgcttc ctaatgcagg agtcgcataa gggagagcgt   8580
cgaccgatgc ccttgagagc cttcaaccca gtcagctcct tccggtgggc gcggggcatg   8640
actatcgtcg ccgcacttat gactgtcttc tttatcatgc aactcgtagg acaggtgccg   8700
gcagcgctct gggtcatttt cggcgaggac cgctttcgct ggagcgcgac gatgatcggc   8760
ctgtcgcttg cggtattcgg aatcttgcac gccctcgctc aagccttcgt cactggtccc   8820
gccaccaaac gtttcggcga agcaggcc attatcgccg gcatggcggc cgacgcgctg   8880
ggctacgtct tgctggcgtt cgcgacgcga ggctggatgg ccttccccat tatgattctt   8940
ctcgcttccg gcggcatcgg gatgcccgcg ttgcaggcca tgctgtccag gcaggtagat   9000
gacgaccatc agggacagct tcaaggatcg ctcgcggctc ttaccagcct aacttcgatc   9060
actgaccgc tgatcgtcac ggcgatttat gccgcctcgg cgagcacatg gaacgggttg   9120
gcatggattg taggcgccgc cctataccttt gtctgcctcc ccgcgttgcg tcgcggtgca   9180
```

```
tggagccggg ccacctcgac ctgaatggaa gccggcggca cctcgctaac ggattcacca    9240
ctccaagaat tggagccaat caattcttgc ggagaactgt gaatgcgcaa accaacccct    9300
ggcagaacat atccatcgcg tccgccatct ccagcagccg cacgcggcgc atctcgggca    9360
gcgttgggtc ctggccacgg gtgcgcatga tcgtgctcct gtcgttgagg acccggctag    9420
gctggcgggg ttgccttact ggttagcaga atgaatcacc gatacgcgag cgaacgtgaa    9480
gcgactgctg ctgcaaaacg tctgcgacct gagcaacaac atgaatggtc ttcggtttcc    9540
gtgtttcgta aagtctggaa acgcggaagt cagcgccctg caccattatg ttccggatct    9600
gcatcgcagg atgctgctgg ctaccctgtg aacacctac atctgtatta acgaagcgct    9660
ggcattgacc ctgagtgatt tttctctggt cccgccgcat ccataccgcc agttgtttac    9720
cctcacaacg ttccagtaac cgggcatgtt catcatcagt aacccgtatc gtgagcatcc    9780
tctctcgttt catcggtatc attacccca tgaacagaaa ttccccctta cacggaggca    9840
tcaagtgacc aaacaggaaa aaaccgccct taacatggcc cgctttatca gaagccagac    9900
attaacgctt ctgagaaaac tcaacgagct ggacgcggat gaacaggcag acatctgtga    9960
atcgcttcac gaccacgctg atgagcttta ccgcagctgc ctcgcgcgtt tcggtgatga   10020
cggtgaaaac ctctgacaca tgcagctccc ggagacggtc acagcttgtc tgtaagcgga   10080
tgccgggagc agacaagccc gtcagggcgc gtcagcgggt gttggcgggt gtcggggcgc   10140
agccatgacc cagtcacgta gcgatagcgg agtgtatact ggcttaacta tgcggcatca   10200
gagcagattg tactgagagt gcaccatatg cggtgtgaaa taccgcacag atgcgtaagg   10260
agaaaatacc gcatcaggcg ctcttccgct tcctcgctca ctgactcgct gcgctcggtc   10320
gttcggctgc ggcgagcggt atcagctcac tcaaaggcgg taatacgtt atccacagaa   10380 tcaggggata acgcaggaaa gaacatgtga gcaaaaggcc agcaaaaggc caggaaccgt   10440
aaaaaggccg cgttgctggc gtttttccat aggctccgcc cccctgacga gcatcacaaa   10500
aatcgacgct caagtcagag gtggcgaaac ccgacaggac tataaagata ccaggcgttt   10560
ccccctggaa gctccctcgt gcgctctcct gttccgaccc tgccgcttac cggatacctg   10620
tccgcctttc tcccttcggg aagcgtggcg ctttctcata gctcacgctg taggtatctc   10680
agttcggtgt aggtcgttcg ctccaagctg ggctgtgtgc acgaaccccc cgttcagccc   10740
gaccgctgcg ccttatccgg taactatcgt cttgagtcca acccggtaag acacgactta   10800
tcgccactgg cagcagccac tggtaacagg attagcagag cgaggtatgt aggcggtgct   10860
acagagttct tgaagtggtg gcctaactac ggctacacta aaggacagt atttggtatc   10920 tgcgctctgc tgaagccagt taccttcgga aaaagagttg gtagctcttg atccggcaaa   10980
caaaccaccg ctggtagcgg tggttttttt gtttgcaagc agcagattac gcgcagaaaa   11040
aaaggatctc aagaagatcc tttgatcttt tctacggggt ctgacgctca gtggaacgaa   11100
aactcacgtt aagggatttt ggtcatgaga ttatcaaaaa ggatcttcac ctagatcctt   11160
ttctagataa tacgactcac tata                                          11184
```

<210> SEQ ID NO 12
<211> LENGTH: 11313
<212> TYPE: DNA
<213> ORGANISM: Artificial Sequence
<220> FEATURE:
<223> OTHER INFORMATION: Plasmid

<400> SEQUENCE: 12

```
gccagccccc gattgggggc gacactccac catagatcac tccctgtga ggaactactg    60 tcttcacgca gaaagcgtct agccatggcg ttagtatgag tgtcgtgcag cctccaggac   120 ccccctccc gggagagcca tagtggtctg cggaaccggt gagtacaccg gaattgccag    180
gacgaccggg tcctttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgcccgggg aggtctcgta gaccgtgcac catgagcacg aatcctaaac   360
ctcaaagaaa aaccaaaggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc aggggcgccc ggttcttttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg ggcaggatc tcctgtcatc tcaccttgct cctgccgaga    720 agtatccat catggctgat gcaatgcggc ggctgcatac gcttgatccg gctacctgcc    780
cattcgacca ccaagcgaaa catcgcatcg agcgagcacg tactcggatg aagccggtc    840 ttgtcgatca ggatgatctg gacgaagagc atcagggct cgcgccagcc gaactgttcg    900
ccaggctcaa ggcgcgcatg cccgacgcg aggatctcgt cgtgacccat ggcgatgcct   960
gcttgccgaa tatcatggtg gaaaatggcc gcttttctgg attcatcgac tgtggccggc  1020
tgggtgtggc ggaccgctat caggacatag cgttggctac ccgtgatatt gctgaagagc  1080
ttggcggcga atgggctgac cgcttcctcg tgctttacgg tatcgccgct cccgattcgc  1140
agcgcatcgc cttctatcgc cttcttgacg agttcttctg agtttaaaca gaccacaacg  1200
gtttccctct agcgggatca attccgcccc tctccctccc cccccctaa cgttactggc   1260 cgaagccgct tggaataagg ccggtgtgcg tttgtctata tgttattttc caccatattg  1320
ccgtcttttg gcaatgtgag ggcccggaaa cctggccctg tcttcttgac gagcattcct  1380
aggggtcttt cccctctcgc caaaggaatg caaggtctgt tgaatgtcgt gaaggaagca  1440
gttcctctgg aagcttcttg aagacaaaca acgtctgtag cgaccctttg caggcagcgg  1500
aaccccccac ctggcgacag tgcctctgc ggccaaaagc cacgtgtata agatacacct   1560
gcaaaggcgg cacaacccca gtgccacgtt gtgagttgga tagttgtgga aagagtcaaa  1620
tggctctcct caagcgtatt caacaagggg ctgaaggatg cccagaaggt accccattgt  1680
atgggatctg atctggggcc tcggtgcaca tgctttacat gtgtttagtc gaggttaaaa  1740
aacgtctagg ccccccgaac cacggggacg tggttttcct ttgaaaaaca cgataatacc  1800
atggcgccta ttacggccta ctcccaacag acgcgaggcc tacttggctg catcatcact  1860
agcctcacag gccgggacag gaaccaggtc gaggggagg tccaagtggt ctccaccgca   1920
acacaatctt tcctggcgac ctgcgtcaat ggcgtgtgtt ggactgtcta tcatggtgcc  1980
ggctcaaaga cccttgccgg cccaagggc ccaatcaccc aaatgtacac caatgtggac   2040
caggacctcg tcggctggca agcgcccccc ggggcgcgtt ccttgacacc atgcacctgc  2100
ggcagctcgg acctttactt ggtcacgagg catgccgatg tcattccggt gcgccggcgg  2160
ggcgacagca gggggagcct actctccccc aggcccgtct cctacttgaa gggctcttcg  2220
ggcggtccac tgctctgccc ctcggggcac gctgtgggca tctttcgggc tgccgtgtgc  2280
acccgagggg ttgcgaaggc ggtggacttt gtacccgtcg agtctatgga aaccactatg  2340
cggtccccgg tcttcacgga caactcgtcc cctccggccg taccgcagac attccaggtg  2400
```

-continued

```
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacggGtg cccccatcac gtactccacc tatggcaagt tcttgccga cggtggttgc     2640 tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga atccccttt  tatggcaaag ccatccccat cgagaccatc    2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcgagacgt  cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcagctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtcttta  ccgggagttc    3840 gatgagatgg aagagtgcgc ctcacacctc ccttacatcg aacggggaat gcagctcgcc    3900
gaacatttca acagaaggc  aatcggggttg ctgcaaacag ccaccaagca agcggaggct    3960
gctgctcccg cggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg  gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag gggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
```

```
gtcccttct tctcatgtca acgtgggtac aagggagtct ggcggggcga cggcatcatg   4800
caaaccacct gcccatgtgg agcacagatc accggacatg tgaaaaacgg ttccatgagg   4860
atcgtgggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagg agtacgtgga ggttacgcgg gtgggggatt tccactacgt gacgggcatg   5040
accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgacccct ccacattac ggcggagacg   5280
gctaagcgta ggctggccag gggatctccc ccctccttgg ccagctcatc agctagccag   5340
ctgtctgcgc cttccttgaa ggcaacatgc actacccgtc atgactcccc ggacgctgac   5400
ctcatcgagg ccaacctcct gtggcggcag gagatgggcg ggaacatcac ccgcgtggag   5460
tcagaaaata aggtagtaat tttggactct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggaa ggacccggac   5640
tacgtccctc cagtggtaca cggggtgtcca ttgccgcctg ccaaggcccc tccgatacca   5700
cctccacgga ggaagaggac ggttgtcctg tcagaatcta ccgtgtcttc tgccttggcg   5760
gagctcgcca caaagacctt cggcagctcc gaatcgtcgg ccgtcgacag cggcacggca   5820
acggcctctc ctgaccagcc ctccgacgac ggcgacgcgg gatccgacgt tgagtcgtac   5880
tcctccatgc cccccttga gggggagccg ggggatcccg atctcagcga cgggtcttgg   5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tgggcaaag   6300
gacgtccgga acctatccag caaggccgtt aaccacatcc gctccgtgtg gaaggacttg   6360
ctggaagaca ctgagacacc aattgacacc accatcatgg caaaaaatga ggttttctgc   6420
gtccaaccag agaaggggg ccgcaagcca gctcgcctta tcgtattccc agatttgggg   6480
gttcgtgtgt gcgagaaaat ggccctttac gatgtggtct ccaccctccc tcaggccgtg   6540
atgggctctt catacggatt ccaatactct cctggacagc gggtcgagtt cctggtgaat   6600
gcctggaaag cgaagaaatg ccctatgggc ttcgcatatg acacccgctg ttttgactca   6660
acggtcactg agaatgacat ccgtgttgag gagtcaatct accaatgttg gacttggcc   6720
cccgaagcca gacaggccat aaggtcgctc acagagcggc tttacatcgg ggcccctg   6780
actaattcta aagggcagaa ctgcggctat cgccggtgcc gcgcgagcgg tgtactgacg   6840
accagctgcg gtaataccct cacatgttac ttgaaggccg ctgcggcctg tcgagctgcg   6900
aagctccagg actgcacgat gctcgtatgc ggagacgacc ttgtcgttat ctgtgaaagc   6960
gcgggaccc aagaggacga ggcgagccta cgggccttca cggaggctat gactagatac   7020
tctgccccc ctgggaccc gcccaaacca gaatacgact tggagttgat aacatcatgc   7080
tcctccaatg tgtcagtcgc gcacgatgca tctggcaaaa gggtgtacta tctcacccgt   7140
```

```
gaccccacca cccccttgc gcgggctgcg tgggagacag ctagacacac tccagtcaat   7200
tcctggctag gcaacatcat catgtatgcg cccaccttgt gggcaaggat gatcctgatg   7260
actcatttct tctccatcct tctagctcag gaacaacttg aaaaagcct agattgtcag    7320
atctacgggg cctgttactc cattgagcca cttgacctac ctcagatcat tcaacgactc   7380
catggcctta gcgcatttc actccatagt tactctccag gtgagatcaa tagggtggct    7440
tcatgcctca ggaaacttgg ggtaccgccc ttgcgagtct ggagacatcg gccagaagt    7500
gtccgcgcta ggctactgtc ccaggggggg agggctgcca cttgtggcaa gtacctcttc   7560
aactgggcag taaggaccaa gctcaaactc actccaatcc cggctgcgtc ccagttggat   7620
ttatccagct ggttcgttgc tggttacagc gggggagaca tatatcacag cctgtctcgt   7680
gcccgacccc gctggttcat gtggtgccta ctcctacttt ctgtagggt aggcatctat    7740
ctactcccca accgatgaac ggggacctaa acactccagg ccaataggcc atcctgtttt   7800
tttcccttt tttttttctt tttttttttt tttttttttt tttttttttt ttctccttt    7860
ttttcctct tttttccctt ttcttttcctt tggtggctcc atcttagccc tagtcacggc   7920
tagctgtgaa aggtccgtga gccgcttgac tgcagagagt gctgatactg gcctctctgc   7980
agatcaagta ctcctgcagg cgcgccacta gtgggaatac gcggggtatg ccgcgtttta   8040
gcatattgac gacccaattc tcatgtttga cagcttatca tcgataagct taatgcggt    8100
agtttatcac agttaaattg ctaacgcagt caggcaccgt gtatgaaatc taacaatgcg   8160
ctcatcgtca tcctcggcac cgtcaccctg gatgctgtag gcataggctt ggttatgccg   8220
gtactgccgg gcctcttgcg ggatatcgtc cattccgaca gcatcgccag tcactatggc   8280
gtgctgctag cgctatatgc gttgatgcaa tttctatgcg cacccgttct cggagcactg   8340
tccgaccgct ttggccgccg cccagtcctg ctcgcttcgc tacttggagc cactatcgac   8400
tacgcgatca tggcgaccac accgtcctg tggatcctct acgccggacg catcgtggcc    8460
ggcatcaccg gcgccacagg tgcggttgct ggcgcctata tcgccgacat caccgatggg   8520
gaagatcggg ctcgccactt cgggctcatg agcgcttgtt tcggcgtggg tatggtggca   8580
ggccccgtgg ccgggggact gttgggcgcc atctccttgc atgcaccatt ccttgcggcg   8640
gcggtgctca acggcctcaa cctactactg ggctgcttcc taatgcagga gtcgcataag   8700
ggagagcgtc gaccgatgcc cttgagagcc ttcaacccag tcagctcctt ccggtgggcg   8760
cggggcatga ctatcgtcgc cgcacttatg actgtcttct ttatcatgca actcgtagga   8820
caggtgccgg cagcgctctg ggtcattttc ggcgaggacc gctttcgctg gagcgcgacg   8880
atgatcggcc tgtcgcttgc ggtattcgga atccttcacg ccctcgctca agccttcgtc   8940
actggtcccg ccaccaaacg tttcggcgag aagcaggcca ttatcgccgg catggcggcc   9000
gacgcgctgg gctacgtctt gctggcgttc gcgacgcgag gctggatggc cttccccatt   9060
atgattcttc tcgcttccgg cggcatcggg atgcccgcgt tgcaggccat gctgtccagg   9120
caggtagatg acgaccatca gggacagctt caaggatcgc tcgcggctct taccagccta   9180
acttcgatca ctggaccgct gatcgtcacg gcgatttatg ccgcctcggc gagcacatgg   9240
aacgggttgg catggattgt aggcgccgcc ctataccttg tctgcctccc cgcgttgcgt   9300
cgcggtgcat ggagccgggc cacctcgacc tgaatggaag ccggcggcac ctcgctaacg   9360
gattcaccac tccaagaatt ggagccaatc aattcttgcg gagaactgtg aatgcgcaaa   9420
ccaacccttg gcagaacata tccatcgcgt ccgccatctc cagcagccgc acgcggcgca   9480
```

```
tctcgggcag cgttgggtcc tggccacggg tgcgcatgat cgtgctcctg tcgttgagga    9540
cccggctagg ctggcggggt tgccttactg gttagcagaa tgaatcaccg atacgcgagc    9600
gaacgtgaag cgactgctgc tgcaaaacgt ctgcgacctg agcaacaaca tgaatggtct    9660
tcggtttccg tgtttcgtaa agtctggaaa cgcggaagtc agcgccctgc accattatgt    9720
tccggatctg catcgcagga tgctgctggc taccctgtgg aacacctaca tctgtattaa    9780
cgaagcgctg gcattgaccc tgagtgattt ttctctggtc ccgccgcatc catacccgcc    9840
gttgtttacc ctcacaacgt tccagtaacc gggcatgttc atcatcagta acccgtatcg    9900
tgagcatcct ctctcgtttc atcggtatca ttaccccat gaacagaaat tccccccttac    9960 acggaggcat caagtgacca acaggaaaa accgcccctt aacatggccc gctttatcag    10020
aagccagaca ttaacgcttc tggagaaact caacgagctg gacgcggatg aacaggcaga    10080
catctgtgaa tcgcttcacg accacgctga tgagctttac cgcagctgcc tcgcgcgttt    10140
cggtgatgac ggtgaaaacc tctgacacat gcagctcccg gagacggtca cagcttgtct    10200
gtaagcggat gccgggagca gacaagcccg tcagggcgcg tcagcgggtg ttggcgggtg    10260
tcggggcgca gccatgaccc agtcacgtag cgatagcgga gtgtatactg gcttaactat    10320
gcggcatcag agcagattgt actgagagtg caccatatgc ggtgtgaaat accgcacaga    10380
tgcgtaagga gaaataccg catcaggcgc tcttccgctt cctcgctcac tgactcgctg    10440
cgctcggtcg ttcggctgcg gcgagcggta tcagctcact caaaggcggt aatacggtta    10500
tccacagaat caggggataa cgcaggaaag aacatgtgag caaaaggcca gcaaaaggcc    10560
aggaaccgta aaaaggccgc gttgctggcg tttttccata ggctccgccc ccctgacgag    10620
catcacaaaa atcgacgctc aagtcagagg tggcgaaacc cgacaggact ataaagatac    10680
caggcgtttc cccctggaag ctccctcgtg cgctctcctg ttccgaccct gccgcttacc    10740
ggatacctgt ccgcctttct cccttcggga agcgtggcgc tttctcatag ctcacgctgt    10800
aggtatctca gttcggtgta ggtcgttcgc tccaagctgg gctgtgtgca cgaaccccc    10860 gttcagcccg accgctgcgc cttatccggt aactatcgtc ttgagtccaa cccggtaaga    10920
cacgacttat cgccactggc agcagccact ggtaacagga ttagcagagc gaggtatgta    10980
ggcggtgcta cagagttctt gaagtggtgg cctaactacg gctacactag aaggacagta    11040
tttggtatct gcgctctgct gaagccagtt accttcggaa aaagagttgg tagctcttga    11100
tccggcaaac aaaccaccgc tggtagcggt ggttttttg tttgcaagca gcagattacg    11160
cgcagaaaaa aaggatctca agaagatcct ttgatctttt ctacggggtc tgacgctcag    11220
tggaacgaaa actcacgtta agggattttg gtcatgagat tatcaaaaag gatcttcacc    11280
tagatccttt tctagataat acgactcact ata    11313
```

<210> SEQ ID NO 13
<211> LENGTH: 11184
<212> TYPE: DNA
<213> ORGANISM: Artificial Sequence
<220> FEATURE:
<223> OTHER INFORMATION: Plasmid

<400> SEQUENCE: 13

```
gccagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaacccg ctcaatgcct ggagatttgg gcgtgccccc     240
```

```
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg aagccggtc    840 ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc ccccccctaa cgttactggc    1260
cgaagccgct tggaataagg ccggtgtgcg tttgtctata tgttatttc caccatattg    1320 ccgtcttttg gcaatgtgag ggcccggaaa cctggccctg tcttcttgac gagcattcct    1380 aggggtctt cccctctcgc caaggaatg caaggtctgt tgaatgtcgt gaaggaagca    1440
gttcctctgg aagcttcttg aagacaaaca acgtctgtag cgaccctttg caggcagcgg    1500
aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccgggt aaggaccatc    2580
```

```
accacgggtg cccccatcac gtactccacc tatggcaagt ttcttgccga cggtggttgc   2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatccccttt tatggcaaag ccatccccat cgagaccatc   2880
aagggggga ggcacctcat tttctgccat tccaagaaga aatgtgatga gctcgccgcg   2940
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg taggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360
ccagggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gcccctgctg   3600
tataggctgg gagccgttca aaacgaggtt actaccacac accccataac caaatacatc   3660
atggcatgca tgtcagctga cctggaggtc gtcacgagca cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtcttta ccgggagttc   3840
gatgagatga agagtgcgc ctcacacctc ccttacatcg aacggggaat gcagctcgcc   3900
gaacatttca aacagaaggc aatcgggttg ctgcaaacag ccaccaagca agcggaggct   3960
gctgctcccg cggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgccctcc accgaggacc tggttaacct actccctgct   4380
atcctctccc ctggcgccct agtcgtcggg gtcgtgtgcg cagcgatact gcgtcggcac   4440
gtgggcccag ggagggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtcccctttc tctcatgtca acgtgggtac aaggagtct ggcggggcga cggcatcatg   4800
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
```

```
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cactcccgga ttacaaccct ccactgttag agtcctggaa ggacccggac    5640
tacgtccctc cagtggtaca cgggtgtcca ttgccgcctg ccaaggcccc tccggtacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctggtgagga cgtcgtctgc tgctcgatgt cctacacatg gacaggcgcc    5880
ctgatcacgc catgcgctgc ggaggaaacc aagctgccca tcaatgcact gagcaactct    5940
ttgctccgac accacaactt ggtctatgct acaacatctc gcagcgcaag cctgcggcag    6000
aagaaggtca cctttgacag actgcaggtc ctggacgacc actaccggga cgtgctcaag    6060
gagatgaagg cgaaggcgtc cacagttaag gctaaacttc tatccgtgga ggaagcctgt    6120 aagctgcgc ccccacattc ggccagatct aaatttggct atggggcaaa ggacgtccgg    6180
aacctatcca gcaaggccgt taaccacatc cgctccgtgt ggaaggactt gctggaagac    6240
actgagacac caattgacac caccatcatg gcaaaaaatg aggttttctg cgtccaacca    6300
gagaaggggg gccgcaagcc agctcgcctt atcgtattcc cagatttggg ggttcgtgtg    6360
tgcgagaaaa tggccccttta cgatgtggtc tccaccctcc ctcaggccgt gatgggctct    6420
tcatacggat ccaatactc tcctggacag cgggtcgagt tcctggtgaa tgcctggaaa    6480
gcgaagaaat gccctatggg cttcgcatat gacacccgct gttttgactc aacggtcact    6540
gagaatgaca tccgtgttga ggagtcaatc taccaatgtt gtgacttggc ccccgaagcc    6600
agacaggcca taaggtcgct cacagagcgg ctttacatcg ggggcccccct gactaattct    6660 aaagggcaga actgcggcta tcgccggtgc cgcgcgagcg gtgtactgac gaccagctgc    6720
ggtaataccc tcacatgtta cttgaaggcc gctgcgcct gtcgagctgc gaagctccag    6780
gactgcacga tgctcgtatg cggagacgac cttgtcgtta tctgtgaaag cgcggggacc    6840
caagaggacg aggcgagcct acgggccttc acggaggcta tgactagata ctctgccccc    6900 cctgggacc cgcccaaacc agaatacgac ttggagttga taacatcatg ctcctccaat    6960
gtgtcagtcg cgcacgatgc atctggcaaa agggtgtact atctcacccg tgaccccacc    7020 acccccttg cgcgggctgc gtgggagaca gctagacaca ctccagtcaa ttcctggcta    7080
ggcaacatca tcatgtatgc gcccaccttg tgggcaagga tgatcctgat gactcatttc    7140
ttctccatcc ttctagctca ggaacaactt gaaaaagccc tagattgtca gatctacggg    7200
gcctgttact ccattgagcc acttgaccta cctcagatca ttcaacgact ccatggcctt    7260
agcgcatttt cactccatag ttactctcca ggtgagatca atagggtggc ttcatgcctc    7320
```

```
aggaaacttg gggtaccgcc cttgcgagtc tggagacatc gggccagaag tgtccgcgct   7380
aggctactgt cccaggggggg gagggctgcc acttgtggca agtacctctt caactgggca  7440
gtaaggacca agctcaaact cactccaatc ccggctgcgt cccagttgga tttatccagc   7500
tggttcgttg ctggttacag cgggggagac atatatcaca gcctgtctcg tgcccgaccc   7560
cgctggttca tgtggtgcct actcctactt tctgtagggg taggcatcta tctactcccc   7620
aaccgatgaa cggggaccta aacactccag gccaataggc catcctgttt ttttcccttt   7680 tttttttttct ttttttttttt ttttttttttt tttttttttt ttttctcctttt tttttttcctc 7740 ttttttttcct tttctttcct ttggtggctc catcttagcc ctagtcacgg ctagctgtga  7800
aaggtccgtg agccgcttga ctgcagagag tgctgatact ggcctctctg cagatcaagt   7860
actcctgcag gcgcgccact agtgggaata cgcggggtat gccgcgtttt agcatattga   7920
cgacccaatt ctcatgtttg acagcttatc atcgataagc tttaatgcgg tagtttatca   7980
cagttaaatt gctaacgcag tcaggcaccg tgtatgaaat ctaacaatgc gctcatcgtc   8040
atcctcggca ccgtcaccct ggatgctgta ggcataggct tggttatgcc ggtactgccg   8100
ggcctcttgc gggatatcgt ccattccgac agcatcgcca gtcactatgg cgtgctgcta   8160
gcgctatatg cgttgatgca atttctatgc gcacccgttc tcggagcact gtccgaccgc   8220
tttggccgcc gcccagtcct gctcgcttcg ctacttggag ccactatcga ctacgcgatc   8280
atggcgacca caccgtcct gtggatcctc tacgccggac gcatcgtggc cggcatcacc   8340
ggcgccacag gtgcggttgc tggcgcctat atcgccgaca tcaccgatgg ggaagatcgg   8400
gctcgccact tcgggctcat gagcgcttgt ttcggcgtgg gtatggtggc aggccccgtg   8460
gccgggggac tgttgggcgc catctccttg catgcaccat tccttgcggc ggcggtgctc   8520
aacggcctca acctactact gggctgcttc ctaatgcagg agtcgcataa gggagagcgt   8580
cgaccgatgc ccttgagagc cttcaaccca gtcagctcct tccggtgggc gcggggcatg   8640
actatcgtcg ccgcacttat gactgtcttc tttatcatgc aactcgtagg acaggtgccg   8700
gcagcgctct gggtcatttt cggcgaggac cgctttcgct ggagcgcgac gatgatcggc   8760
ctgtcgcttg cggtattcgg aatcttgcac gccctcgctc aagccttcgt cactggtccc   8820
gccaccaaac gtttcggcga agcaggcc attatcgccg gcatggcggc cgacgcgctg   8880
ggctacgtct tgctggcgtt cgcgacgcga ggctggatgg ccttccccat tatgattctt   8940
ctcgcttccg gcggcatcgg gatgcccgcg ttgcaggcca tgctgtccag gcaggtagat   9000
gacgaccatc agggacagct tcaaggatcg ctcgcggctc ttaccagcct aacttcgatc   9060
actggaccgc tgatcgtcac ggcgatttat gccgcctcgg cgagcacatg gaacgggttg   9120
gcatggattg taggcgccgc cctataccttt gtctgcctcc ccgcgttgcg tcgcggtgca   9180
tggagccggg ccacctcgac ctgaatggaa gccggcggca cctcgctaac ggattcacca   9240
ctccaagaat tggagccaat caattcttgc ggagaactgt gaatgcgcaa accaaccctt   9300
ggcagaacat atccatcgcg tccgccatct ccagcagccg cacgcggcgc atctcgggca   9360
gcgttgggtc ctggccacgg gtgcgcatga tcgtgctcct gtcgttgagg acccggctag   9420
gctggcgggg ttgccttact ggttagcaga atgaatcacc gatacgcgag cgaacgtgaa   9480
gcgactgctg ctgcaaaacg tctgcgacct gagcaacaac atgaatggtc ttcggtttcc   9540
gtgtttcgta aagtctggaa acgcggaagt cagcgccctg caccattatg ttccggatct   9600
gcatcgcagg atgctgctgg ctaccctgtg gaacacctac atctgtatta acgaagcgct   9660
ggcattgacc ctgagtgatt tttctctggt cccgccgcat ccataccgcc agttgtttac   9720
```

-continued

```
cctcacaacg ttccagtaac cgggcatgtt catcatcagt aacccgtatc gtgagcatcc    9780
tctctcgttt catcggtatc attacccca  tgaacagaaa ttcccccctta cacggaggca    9840 tcaagtgacc aaacaggaaa aaaccgccct aacatggcc  cgctttatca gaagccagac    9900
attaacgctt ctggagaaac tcaacgagct ggacgcggat gaacaggcag acatctgtga    9960
atcgcttcac gaccacgctg atgagcttta ccgcagctgc ctcgcgcgtt tcggtgatga   10020
cggtgaaaac ctctgacaca tgcagctccc ggagacggtc acagcttgtc tgtaagcgga   10080
tgccgggagc agacaagccc gtcagggcgc gtcagcgggt gttggcgggt gtcggggcgc   10140
agccatgacc cagtcacgta gcgatagcgg agtgtatact ggcttaacta tgcggcatca   10200
gagcagattg tactgagagt gcaccatatg cggtgtgaaa taccgcacag atgcgtaagg   10260
agaaaatacc gcatcaggcg ctcttccgct tcctcgctca ctgactcgct gcgctcggtc   10320
gttcggctgc ggcgagcggt atcagctcac tcaaaggcgg taatacggtt atccacagaa   10380 tcagggata  acgcaggaaa gaacatgtga gcaaaaggcc agcaaaaggc caggaaccgt   10440
aaaaaggccg cgttgctggc gtttttccat aggctccgcc cccctgacga gcatcacaaa   10500
aatcgacgct caagtcagag gtggcgaaac ccgacaggac tataaagata ccaggcgttt   10560
ccccctggaa gctccctcgt gcgctctcct gttccgaccc tgccgcttac cggatacctg   10620
tccgcctttc tcccttcggg aagcgtggcg ctttctcata gctcacgctg taggtatctc   10680
agttcggtgt aggtcgttcg ctccaagctg ggctgtgtgc acgaaccccc cgttcagccc   10740
gaccgctgcg ccttatccgg taactatcgt cttgagtcca acccggtaag cacgactta    10800 tcgccactgg cagcagccac tggtaacagg attagcagag cgaggtatgt aggcggtgct   10860
acagagttct tgaagtggtg gcctaactac ggctacacta aaggacagt  atttggtatc   10920 tgcgctctgc tgaagccagt taccttcgga aaagagttg  gtagctcttg atccggcaaa   10980
caaaccaccg ctggtagcgg tggttttttt gtttgcaagc agcagattac gcgcagaaaa   11040
aaaggatctc aagaagatcc tttgatcttt tctacggggt ctgacgctca gtggaacgaa   11100
aactcacgtt aagggatttt ggtcatgaga ttatcaaaaa ggatcttcac ctagatcctt   11160
ttctagataa tacgactcac tata                                          11184
```

<210> SEQ ID NO 14
<211> LENGTH: 11184
<212> TYPE: DNA
<213> ORGANISM: Artificial Sequence
<220> FEATURE:
<223> OTHER INFORMATION: Plasmid

<400> SEQUENCE: 14

```
gccagccccc gattggggc  gacactccac catagatcac tcccctgtga ggaactactg      60
tcttcacgca gaaagcgtct agccatggcg ttagtatgag tgtcgtgcag cctccaggac     120 ccccctccc  gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta tgtttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaagggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc agggcgccc  ggttctttt  gtcaagaccg     540
```

-continued

```
acctgtccgg tgccctgaat gaactgcagg acgaggcagc gcggctatcg tggctggcca      600
cgacgggcgt tccttgcgca gctgtgctcg acgttgtcac tgaagcggga agggactggc      660
tgctattggg cgaagtgccg ggcaggatc tcctgtcatc tcaccttgct cctgccgaga       720
aagtatccat catggctgat gcaatgcggc ggctgcatac gcttgatccg ctacctgcc       780
cattcgacca ccaagcgaaa catcgcatcg agcgagcacg tactcggatg gaagccggtc      840
ttgtcgatca ggatgatctg gacgaagagc atcaggggct cgcgccagcc gaactgttcg      900
ccaggctcaa ggcgcgcatg cccgacggcg aggatctcgt cgtgacccat ggcgatgcct      960
gcttgccgaa tatcatggtg gaaaatggcc gcttttctgg attcatcgac tgtggccggc     1020
tgggtgtggc ggaccgctat caggacatag cgttggctac ccgtgatatt gctgaagagc     1080
ttggcggcga atgggctgac cgcttcctcg tgctttacgg tatcgccgct cccgattcgc     1140
agcgcatcgc cttctatcgc cttcttgacg agttcttctg agtttaaaca gaccacaacg     1200
gtttccctct agcgggatca attccgcccc tctccctccc ccccccctaa cgttactggc     1260
cgaagccgct tggaataagg ccggtgtgcg tttgtctata tgttattttc caccatattg     1320
ccgtcttttg gcaatgtgag ggcccggaaa cctggccctg tcttcttgac gagcattcct     1380
aggggtcttt cccctctcgc caaggaatg caaggtctgt tgaatgtcgt gaaggaagca      1440
gttcctctgg aagcttcttg aagacaaaca acgtctgtag cgaccctttg caggcagcgg     1500
aacccccac ctggcgacag gtgcctctgc ggccaaaagc cacgtgtata agatacacct      1560
gcaaaggcgg cacaacccca gtgccacgtt gtgagttgga tagttgtgga aagagtcaaa     1620
tggctctcct caagcgtatt caacaagggg ctgaaggatg cccagaaggt accccattgt     1680
atgggatctg atctggggcc tcggtgcaca tgctttacat gtgtttagtc gaggttaaaa     1740
aacgtctagg ccccccgaac cacggggacg tggttttcct ttgaaaaaca cgataatacc     1800
atggcgccta ttacggccta ctcccaacag acgcgaggcc tacttggctg catcatcact     1860
agcctcacag gccgggacag gaaccaggtc gaggggagg tccaagtggt ctccaccgca      1920
acacaatctt tcctggcgac ctgcgtcaat ggcgtgtgtt ggactgtcta tcatggtgcc     1980
ggctcaaaga cccttgccgg cccaaagggc ccaatcaccc aaatgtacac caatgtggac     2040
caggacctcg tcggctggca agcgcccccc ggggcgcgtt ccttgacacc atgcacctgc     2100
ggcagcgcgg acctttactt ggtcacgagg catgccgatg tcattccggt gcgccggcgg     2160
ggcgacagca gggggagcct actctccccc aggcccgttt cctacttgaa gggctcttcg     2220
ggcggtccac tgctctgccc ctcggggcac gctgtgggca tctttcgggc tgccgtgtgc     2280
acccgagggg ttgcgaaggc ggtggacttt gtacccgtcg agtctatggg aaccactatg     2340
cggtccccgg tcttcacgga caactcgtcc cctccgccg taccgcagac attccaggtg      2400
gcccatctac acgcccctac tggtagcggc aagagcacta aggtgccggc tgcgtatgca     2460
gcccaagggt ataaggtgct tgtcctgaac ccgtccgtcg ccgccaccct aggtttcggg     2520
gcgtatatgt ctaaggcaca tggtatcgac cctaacatca gaaccggggt aaggaccatc     2580
accacgggtg cccccatcac gtactccacc tatggcaagt tcttgccga cggtggttgc      2640
tctgggggcg cctatgacat cataatatgt gatgagtgcc actcaactga ctcgaccact     2700
atcctggca tcggcacagt cctggaccaa gcggagacgg ctgagcgcg actcgtcgtg       2760
ctcgccaccg ctacgcctcc gggatcggtc accgtgccac atccaaacat cgaggaggtg     2820
gctctgtcca gcactggaga aatcccctt tatggcaaag ccatcccat cgagaccatc       2880
aagggggga ggcacctcat tttctgccat tccaagaaga aatgtgatga gctcgccgcg      2940
```

-continued

```
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg taggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360
ccagggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gccctgctg    3600 tataggctgg gagccgttca aaacgaggtt actaccacac accccataac caaatacatc   3660
atggcatgca tgtcagctga cctggaggtc gtcacgagca cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtctttta ccggagttc    3840 gatgagatgg aagagtgcgc ctcacacctc ccttacatcg aacggggaat gcagctcgcc   3900
gaacatttca acagaaggc aatcgggttg ctgcaaacag ccaccaagca agcggaggct    3960
gctgctcccg cggtggaatc caagtggcgg accctcgaag ccttctgggc gaagcatatg   4020
tggaatttca tcagcgggat acaatattta gcaggcttgt ccactctgcc tggcaacccc   4080
gcgatagcat cactgatggc attcacagcc tctatcacca gcccgctcac cacccaacat   4140
accctcctgt ttaacatcct gggggggatgg gtggccgccc aacttgctcc tcccagcgct   4200
gcttctgctt tcgtaggcgc cggcatcgct ggagcggctc ttggcagcat aggccttggg   4260
aaggtgcttg tggatatttt ggcaggttat ggagcagggg tggcaggcgc gctcgtggcc   4320
tttaaggtca tgagcggcga gatgcctcc accgaggacc tggttaacct actccctgct    4380
atcctctccc ctggcgccct agtcgtcggg gtcgtgtgcg cagcgatact gcgtcggcac   4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
caaaccacct gcccatgtgg agcacagatc accggacatg tgaaaaacgg ttccatgagg   4860 atcgtgggc ctaggacctg tagtaacacg tggcatggaa cattccccat taacgcgtac    4920
accacgggcc cctgcacgcc ctcccggcg ccaaattatt ctagggcgct gtggcgggtg    4980
gctgctgagg agtacgtgga ggttacgcgg gtgggggatt ccactacgt gacgggcatg     5040 accactgaca acgtaaagtg cccgtgtcag gttccggccc ccgaattctt cacagaagtg   5100
gatggggtgc ggttgcacag gtacgctcca gcgtgcaaac ccctcctacg gaggaggtc    5160 acattcctgg tcgggctcaa tcaatacctg gttgggtcac agctcccatg cgagcccgaa   5220
ccggacgtag cagtgctcac ttccatgctc accgacccct cccacattac ggcggagacg   5280
```

-continued

```
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggagtct ttcgagccgc tccaagcgga ggaggatgag    5520
agggaagtat ccgttccggc ggagatcctg cggaggtcca ggaaattccc tcgagcgatg    5580
cccatatggg cactcccgga ttacaaccct ccactgttag agtcctggaa ggacccggac    5640
tacgtccctc cagtggtaca cgggtgtcca ttgccgcctg ccaaggcccc tccggtacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctggtgagga cgtcgtctgc tgctcgatgt cctacacatg gacaggcgcc    5880
ctgatcacgc catgcgctgc ggaggaaacc aagctgccca tcaatgcact gagcaactct    5940
ttgctccgac accacaactt ggtctatgct acaacatctc gcagcgcaag cctgcggcag    6000
aagaaggtca cctttgacag actgcaggtc ctggacgacc actaccggga cgtgctcaag    6060
gagatgaagg cgaaggcgtc cacagttaag gctaaacttc tatccgtgga ggaagcctgt    6120
aagctgacgc ccccacattc ggccagatct aaatttggct atggggcaaa ggacgtccgg    6180
aacctatcca gcaaggccgt taaccacatc cgctccgtgt ggaaggactt gctggaagac    6240
actgagacac caattgacac caccatcatg gcaaaaaatg aggttttctg cgtccaacca    6300
gagaagggga gccgcaagcc agctcgcctt atcgtattcc cagatttggg ggttcgtgtg    6360
tgcgagaaaa tggccctta cgatgtggtc tccaccctcc ctcaggccgt gatgggctct    6420
tcatacggat ccaatactc tcctggacag cgggtcgagt tcctggtgaa tgcctggaaa    6480
gcgaagaaat gccctatggg cttcgcatat gacacccgct gttttgactc aacggtcact    6540
gagaatgaca tccgtgttga ggagtcaatc taccaatgtt gtgacttggc ccccgaagcc    6600
agacaggcca taaggtcgct cacagagcgg ctttacatcg ggggcccct gactaattct    6660 aaagggcaga actgcggcta tcgccggtgc cgcgcgagcg tgtactgac gaccagctgc    6720 ggtaataccc tcacatgtta cttgaaggcc gctgcggcct gtcgagctgc gaagctccag    6780
gactgcacga tgctcgtatg cggagacgac cttgtcgtta tctgtgaaag cgcggggacc    6840
caagaggacg aggcgagcct acgggccttc acggaggcta tgactagata ctctgccccc    6900
cctggggacc cgcccaaacc agaatacgac ttggagttga taacatcatg ctcctccaat    6960
gtgtcagtcg cgcacgatgc atctggcaaa agggtgtact atctcacccg tgaccccacc    7020 acccccttg cgcgggctgc gtgggagaca gctagacaca ctccagtcaa ttcctggcta    7080
ggcaacatca tcatgtatgc gcccaccttg tgggcaagga tgatcctgat gactcatttc    7140
ttctccatcc ttctagctca ggaacaactt gaaaaagccc tagattgtca gatctacggg    7200
gcctgttact ccattgagcc acttgaccta cctcagatca ttcaacgact ccatggcctt    7260
agcgcatttt cactccatag ttactctcca ggtgagatca ataggtggc ttcatgcctc    7320 aggaaacttg gggtaccgcc cttgcgagtc tggagacatc gggccagaag tgtccgcgct    7380
aggctactgt cccagggggg gagggctgcc acttgtggca agtacctctt caactgggca    7440
gtaaggacca agctcaaact cactccaatc ccggctgcgt cccagttgga tttatccagc    7500
tggttcgttg ctggttacag cgggggagac atatatcaca gcctgtctcg tgcccgaccc    7560
cgctggttca tgtggtgcct actcctactt tctgtagggg taggcatcta tctactcccc    7620
aaccgatgaa cggggaccta aacactccag gccaataggc catcctgttt ttttcccttt    7680
```

-continued

```
ttttttttct tttttttttt tttttttttt tttttttttt tttctcctttt ttttttcctc      7740
ttttttttcct tttctttcct ttggtggctc catcttagcc ctagtcacgg ctagctgtga      7800
aaggtccgtg agccgcttga ctgcagagag tgctgatact ggcctctctg cagatcaagt      7860
actcctgcag gcgcgccact agtgggaata cgcggggtat gccgcgtttt agcatattga      7920
cgacccaatt ctcatgtttg acagcttatc atcgataagc tttaatgcgg tagtttatca      7980
cagttaaatt gctaacgcag tcaggcaccg tgtatgaaat ctaacaatgc gctcatcgtc      8040
atcctcggca ccgtcaccct ggatgctgta ggcataggct tggttatgcc ggtactgccg      8100
ggcctcttgc gggatatcgt ccattccgac agcatcgcca gtcactatgg cgtgctgcta      8160
gcgctatatg cgttgatgca atttctatgc gcacccgttc tcggagcact gtccgaccgc      8220
tttggccgcc gcccagtcct gctcgcttcg ctacttggag ccactatcga ctacgcgatc      8280
atggcgacca cacccgtcct gtggatcctc tacgccggac gcatcgtggc cggcatcacc      8340
ggcgccacag gtgcggttgc tggcgcctat atcgccgaca tcaccgatgg ggaagatcgg      8400
gctcgccact cgggctcat gagcgcttgt ttcggcgtgg gtatggtggc aggccccgtg      8460
gccgggggac tgttgggcgc catctccttg catgcaccat tccttgcggc ggcggtgctc      8520
aacggcctca acctactact gggctgcttc ctaatgcagg agtcgcataa gggagagcgt      8580
cgaccgatgc ccttgagagc cttcaaccca gtcagctcct tccggtgggc gcggggcatg      8640
actatcgtcg ccgcacttat gactgtcttc tttatcatgc aactcgtagg acaggtgccg      8700
gcagcgctct gggtcatttt cggcgaggac cgctttcgct ggagcgcgac gatgatcggc      8760
ctgtcgcttg cggtattcgg aatcttgcac gccctcgctc aagccttcgt cactggtccc      8820
gccaccaaac gtttcggcga gaagcaggcc attatcgccg gcatggcggc cgacgcgctg      8880
ggctacgtct tgctggcgtt cgcgacgcga ggctggatgg ccttccccat tatgattctt      8940
ctcgcttccg gcggcatcgg gatgcccgcg ttgcaggcca tgctgtccag gcaggtagat      9000
gacgaccatc agggacagct tcaaggatcg ctcgcggctc ttaccagcct aacttcgatc      9060
actggaccgc tgatcgtcac ggcgatttat gccgcctcgg cgagcacatg gaacgggttg      9120
gcatggattg taggcgccgc cctataccttt gtctgcctcc ccgcgttgcg tcgcggtgca      9180
tggagccggg ccacctcgac ctgaatggaa gccggcggca cctcgctaac ggattcacca      9240
ctccaagaat tggagccaat caattcttgc ggagaactgt gaatgcgcaa accaaccctt      9300
ggcagaacat atccatcgcg tccgccatct ccagcagccg cacgcggcgc atctcgggca      9360
gcgttgggtc ctggccacgg gtgcgcatga tcgtgctcct gtcgttgagg acccggctag      9420
gctgcgggg ttgccttact ggttagcaga atgaatcacc gatacgcgag cgaacgtgaa      9480
gcgactgctg ctgcaaaacg tctgcgacct gagcaacaac atgaatggtc ttcggtttcc      9540
gtgtttcgta aagtctggaa acgcggaagt cagcgccctg caccattatg ttccggatct      9600
gcatcgcagg atgctgctgg ctaccctgtg gaacacctac atctgtatta acgaagcgct      9660
ggcattgacc ctgagtgatt tttctctggt cccgccgcat ccataccgcc agttgtttac      9720
cctcacaacg ttccagtaac cgggcatgtt catcatcagt aacccgtatc gtgagcatcc      9780
tctctcgttt catcggtatc attaccccca tgaacagaaa ttccccctta cacggaggca      9840
tcaagtgacc aaacaggaaa aaaccgccct taacatggcc cgctttatca gaagccagac      9900
attaacgctt ctggagaaac tcaacgagct ggacgcggat gaacaggcag acatctgtga      9960
atcgcttcac gaccacgctg atgagcttta ccgcagctgc ctcgcgcgtt tcggtgatga     10020
```

-continued

```
cggtgaaaac ctctgacaca tgcagctccc ggagacggtc acagcttgtc tgtaagcgga    10080
tgccgggagc agacaagccc gtcagggcgc gtcagcgggt gttggcgggt gtcgggcgc     10140 agccatgacc cagtcacgta gcgatagcgg agtgtatact ggcttaacta tgcggcatca    10200
gagcagattg tactgagagt gcaccatatg cggtgtgaaa taccgcacag atgcgtaagg    10260
agaaaatacc gcatcaggcg ctcttccgct tcctcgctca ctgactcgct gcgctcggtc    10320
gttcggctgc ggcgagcgt atcagctcac tcaaaggcgg taatacggtt atccacagaa     10380 tcagggata acgcaggaaa gaacatgtga gcaaaaggcc agcaaaaggc caggaaccgt     10440
aaaaaggccg cgttgctggc gtttttccat aggctccgcc cccctgacga gcatcacaaa    10500
aatcgacgct caagtcagag gtggcgaaac ccgacaggac tataaagata ccaggcgttt    10560
ccccctggaa gctccctcgt gcgctctcct gttccgaccc tgccgcttac cggatacctg    10620
tccgcctttc tcccttcggg aagcgtggcg ctttctcata gctcacgctg taggtatctc    10680
agttcggtgt aggtcgttcg ctccaagctg ggctgtgtgc acgaaccccc cgttcagccc    10740
gaccgctgcg ccttatccgg taactatcgt cttgagtcca acccggtaag acacgactta    10800
tcgccactgg cagcagccac tggtaacagg attagcagag cgaggtatgt aggcggtgct    10860
acagagttct tgaagtggtg gcctaactac ggctacacta aaggacagt atttggtatc      10920 tgcgctctgc tgaagccagt taccttcgga aaaagagttg gtagctcttg atccggcaaa    10980
caaaccaccg ctggtagcgg tggttttttt gtttgcaagc agcagattac gcgcagaaaa    11040
aaaggatctc aagaagatcc tttgatcttt tctacggggt ctgacgctca gtggaacgaa    11100
aactcacgtt aagggatttt ggtcatgaga ttatcaaaaa ggatcttcac ctagatcctt    11160
ttctagataa tacgactcac tata                                          11184

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
agtatcgtgg tagagagctg c                                                21

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
taatacgact cactataggg atgtggctgg agatgc                                36
```